US010106627B2

(12) United States Patent
Kumar et al.

(10) Patent No.: US 10,106,627 B2
(45) Date of Patent: Oct. 23, 2018

(54) PROCESS FOR THE PREPARATION OF POLYMERIC BIOSURFACTANTS

(71) Applicant: COUNCIL OF SCIENTIFIC & INDUSTRIAL RESEARCH, New Delhi (IN)

(72) Inventors: Chityal Ganesh Kumar, Hyderabad (IN); Sujitha Pombala, Hyderabad (IN)

(73) Assignee: COUNCIL OF SCIENTIFIC & INDUSTRIAL RESEARCH (IN)

( * ) Notice: Subject to any disclaimer, the term of this patent is extended or adjusted under 35 U.S.C. 154(b) by 281 days.

(21) Appl. No.: 14/676,117

(22) Filed: Apr. 1, 2015

(65) Prior Publication Data
US 2015/0322173 A1    Nov. 12, 2015

(30) Foreign Application Priority Data

Apr. 1, 2014   (IN) .............................. 939/DEL/2014

(51) Int. Cl.
*A61K 9/50* (2006.01)
*C08B 37/00* (2006.01)
*C12P 19/04* (2006.01)
*C12R 1/01* (2006.01)

(52) U.S. Cl.
CPC .......... *C08B 37/006* (2013.01); *A61K 9/5036* (2013.01); *C12P 19/04* (2013.01); *C12R 1/01* (2013.01)

(58) Field of Classification Search
None
See application file for complete search history.

(56) References Cited

PUBLICATIONS

Kiran, Critical Reviews in Biotechnology, 31:4, 354-364, 2011.*
Desai, J.D. et al., "Microbial Production of Surfactants and Their Commercial Potential", Microbiol. Mol. Biol. Rev., 61, pp. 47-64, (1997).
Banat, I.M., "Biosurfactant Production and Possible Uses in Microbial Enhanced Oil Recovery and Oil Pollution Remediation: A Review", Biores. Technol., 51, pp. 1-12, (1995).
Lee, H. H., et al., "Study on Immunostimulating Activity of Macrophage Treated With Purified Polysaccharides From Liquid Culture and Fruiting body of Lentinus Edodes", J. Microbiol. Biotechnol., 19, pp. 566-572, (2009).
Lee, H. H., et al., Study on Immunostimulating Activity of Macrophage Treated With Purified Polysaccharides From Liquid Culture and Fruiting Body of Lentinus Edodes, J. Microbiol. Biotechnol., 19, pp. 566-572, (2009a).
Lee, J. S., et al., "Study of Macrophage Activation and Structural Characteristics of Purified Polysaccharides From the Fruiting Body of Hericium Erinaceus", J. Microbiol. Biotechnol., 19, pp. 951-959, (2009b).
Medzhitov, R., et al., "Innate Immune Recognition: Mechanisms and Pathways", Immunol. Rev., 173, pp. 89-97, (2000).
Brown, D. M., et al., "Calcium and ROS-mediated Activation of Transcription Factors and TNF-a Cytokine Gene Expression in Macrophages Exposed to Ultrafine Particles", Am. J. Physiol. Lung Cell Mol. Physiol., 286, L344-L353, (2004).
Bae, I. Y., et al., "Rheological Characterization of Levan Polysaccharides From Microbacterium Laevaniformans", Int. J. Biol. Macromol., 42, 10-13, (2008).
Asker, M. M. S., et al., "Chemical Characteristics and Antioxidant Activity of Exopolysaccharide Fractions", From Microbacterium Terregens Carbohydr. Polym., 77 pp. 563-567, (2009).
Godinho, A. L., et al., "Sand Agregation by Exopolysaccharide-Producing", Micorbacterium Arborescens—aGSB, Curr. Microbiol., 58 pp. 616-621, (2009).
Matsuyama, H., et al., "*Microbacterium Kitamiense* sp. *Nov.*, a New Polysaccharide-Producing Bacterium Isolated From the Wastewater of a Sugar-Beet Factory", Int. J. Syst. Bacteriol., 49, pp. 1353-1357, (1999).
Ortega-Morales, B. O., et al., "Characterization of Extracellular Polymers Synthesized by Tropical Intertidal Biofilm Bacteria", J. Appi. Microbiol., 102, pp. 254-264, (2007).
Aniszewski, E., et al., "Bioemulsifier Production by *Microbacterium* sp. Strains Isolated From Mangrove and Their Application to Remove Cadmiun and Zinc From Hazardous Industrial Residue", Brazilian J. Microbial., 41, pp. 235-245, (2010).
Haddad, No. I. A., et al., "Isolation and Characterization of a Biosurfactant Producing Strain", Brevibacilia Brevis HOBI, J. Ind. Microbiol. Biotechnol., 35, pp. 1597-1604, (2008).
Reddy, M. S., et al., "Biodegradation of Phenanthrene With Biosurfactant Production by a New Strain", Of *Brevibacillus* sp. Biores. Technol., 101, pp. 7980-7983, (2010).
Ferhat, S., et al., "Screening and Preliminary Characterization of Biosurfactants Produced by *Ochrobactrum* sp. 1C and *Brevibacterium* sp. 7G Isolated From Hydrocarbon Contaminated Soils", International Biodeterioration and Biodegradation, 65, pp. 1182-1188, (2011).
Radchenkova, N. et al., "Biosynthesis of an Exopolysaccharide Produced by Brevibacillus Thermoruber 438", Biotechnol. Biotechnol. Eq., 25, pp. 77-79, (2011).
Kumar, C. G., et al., "Evaluation of Critical Nutritional Parameters and Their Significance in the Production of Rhamnolipid Biosurfactants From Pseudomonas Aeruginosa BS-161R", Biotechnol. Prog., 28, pp. 1507-1516, (2012).

(Continued)

*Primary Examiner* — Layla D Berry
(74) *Attorney, Agent, or Firm* — Barnes & Thornburg LLP

(57) ABSTRACT

The present invention relates to polymeric biosurfactants isolated from two bacterial strains of *Microbacterium* sp. strain BS-2 [MTCC 5822] and *Brevibacillus* sp. strain BS-207 [MTCC 5823]. The present invention relates to an acidic exopolysaccharide (EPS), termed Microsan, with chemical composition of glucose, mannose and glucuronic acid (β-D-glucuronyl-(1-2)-D-mannosyl-(1-4)-D-glucose) produced by *Microbacterium* sp. strain BS-2 and a neutral EPS, termed Brevisan, of galactomannan with galactose and mannose residues in the ratio of 1:1 produced by *Brevibacillus* sp. strain BS-207. Both these polysaccharides exhibited surface-active and potential antibacterial, antioxidant, anti-inflammatory, and immunomodulatory activities.

6 Claims, 38 Drawing Sheets

(56) References Cited

PUBLICATIONS

Cooper, D.G., et al., "Surface Active Compounds From Microorganisms", Adv. Appl. Microbiol., 26, pp. 229-256, (1980).

Nicolaus, B. et al., "Exopolysaccharides From Extermophiles: From Fundamentals to Biotechnology", Environ, Technol., 31, pp. 1145-1158, (2010).

Kumar, A.S., et al., "Bacterial Exopolysaccharides—a Perception", J. Basic Microbiol., 47, pp. 103-117, (2007).

Novak, M. et al., "Beta-Glucans, History, And The Present: Immunomodulatory Aspects and Mechanisms of Action", J. Immunotoxicol., 5, pp. 47-57, (2008).

Wasser, S.P., "Medicinal Mushrooms As a Source of Antitumor and Immunomodulating Polysaccharides", Appl. Microbiol. Biotechnol., 60, pp. 258-274, (2002).

Beutler, B., "Innate Immunity: An Overview," Mol. Immunol., 40, pp. 845-859, (2004).

MacMicking, J. et al., "Nitric Oxide an Macrophage function", Annu. Rev. Immunol., 15, pp. 323-350, (1997).

Cho, S.M., et al., Chemical Features and Purification of Immunostimulating Polysaccharides From the Fruit Bodies of Agaricus Blazei, Korean J. Mycol., 27, pp. 170-174.

Sun C., et al., Free Radical Scavenging and Antioxidant Activities of EPS2, an Exopolysaccharide Produced by a Marine Filamentous Fungus *Keissleriella* sp. YS 4108, Life Sci., 75, pp. 1063-1073, (2004).

\* cited by examiner

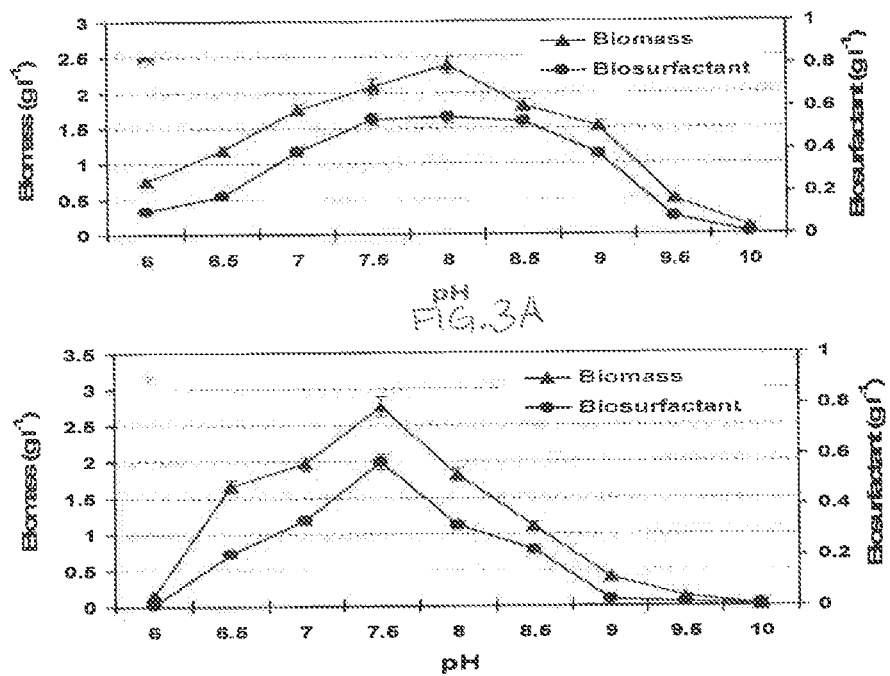
FIG. 3A
Figure 3B
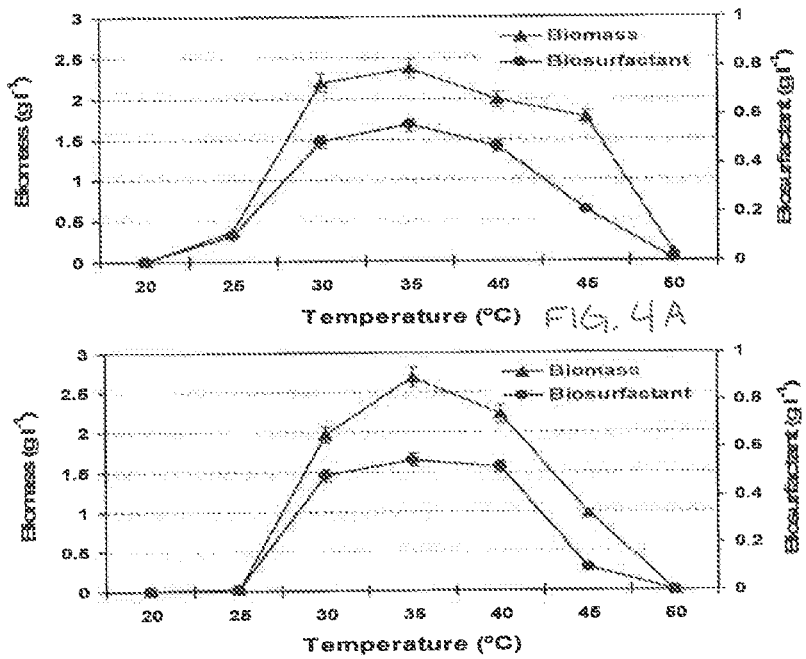
FIG. 4A
Figure 4B

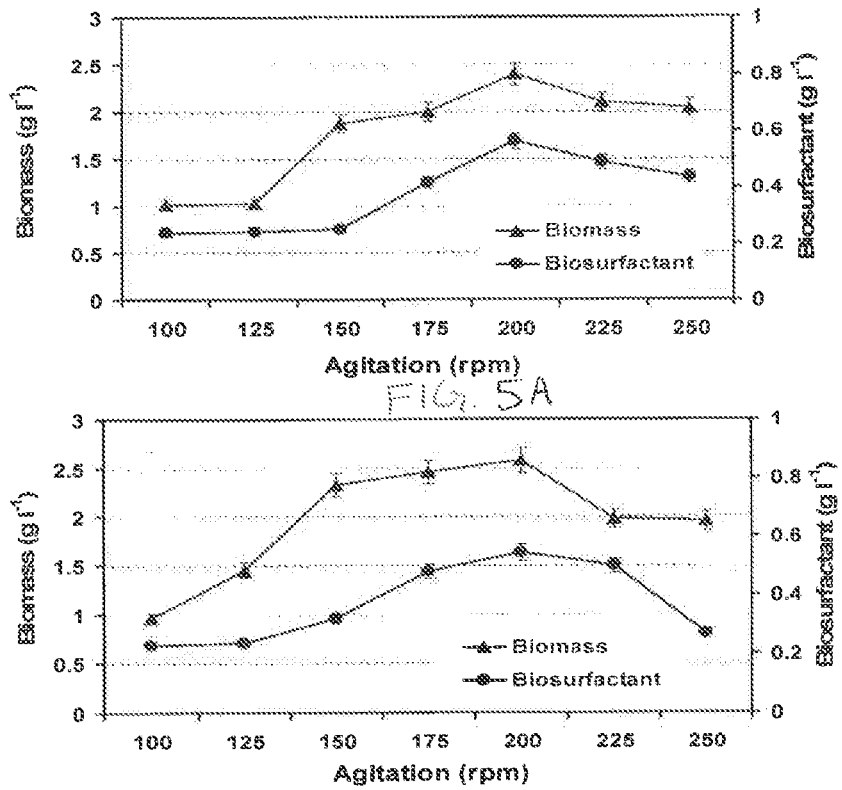
FIG. 5A
Figure 5B
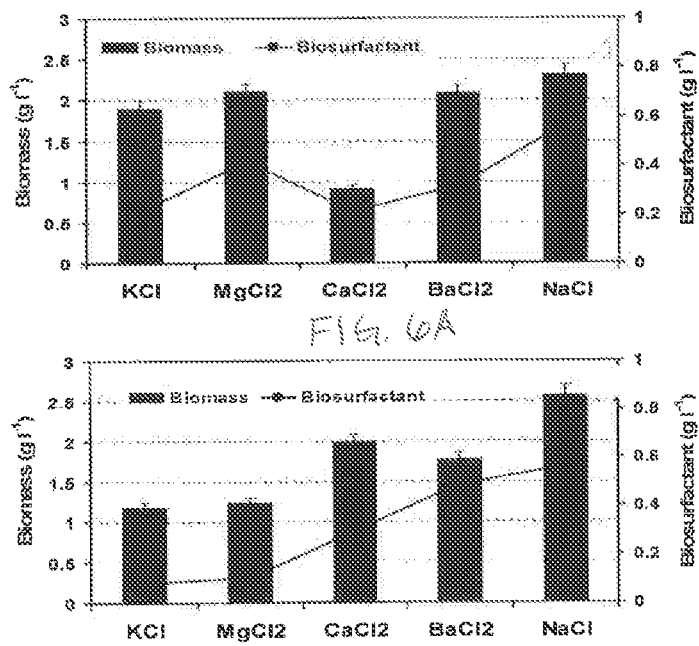
FIG. 6A
Figure 6B

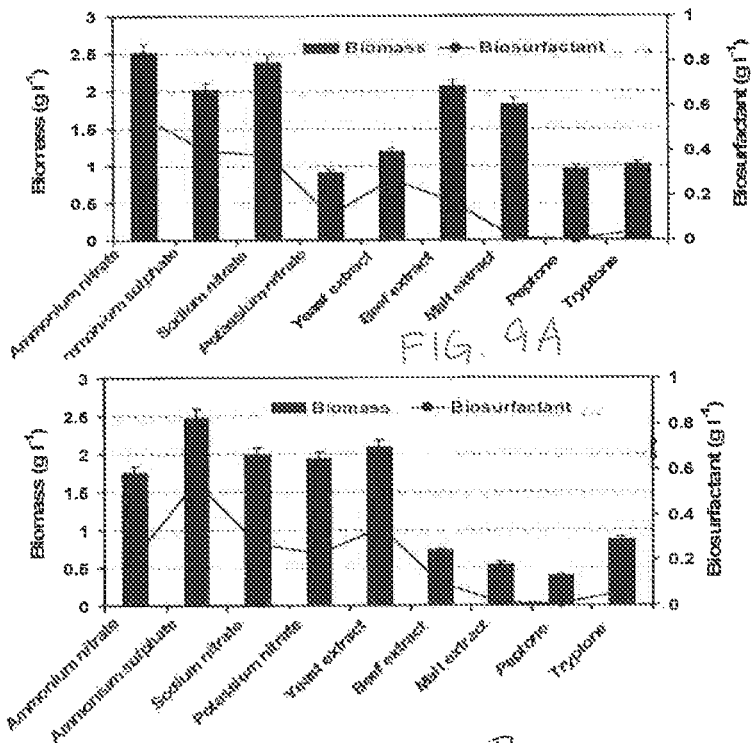
FIG. 9A
Figure 9B
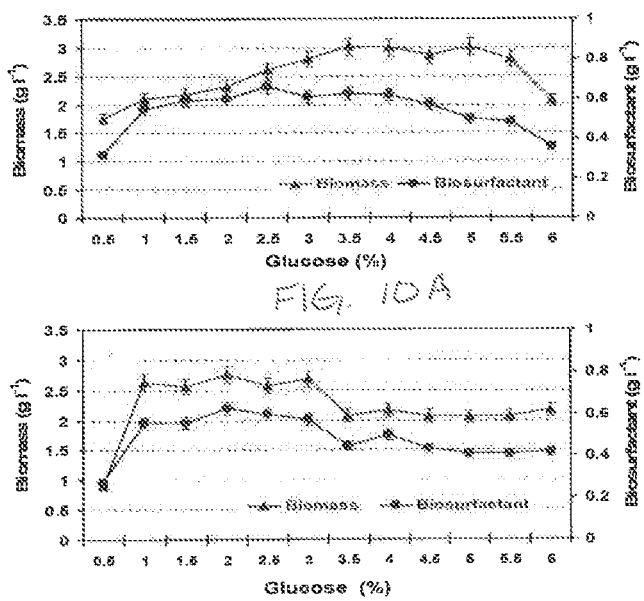
FIG. 10A
Figure 10B

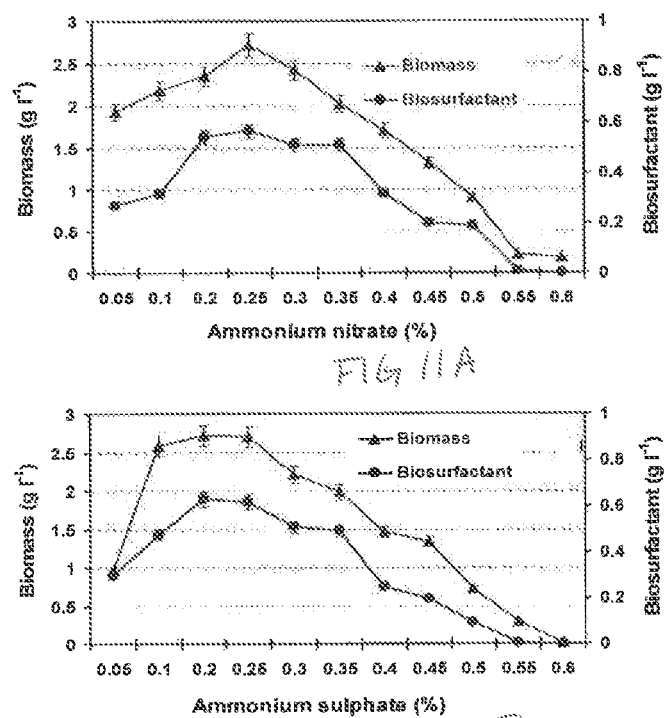
Figure 11A
Figure 11B
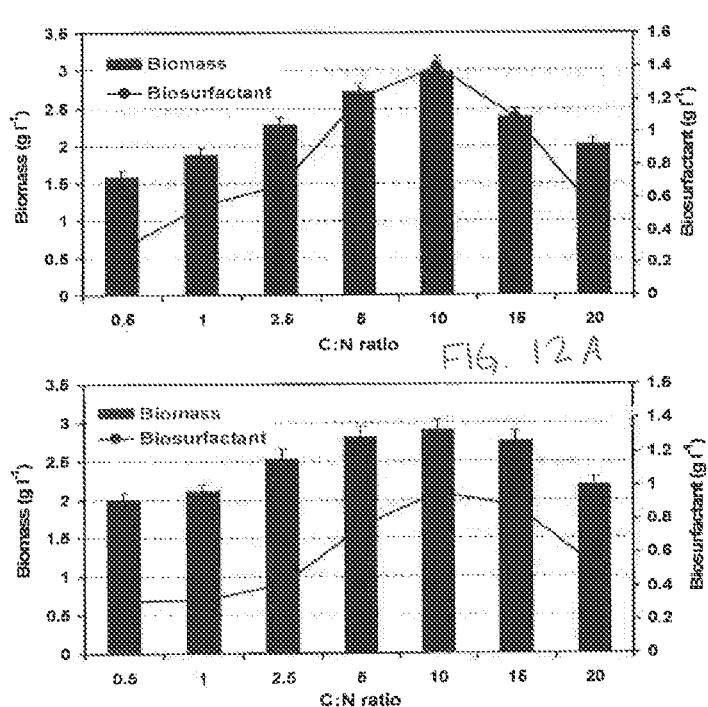
Figure 12A
Figure 12B

FIG 49A
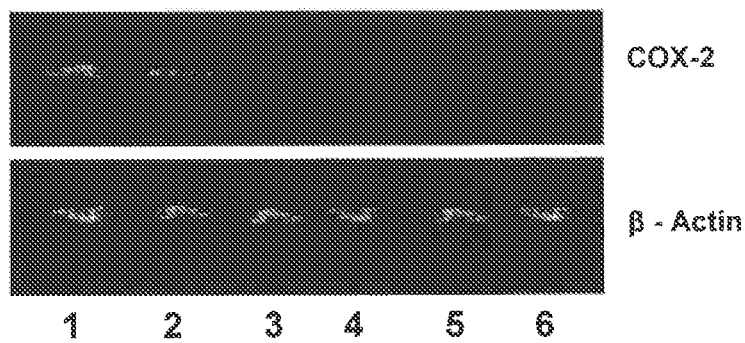
Lane 1: LPS (100 ng/ml)
Lane 2: Microsan (50 µg/ml)
Lane 3: M-EPS-Au-NP (50 µg/ml)
Lane 4: Microsan (10 µg/ml)
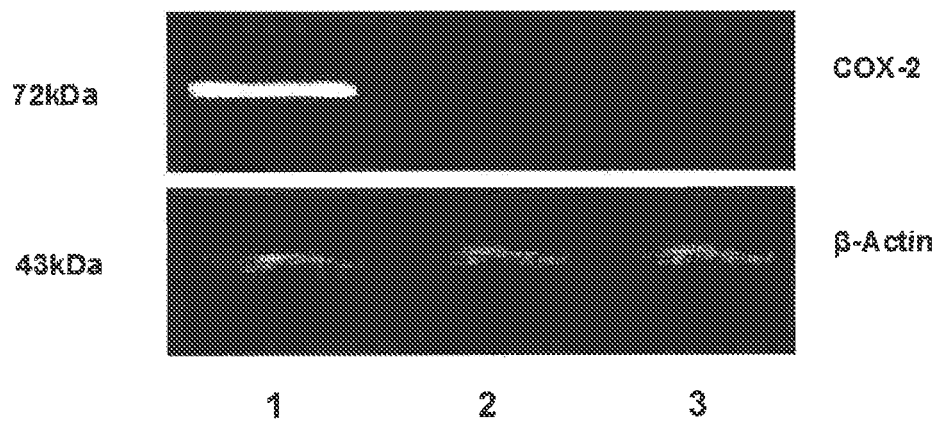
Lane 1: LPS (100 ng/ml)
Lane 2: Brevisan (20 µg/ml)
Figure 49B

PROCESS FOR THE PREPARATION OF POLYMERIC BIOSURFACTANTS

PRIORITY CLAIM

This patent application claims priority to Indian Patent Application No. 939/DEP/2014, filed 1 Apr. 2014, the disclosure of which is incorporated herein by reference in its entirety.

FIELD OF THE INVENTION

The present invention relates to polymeric biosurfactants isolated from two bacterial strains of Microbacterium sp. strain BS-2 [MTCC 5822] and Brevibacillus sp. strain BS-207 [MTCC 5823]. Particularly, the present invention relates to an acidic exopolysaccharide (EPS), termed Microsan, with chemical composition of glucose, mannose and glucuronic acid (β-D-glucuronyl-(1-2)-D-mannosyl-(1-4)-D-glucose) produced by Microbacterium sp. strain BS-2 and a neutral EPS, termed Brevisan, of galactomannan with galactose and mannose residues in the ratio of 1:1 produced by Brevibacillus sp. strain BS-207. Both these polysaccharides exhibited surface-active and potential antioxidant activities. Further, the invention relates to the synthesis of gold nanoparticles using Microsan from Microbacterium (M-EPS).

BACKGROUND OF THE INVENTION

Biosurfactants are biodegradable amphiphilic molecules produced by several microbes that have excellent surface tension lowering activity and act as excellent emulsifiers, foaming and dispersing agents [Desai, J. D. and Banat, I. M. (1997) Microbiol. Mol. Biol. Rev. 61, 47-64]. These compounds are produced extracellular with potential applications in agriculture, cosmetics, pharmaceuticals, detergents, food processing, paint industry and others [Banat, I. M. (1995) Biores. Technol. 51, 1-12]. These surface-active agents are chemically diversified from low molecular weight glycolipids, lipopeptides/lipoproteins and phospholipids to high molecular weight neutral lipids, substituted fatty acids and polysaccharides [Cooper, D. G. and Zajic, J. E. (1980) Appl. Environ. Microbiol. 26, 229-256]. The microbial exopolysaccharides (EPS) with novel chemical structures offer a number of applications in food, pharmaceutical, textile, cosmetics, microbial ecology, medicine, dairy industry, biofilms, corrosion, etc. due to their rheological properties [Nicolaus, B. Kambourova, M. and Oner, E. T. (2010) Environ. Technol. 31, 1145-1158]. Some of the bacterial EPS that have found diverse range of applications are the xanthan (Xanthomonas campestris), dextran (Leuconostoc mesentroides), alginate (Pseudomonas aeruginosa and Azotobacter vinelandii), emulsan (Acinetobacter calcoaceticus), gellan (Sphingomonas paucimobilis), bacterial cellulose (Acetobacter xylinum), curdlan (Rhizobium meliloli and Agrobacterium radiobacter), succinoglycan (Alcaligenes faecalis var. myxogenes) and hyaluronic acid (Streptococcus zooepidemicus and Streptococcus equi) [Kumar, A. S., Mody, K. and Jha, B. (2007) J. Basic Microbiol. 47, 103-117]. Further, several biologically active polysaccharides such as krestin from Trametes versicolor, hetero-β-glucans from Agaricus blazei, lentinan from Lentinus edodes, and schizophyllan from Schizophyllum commune are well documented [Novak, M. and Vetvicka, V. (2008) J. Immunotoxicol. 5, 47-57]. They exhibit a diverse range of biological activities including hypoglycemic, anti-inflammatory, anti-tumor, anti-metastasis, hypolipidemic, immunomodulatory and antioxidant effects [Wasser, S. P. (2002) Appl. Microbiol. Biotechnol. 60, 258-274; Lee, H. H., Lee, J. S., Cho, J. Y., Kim, Y. E. and Hong, E. K. (2009) J. Microbiol. Biotechnol. 19, 566-572].

Macrophages play a key role in innate and adaptive immune system and are also involved in mounting an inflammatory response [Beutler, B. (2004). Mol. Immunol. 40, 845-859]. The activated macrophages release inflammatory mediators such as NO, TNF-α, IL-1β and IL-6 that regulate homeostasis under physiological conditions, while unregulated release was observed in several pathological conditions [Micking, J., Xie, Q. W. and Nathan, C. (1997) Annu. Rev. Immunol. 15, 323-350]. The impaired macrophage activation was observed under several pathological conditions such as septic shock, cerebral injury, myocardial ischemia, local or systemic inflammatory disorders, diabetes and other diseases. Hence, the modulation of macrophage activity is of central importance. Some microbial polysaccharides such as hetero-β-glucans extracted from fruiting bodies of Agaricus blazei exhibited immunomodulating properties [Cho, S. M., Park, J. S., Kim, K. P., Cha, D. Y., Kim, H. M. and Yoo, I. D. (1999) Korean J. Mycol. 27, 170-174]. Published reports on EPS demonstrated that they can scavenge ROS exhibiting potential antioxidant activities [Sun, C., Wang, J. W., Fang, L., Gao, X.-D. and Tan, R.-X. (2004) Life Sci. 75, 1063-1073] as well as immunostimulant activities on macrophages [Lee, H. H., Lee, J. S., Cho, J. Y., Kim, Y. E. and Hong, E. K. (2009a) J. Microbiol. Biotechnol. 19, 566-572; Lee, J. S., Min, K. M., Cho, J. Y. and Hong, E. K. (2009b) J. Microbiol. Biotechnol. 19, 951-959]. The upregulated ROS and RNS are involved in several pathological conditions and are known to cause oxidative damage to cell membrane, proteins, DNA and lipid molecules [Medzhitov, R. and Janeway, C. (2000) Immunol. Rev. 173, 89-97]. This oxidative stress induces the upregulation of transcriptional factors which in turn upregulates various proinflammatory molecules in macrophages thereby regulating various aspects of immune system [Brown, D. M., Donaldson, K., Borm, P. J., Schins, R. P., Dehnhardt, M., Gilmour, P. Jimenez, L. A. and Stone, V. (2004) Am. J. Physiol. Lung Cell Mol. Physiol. 286, L344-353].

Some Microbacterium species are reported to produce EPS. The EPS production by most of the family members of the genus Microbacterium has not been fully understood, nevertheless both homo- and hetero-types of biopolymers with glucose, mannose and fructose backbone have been reported [Bae, I. Y., Oh, I.-K., Lee, S., Yoo, S.-H. and Lee, H. G. (2008) Int. J. Biol. Macromol. 42, 10-13; Asker, M. M. S., Ahmed, Y. M. and Ramdan, M. F. (2009) Carbohydr. Polym. 77, 563-567; Godinho, A. L. and Bhosle, S. (2009) Curr. Microbiol. 58, 616-621]. Microbacterium kitamiense strain Kitami C2, isolated from the wastewater of a sugar-beet factory was reported to produce EPS [Matsuyama, H., Kawasaki, K., Yumoto, I. and Shida, O. (1999) Int. J. Syst. Bacteriol. 49, 1353-1357]. Microbacterium strain MC3B-10, isolated from the tropical intertidal rocky shore in southern Gulf of Mexico (Campeche, Mexico), produced a polymer which was not a polysaccharide but a glycoprotein with surfactant properties. This glycoprotein was rich in protein (36%) and had low levels of neutral sugars [Ortega-Morales, B. O., Santiago-Garcia, J. L., Chan-Bacab, M. J., Moppert, X., Miranda-Tello, E., Fardeau, M. L., Carrero, J. C., Bartolo-Pérez, P., Valadéz-González, A. and Guezennec, J. (2007) J. Appl. Microbiol. 102, 254-264]. Microbacterium lerregens produced an EPS exhibiting antioxidant activity with an $IC_{50}$ value of 230 µg mL$^{-1}$ [Asker, M. M. S., Ahmed, Y. M. and Ramdan, M. F. (2009) *Carbohydr. Polym.* 77, 563-567]. *Microbacterium arborescens* strain AGSB, isolated from the rhizosphere of *Ipomoea pescaprae*, produced a mannose-based heteropolysaccharide, which had the ability to aggregate sand and improve the moisture-holding capacity [Godinho, A. L. and Bhosle, S. (2009) *Curr. Microbiol.* 58, 616-621]. *Microbacterium* sp. strain Mc1, isolated from mangrove sediment, produced a bioemulsifier which had the ability to remove cadmium and zinc from a hazardous industrial waste [Aniszewski, E., Peixoto, R. S., Mota, F. F., Leite, S. G. F. and Rosado, A. S. (2010) *Brazilian J. Microbiol.* 41, 235-245].

Very few strains of *Brevibacillus* sp. are reported to produce biosurfactants. *Brevibacillus brevis* HOB1 produced a lipopeptide with antibacterial and antifungal activities [Haddad, N. I. A., Wang, J. and Mu, B. (2008) *J. Ind. Microbiol. Biolechnol.* 35, 1597-1604], while *Brevibacterium* sp. strain PDM-3 produced a biosurfactant that finds application in the bioremediation of phenanthrene and polyaromatic hydrocarbons like anthracene and fluorine [Reddy, M. S., Naresh, B., Leela, T., Prashanthi, M., Madhusudhan, N. C., Dhanasri, G. and Devi, P. (2010) *Biores. Technol.* 101, 7980-7983]. *Brevibacterium* sp. 7G isolated from a crude oil-contaminated soil also produced a glycolipid biosurfactant [Ferhat, S., Mnif, S., Badis, A., Eddouaouda, K., Alouaoui, R., Boucherit, A., Mhiri, N., Moulai-Mostefa, N. and Sayadi, S. (2011) *International Biodeterioration and Biodegradation* 65, 1182-1188]. There is paucity of information on EPS producers from *Brevibacterium* sp., except one report on *Brevibacillus thermoruber* strain 438 producing EPS [Radchenkova, N., Tomova, A. and Kambourova, M. (2011) *Biotechnol. Biotechnol. Eq.* 25, 77-79]. Recently, two new bacterial strains of *Microbacterium* sp. BS-2 and *Brevibacillus* sp. strain BS-207 were identified based on 16S rDNA sequencing. The 16s rDNA sequences have been deposited in GenBank database with accession numbers, HQ116802 and HQ116803, respectively [Kumar, C. G., Mamidyala, S. K., Sujitha, P., Muluka, H. and Akkenapally, S. (2012) *Biotechnol. Prog.* 28, 1507-1516].

In view of the above facts, there is an urgent need to identify new and potential biosurfactants that exhibit surface tension lowering activity and other biological properties. The present invention fulfils these requirements as it provides two new bacterial strains of *Microbacterium* sp. strain BS-2 and *Brevibacillus* sp. strain BS-207 producing polymeric biosurfactants that has antimicrobial, antioxidant, anti-inflammatory and immunomodulating properties and acted as potential immunosuppressive agents.

SUMMARY

Disclosed embodiments provide polymeric exopolysaccharide biosurfactants from two novel bacterial strains of *Microbacterium* sp. strain BS-2 and *Brevibacillus* sp. strain BS-207 (deposited with Microbial Type Culture Collection (MTCC), CSIR-Institute of Microbial Technology, Chandigarh, India with accession numbers MTCC 5822 and MTCC 5823).

Disclosed embodiments further provide a simple method for the isolation and purification of acidic and neutral polysaccharide-based biosurfactants from *Microbacterium* sp. BS-2 and *Brevibacillus* sp. BS-207, respectively.

Disclosed embodiments find use of these two polymeric biosurfactants as antioxidant agents.

Disclosed embodiments also find use of Microsan which has reducing and stabilizing properties and acted as capping ligands in the synthesis of gold nanoparticles (M-EPS-Au-NP).

Another objective of the present invention is to find use of Brevisan, Microsan and M-EPS-Au-NP as ROS inhibitors in LPS-stimulated RAW 264.7 macrophages.

Disclosed embodiments further find use of Brevisan, Microsan and M-EPS-Au-NP as anti-inflammatory agents to inhibit NO, TNF-α and IL-6 in LPS-stimulated RAW 264.7 macrophages.

Disclosed embodiments find use of Brevisan, Microsan and M-EPS-Au-NP to inhibit LPS-stimulated cyclooxygenase-2 in RAW 264.7 macrophages.

Disclosed embodiments describe the use of Microsan as a bactericidal agent.

Disclosed embodiments also find use of Brevisan to inhibit the production and hemolytic activity of C3 complement component in LPS-stimulated RAW 264.7 macrophages.

BRIEF DESCRIPTION OF THE TABLES AND FIGURES

Table 1 shows morphological, physiological and biochemical characteristics of *Microbacterium* sp. BS-2.

Table 2 shows morphological, physiological and biochemical characteristics of *Brevibacillus* sp. strain BS-207.

Table 3 shows antimicrobial activity of Microsan from *Microbacterium* sp. strain BS-2.

Table 4 shows alditol acetate derivatives of native and carboxyl reduced biosurfactant from *Microbacterium* sp. strain BS-2.

Table 5 shows alditol acetate derivatives of native and carboxyl reduced EPS produced from *Brevibacillus* sp. strain BS 207.

Table 6 shows alditol acetate derivatives of Lithium-ethylenediamine degraded biosurfactant from *Microbacterium* sp. strain BS-2.

Table 7 shows analysis of partially methylated alditol acetate derivatives of Lithium-ethylenediamine degraded EPS produced from *Brevibacillus* sp. strain BS-207.

FIG. 1A depicts scanning electron microscope (SEM) micrograph of *Microbacterium* sp. strain BS-2. *Microbacterium* sp. strain BS-2 [MTCC 5822] is Gram-positive; rod-shaped bacterium with parallel sides and rounded ends that did not produce any pigment on nutrient agar. The polymeric biosurfactant produced by the genus *Microbacterium* belongs to the family Microbacteriaceae of the order Actinomycetales.

FIG. 1B depicts scanning electron microscope (SEM) micrograph of *Brevibacillus* sp. strain BS-207. *Brevibacillus* sp. strain BS-207 [MTCC 5823] is Gram-positive; rod-shaped bacterium with parallel sides and rounded ends that does not produce any pigment on nutrient agar. It is strictly aerobic and spore-forming bacterium. The polymeric biosurfactant produced by the genus *Brevibacillus* belongs to the family Paenibacillaceae in the class Bacilli.

FIGS. 2A-B depicts growth kinetics profile of 2A *Microbacterium* sp. strain BS-2 and 2B *Brevibacillus* sp. strain BS-207 with reference to production of polymeric biosurfactants.

FIGS. 3A-3B depicts effect of pH on production of polymeric biosurfactants by 3A *Microbacterium* sp. strain BS-2 and 3B *Brevibacillus* sp. strain BS-207.

FIGS. 4A-4B depicts effect of temperature on production of polymeric biosurfactants by 4A *Microbacterium* sp. strain BS-2 and 4B *Brevibacillus* sp. strain BS-207.

FIGS. 5A-5B depicts effect of agitation on production of polymeric biosurfactants by 5A *Microbacterium* sp. strain BS-2 and 5B *Brevibacillus* sp. strain BS-207.

FIGS. 6A-6B depicts effect of different salts on production of polymeric biosurfactants by 6A *Microbacterium* sp. strain BS-2 and 6B *Brevibacillus* sp. strain BS-207.

FIGS. 9A-9B depicts effect of different nitrogen sources on production of polymeric biosurfactants by 9A *Microbacterium* sp. strain BS-2 and 9B *Brevibacillus* sp. strain BS-207.

FIGS. 10A-10B depicts effect of glucose concentration on production of polymeric biosurfactants by 10A *Microbacterium* sp. strain BS-2 and 10B *Brevibacillus* sp. strain BS-207.

FIGS. 11A-11B depicts effect of 11A ammonium nitrate concentration on polymeric biosurfactant production by *Microbacterium* sp. strain BS-2 and 11B ammonium sulphate concentration on polymeric biosurfactant production by *Brevibacillus* sp. strain BS-207

FIGS. 12A-12B depicts effect of C:N ratio on production of polymeric biosurfactants by 12A *Microbacterium* sp. strain BS-2 and 12B *Brevibacillus* sp. strain BS-207.

Figure 13A:
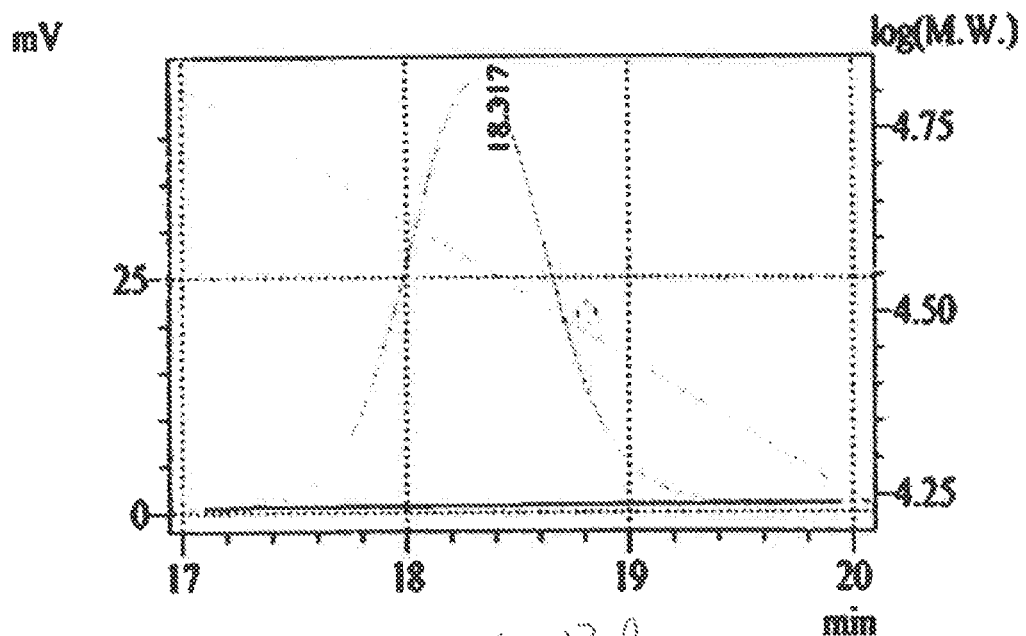
Figure 13B:
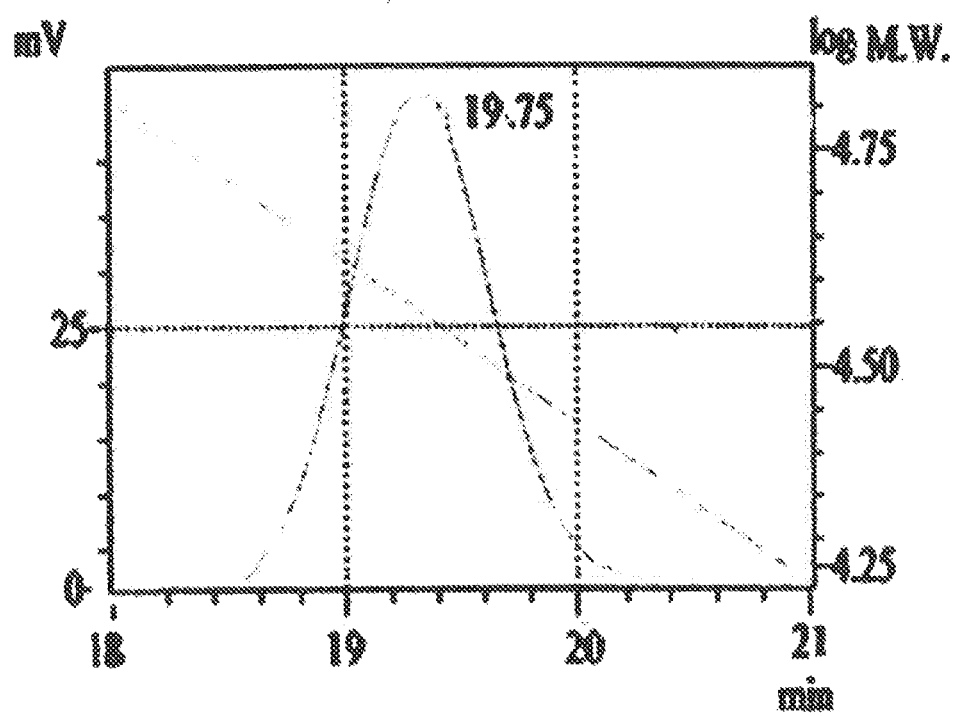

FIG. 13s 13A-13B depicts gel permeation chromatograms of polymeric biosurfactants produced by 13A *Microbacterium* sp. strain BS-2 and 13B *Brevibacillus* sp. strain BS-207.

Figure 14A:
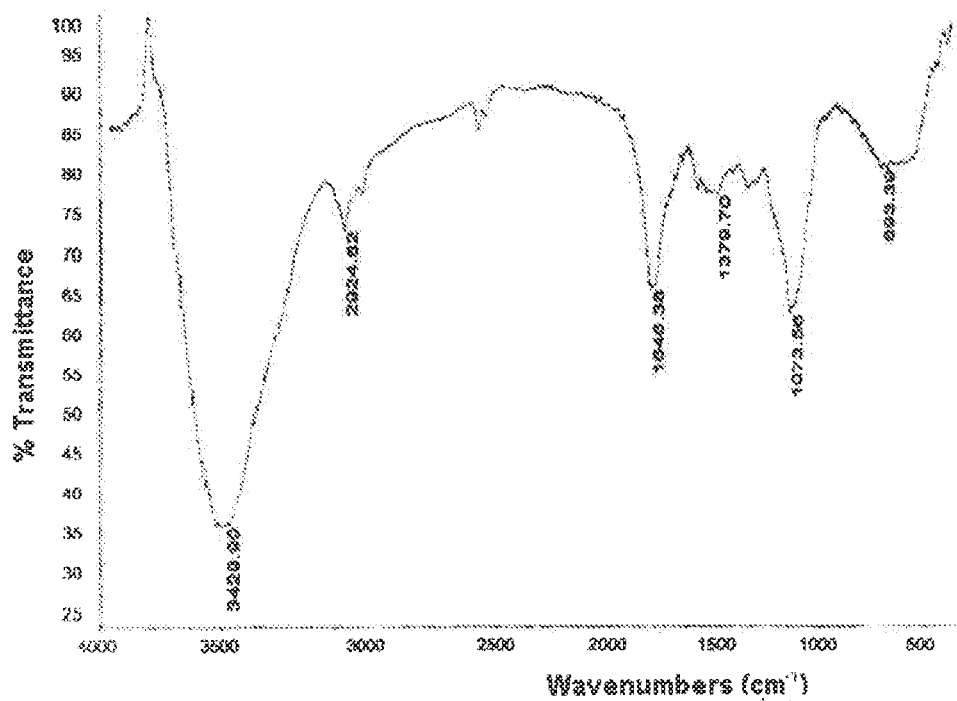
Figure 14B:
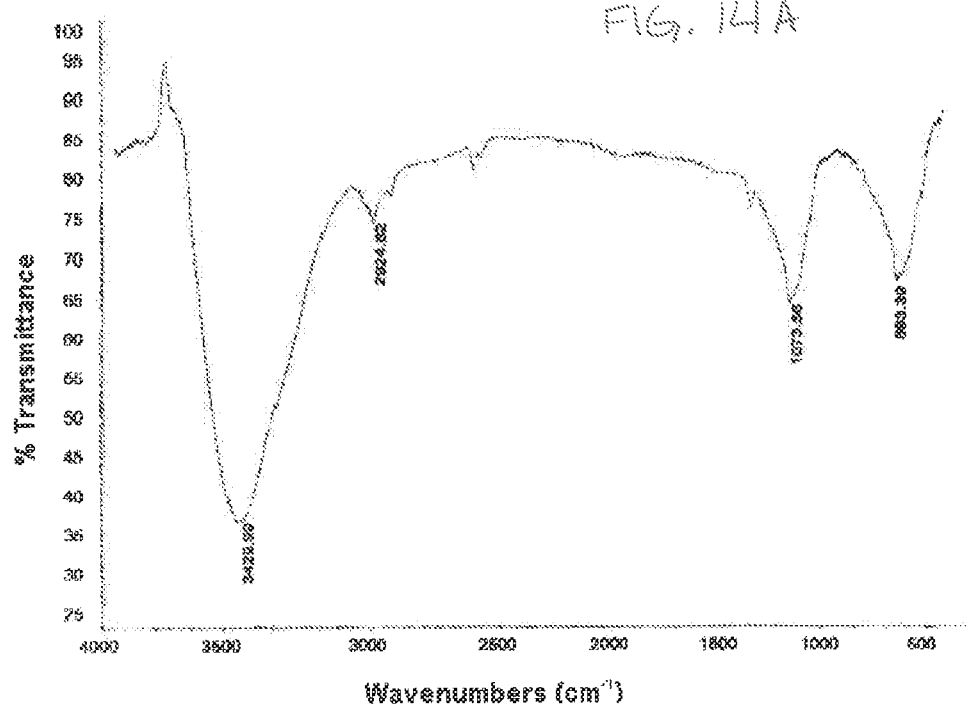

FIGS. 14A-14B depicts FT-IR spectra of polymeric biosurfactants produced by 14A *Microbacterium* sp. strain BS-2 and 14B *Brevibacillus* sp. strain BS-207.

Figure 15A:
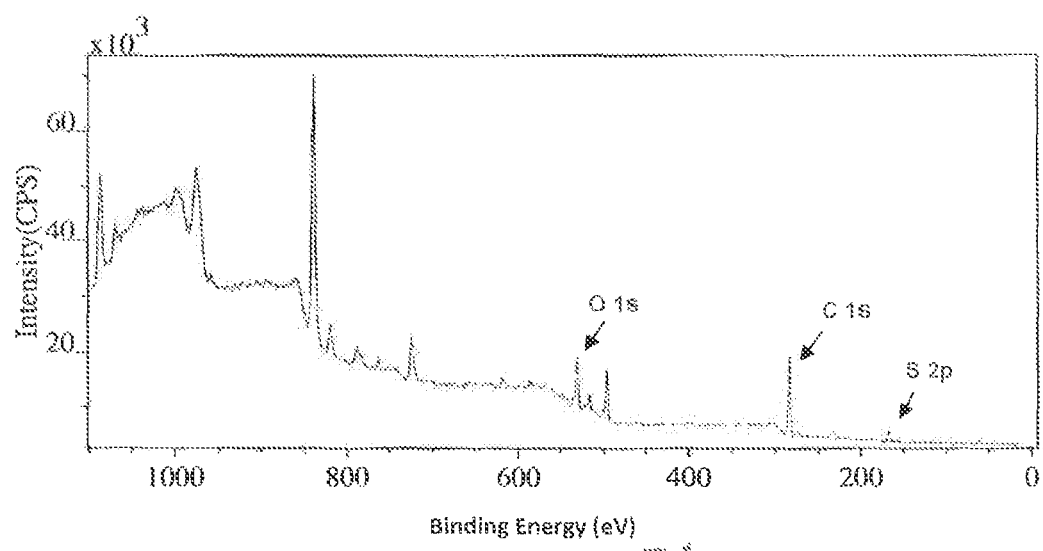
Figure 15B:
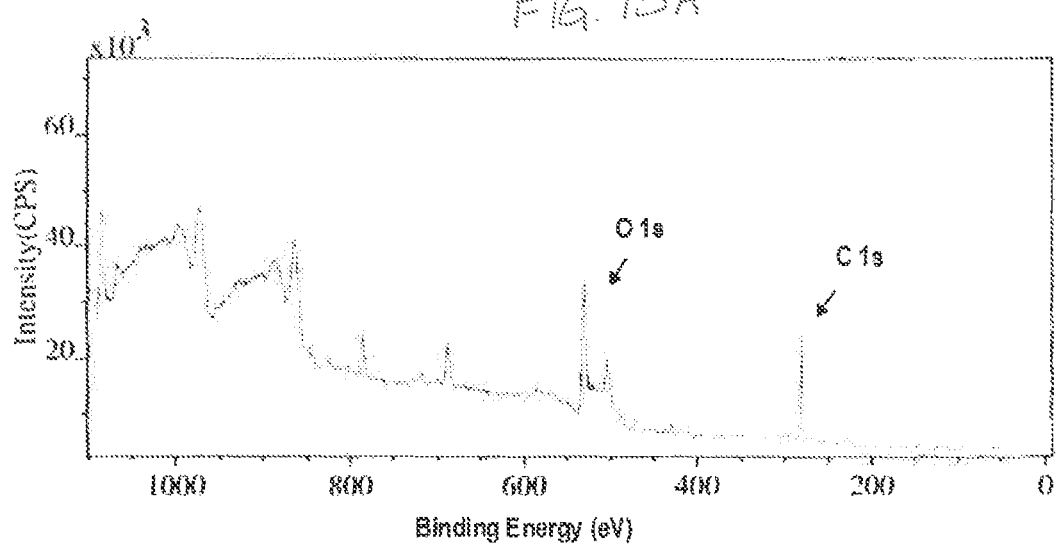

FIGS. 15A-15B depicts X-ray photoelectron spectra of polymeric biosurfactants produced by 15A *Microbacterium* sp. strain BS-2 and 15B *Brevibacillus* sp. strain BS-207.

Figure 16A:
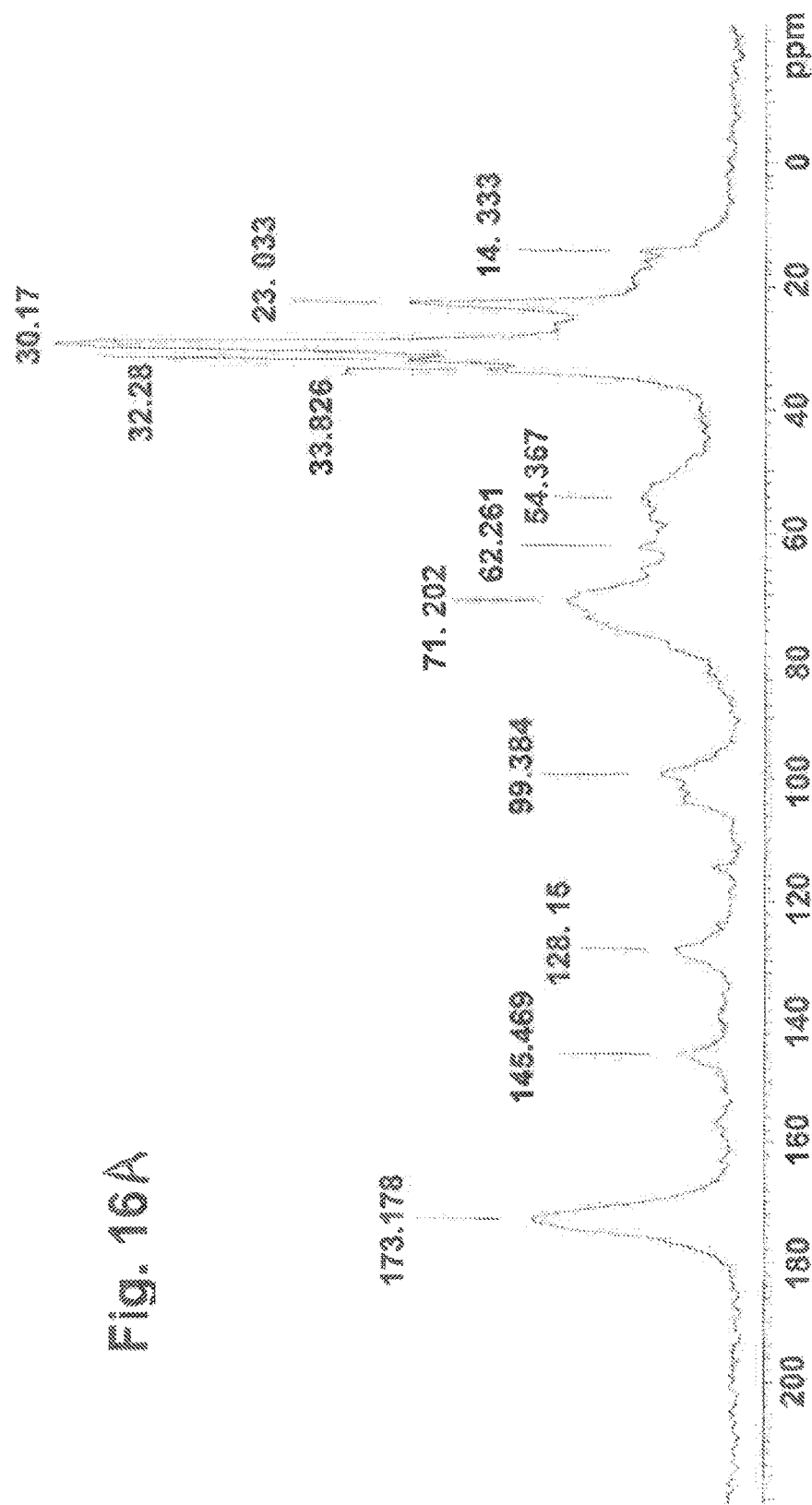
Figure 16B:
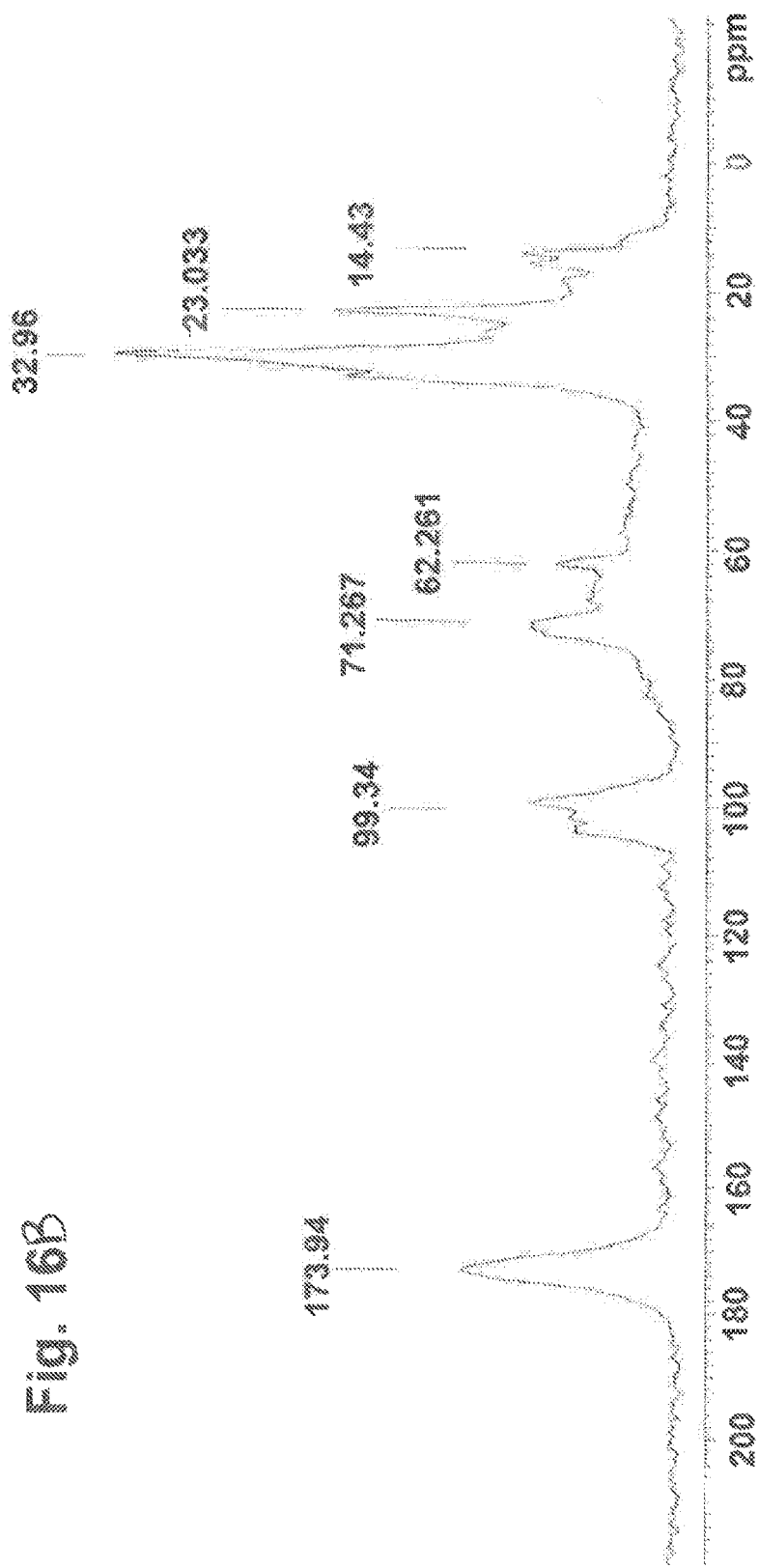

FIGS. 16A-16B depicts CP/MAS $^{13}$C NMR spectra of polymeric biosurfactants from 16A *Microbacterium* sp. strain BS-2 and 16B *Brevibacillus* sp. strain BS-207.

Figure 17A:
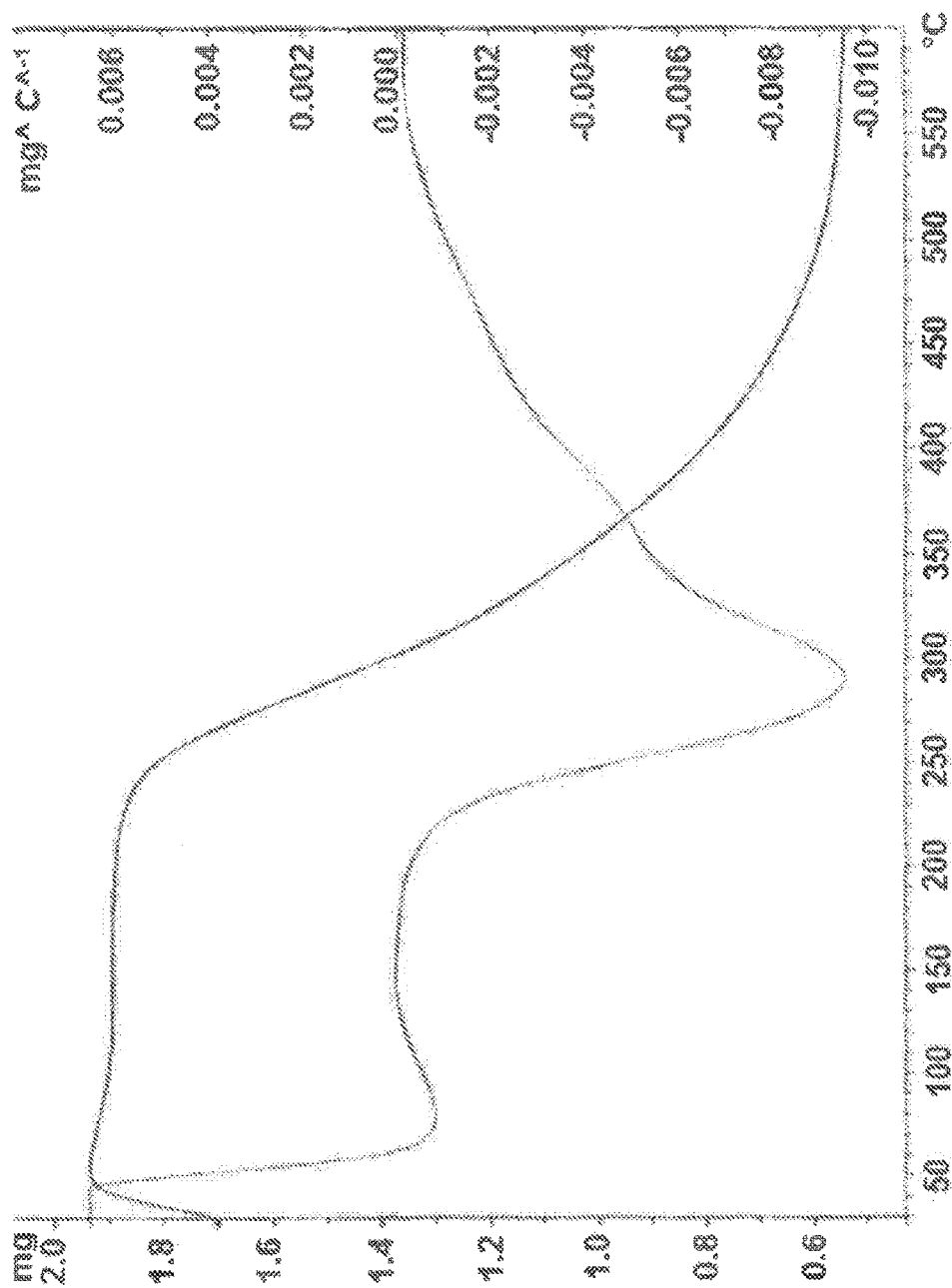
Figure 17B:
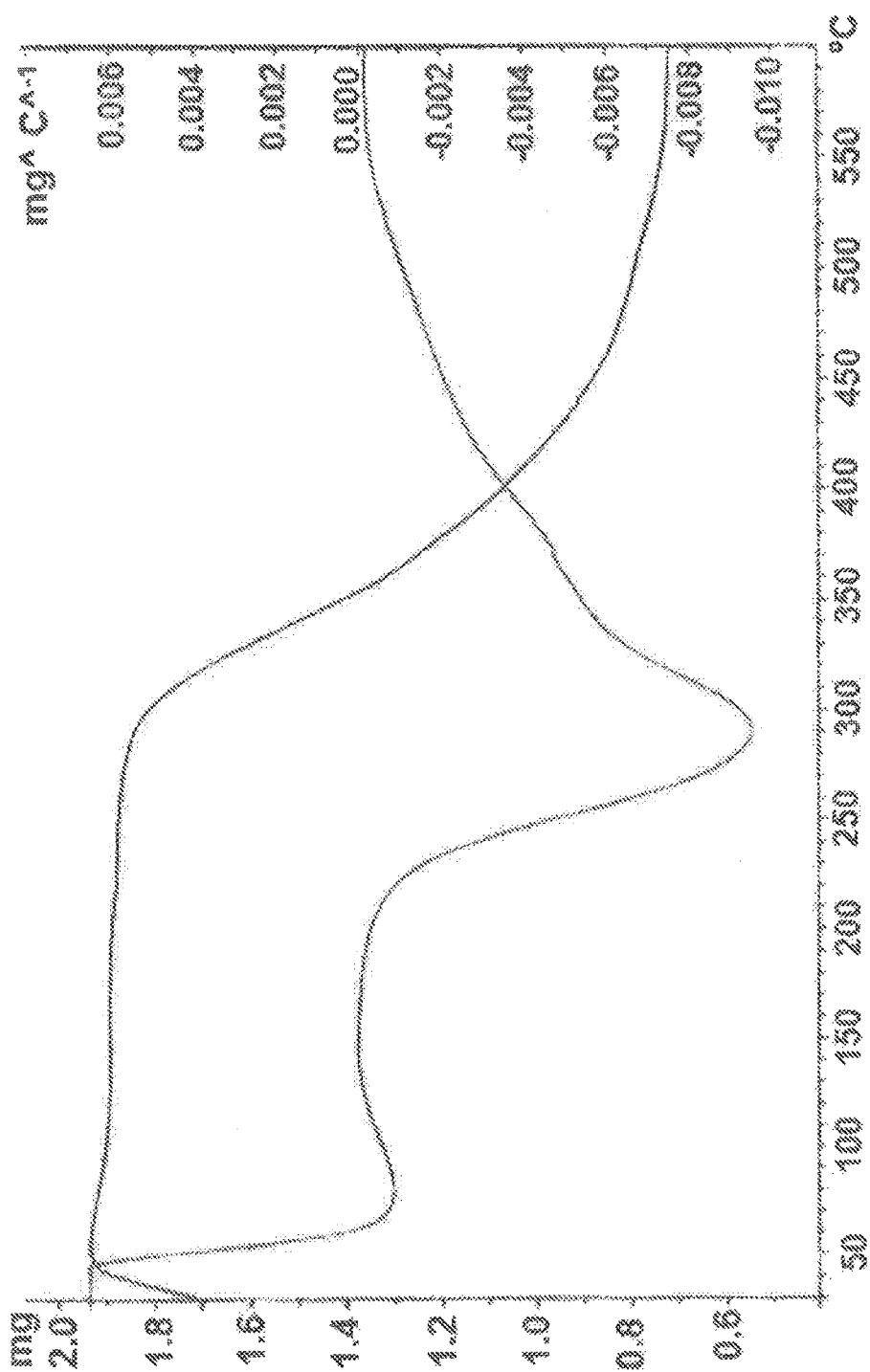

FIGS. 17A-17B depicts Thermograms of polymeric biosurfactants produced by 17A *Microbacterium* sp. strain BS-2 and 17B *Brevibacillus* sp. strain BS-207.

Figure 18A:
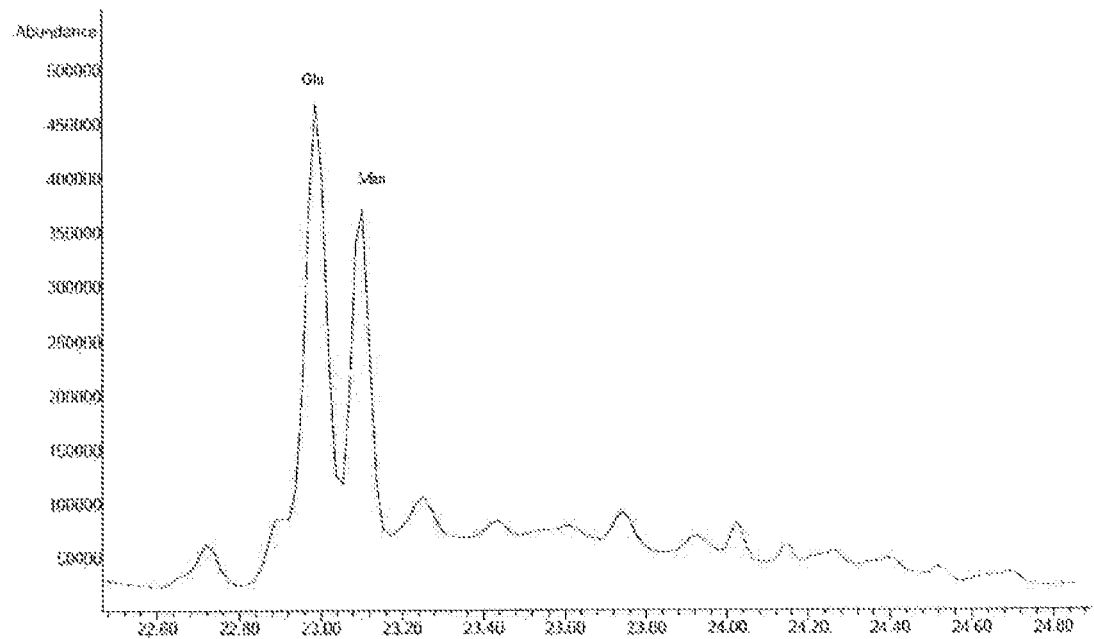
Figure 18B:
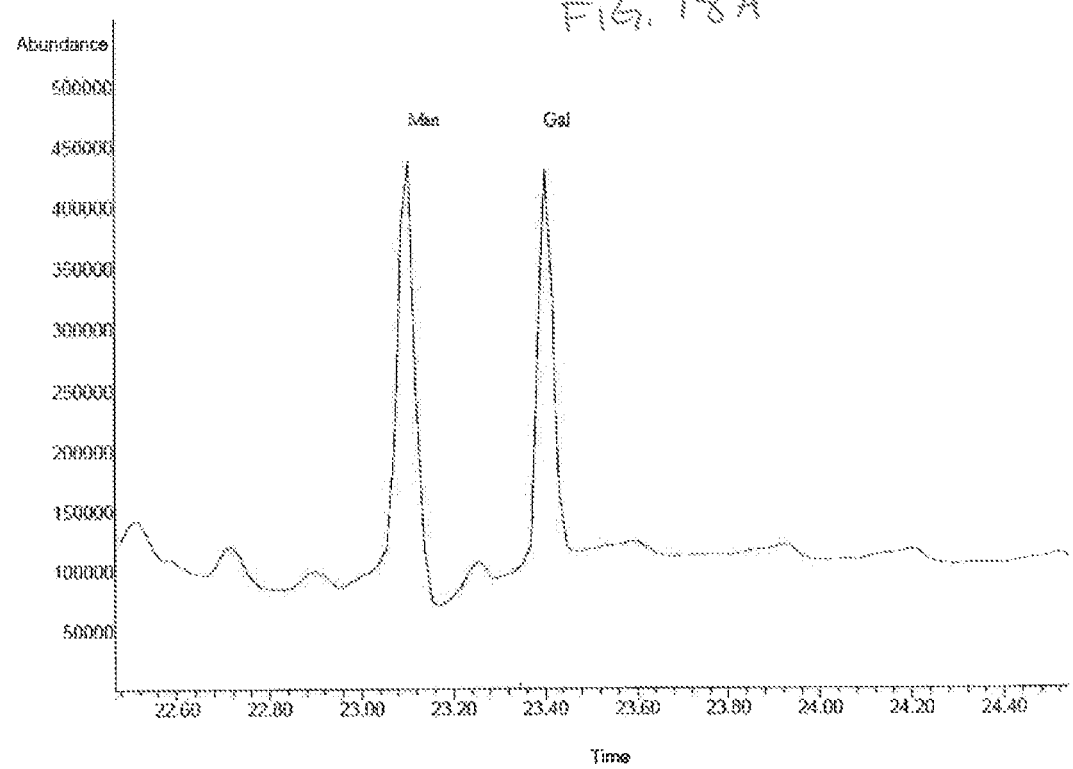

FIGS. 18A-18B depicts monosaccharide analysis of polymeric biosurfactants produced by 18A *Microbacterium* sp. strain BS-2 and 18B *Brevibacillus* sp. strain BS-207.

Figure 19A:
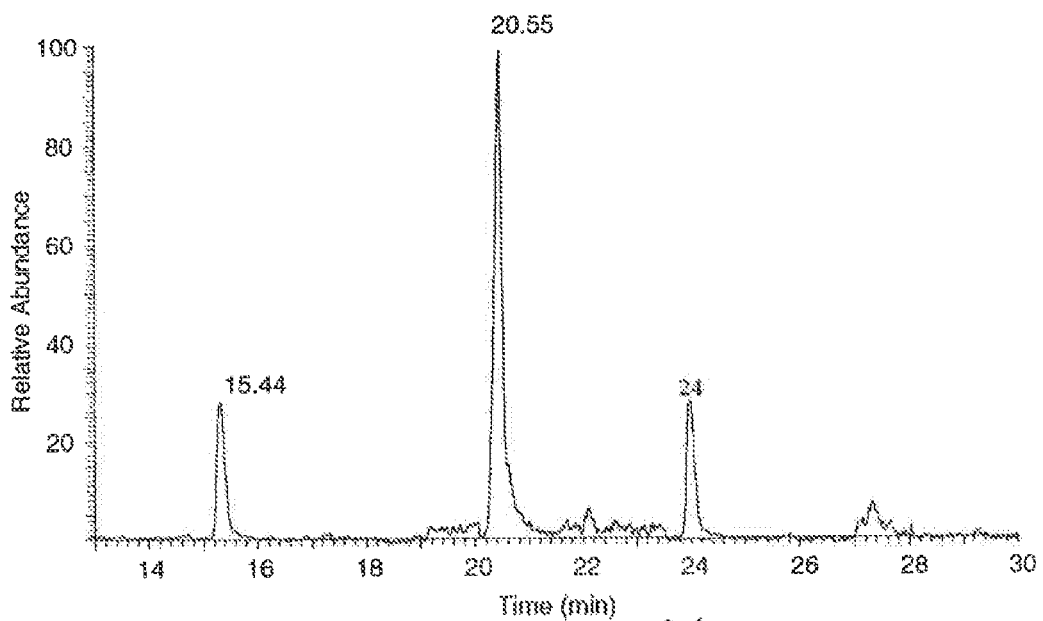
Figure 19B:
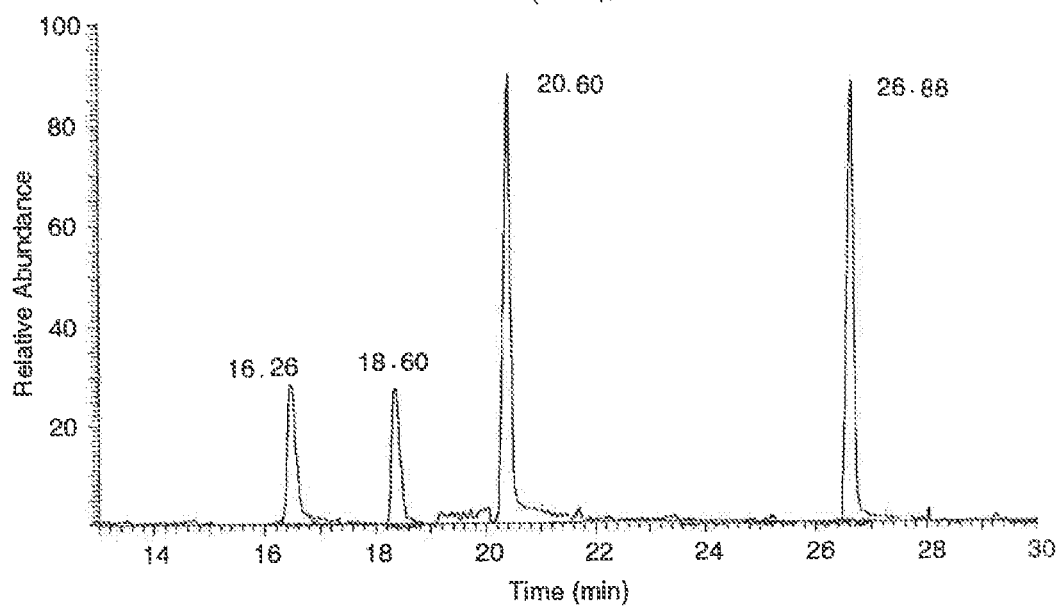

FIGS. 19A-19B depicts GC analysis of partially methylated alditol acetates of native polymeric biosurfactants produced by 19A *Microbacterium* sp. strain BS-2 and 19B *Brevibacillus* sp. strain BS-207.

Figure 20A:
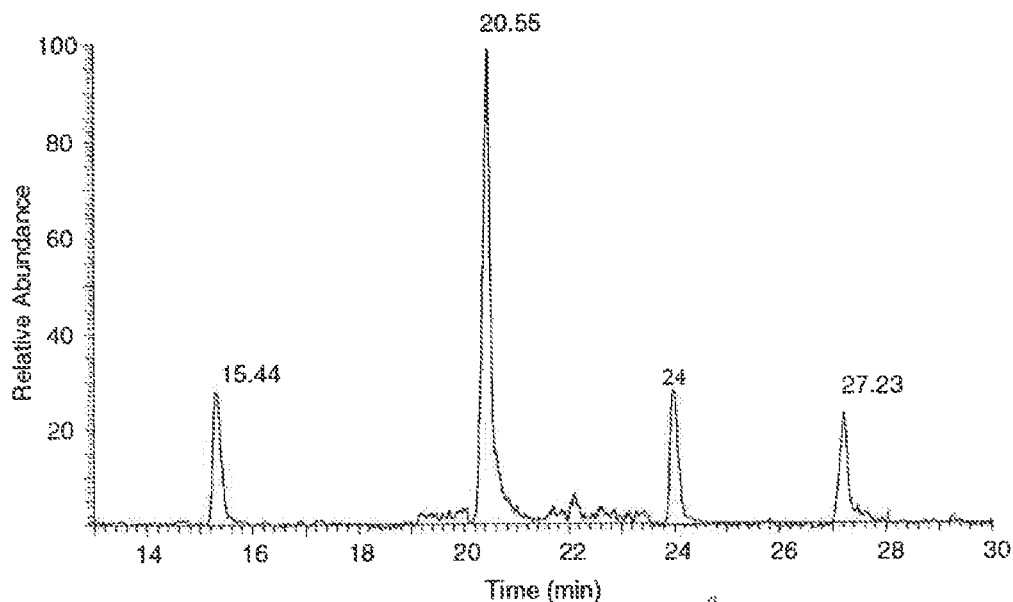
Figure 20B:
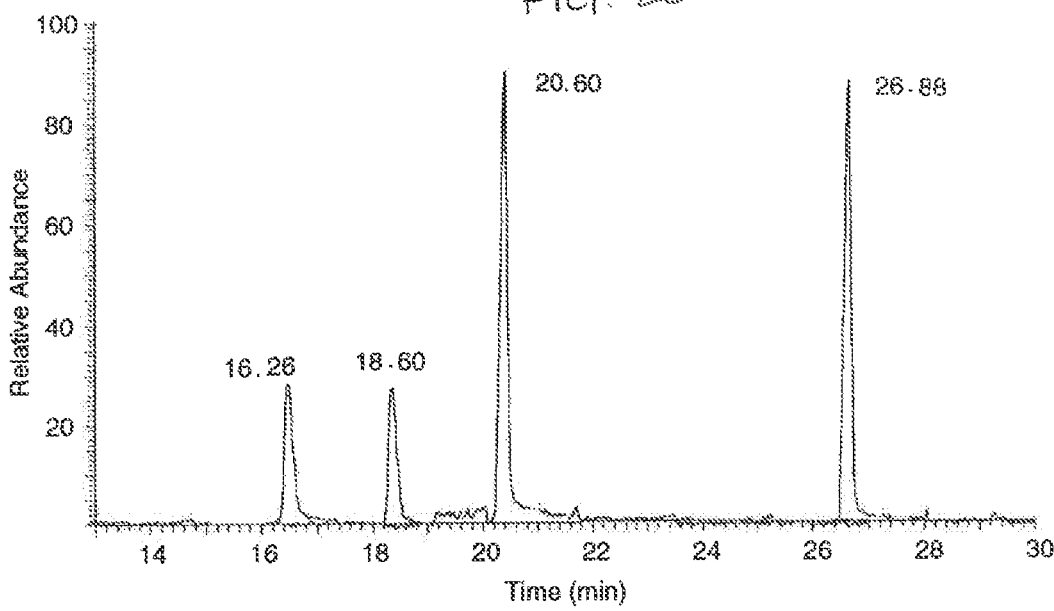

FIGS. 20A-20B depicts GC analysis of partially methylated alditol acetates of carboxyl reduced polymeric biosurfactants produced by 20A *Microbacterium* sp. strain BS-2 and 20B *Brevibacillus* sp. strain BS-207.

Figure 21A:
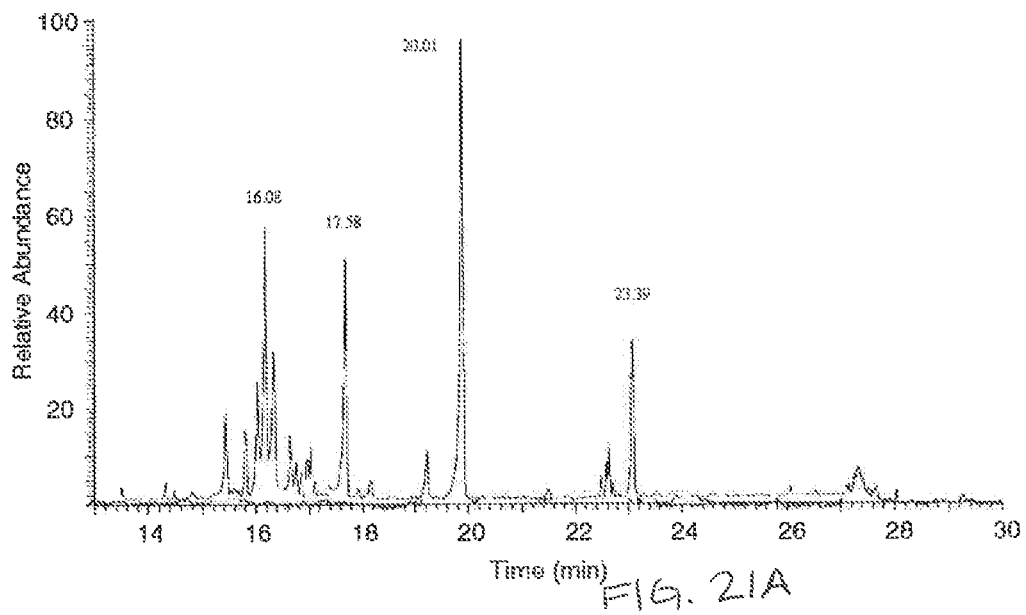
Figure 21B:
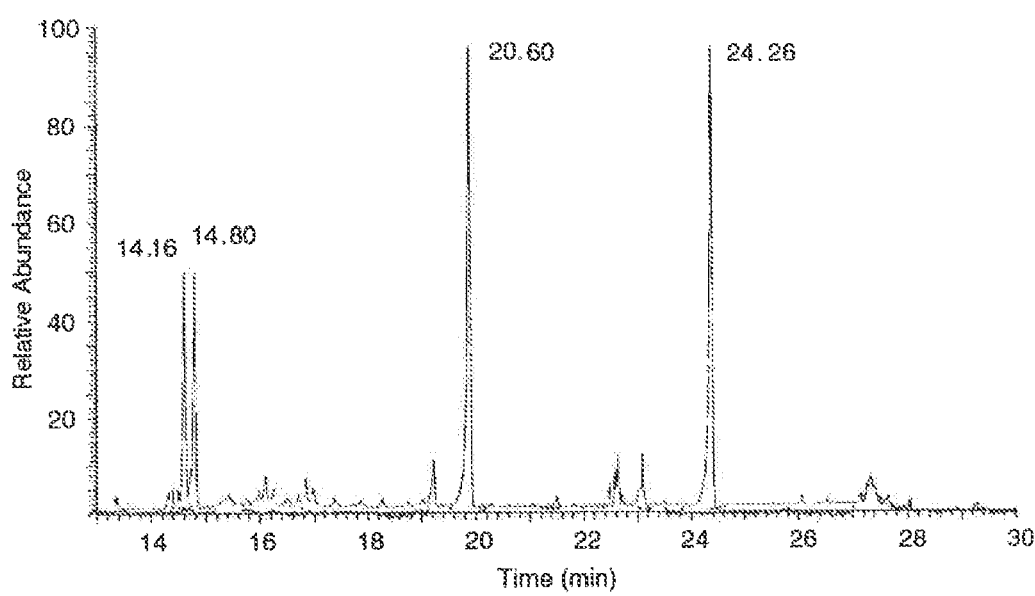

FIGS. 21A-21B depicts GC analysis of partially methylated alditol acetates of Lithium-ethylenediamine degraded polymeric biosurfactants produced by 21A *Microbacterium* sp. strain BS-2 and 21B *Brevibacillus* sp. strain BS-207.

Figure 22:
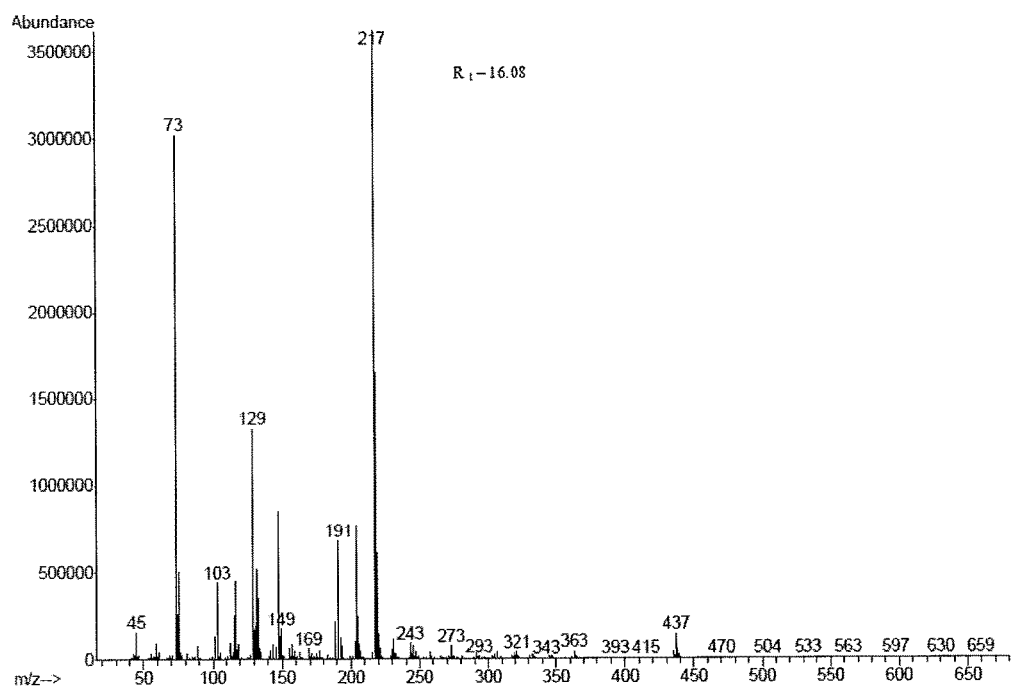

FIG. 22 depicts GC-MS analysis of 1,5-di-O-acetyl-2,3,4,6-tetra-O-methyl-D-glucitol derivative of alditol acetates of Lithium-ethylenediamine degraded polymeric biosurfactant produced by *Microbacterium* sp. strain BS-2.

Figure 23:
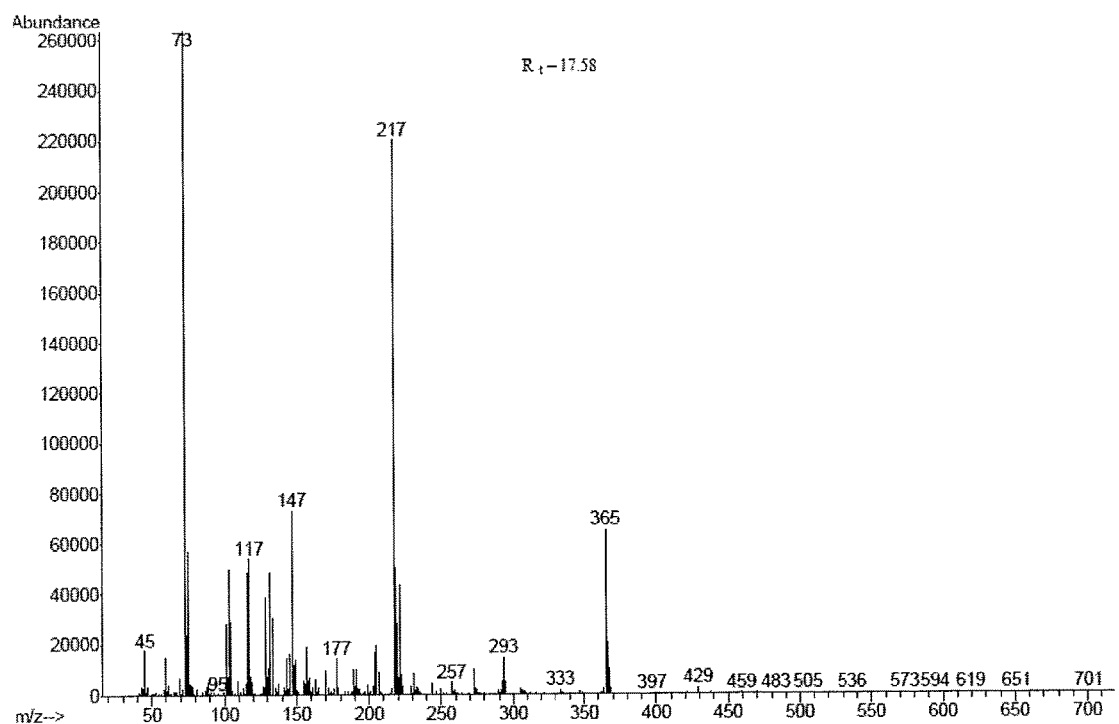

FIG. 23 depicts GC-MS analysis of 1,4,5-tri-O-acetyl-2,3,6-tri-O-methyl-D-glucitol derivative of alditol acetates of Lithium-ethylenediamine degraded polymeric biosurfactant produced by *Microbacterium* sp. strain BS-2.

Figure 24:
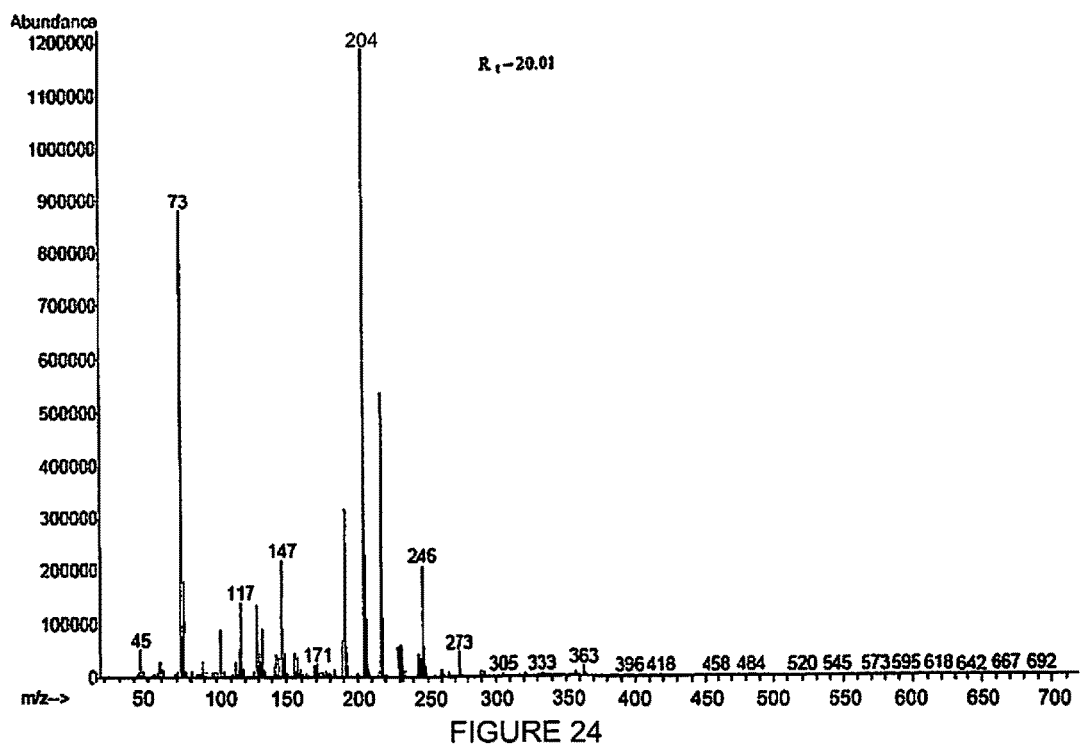

FIG. 24 depicts GC-MS analysis of 1,2,4,5-tetra-O-acetyl-3,6-di-O-methyl-D-mannitol derivative of alditol acetates of Lithium-ethylenediamine degraded polymeric biosurfactant produced by *Microbacterium* sp. strain BS-2.

Figure 25:
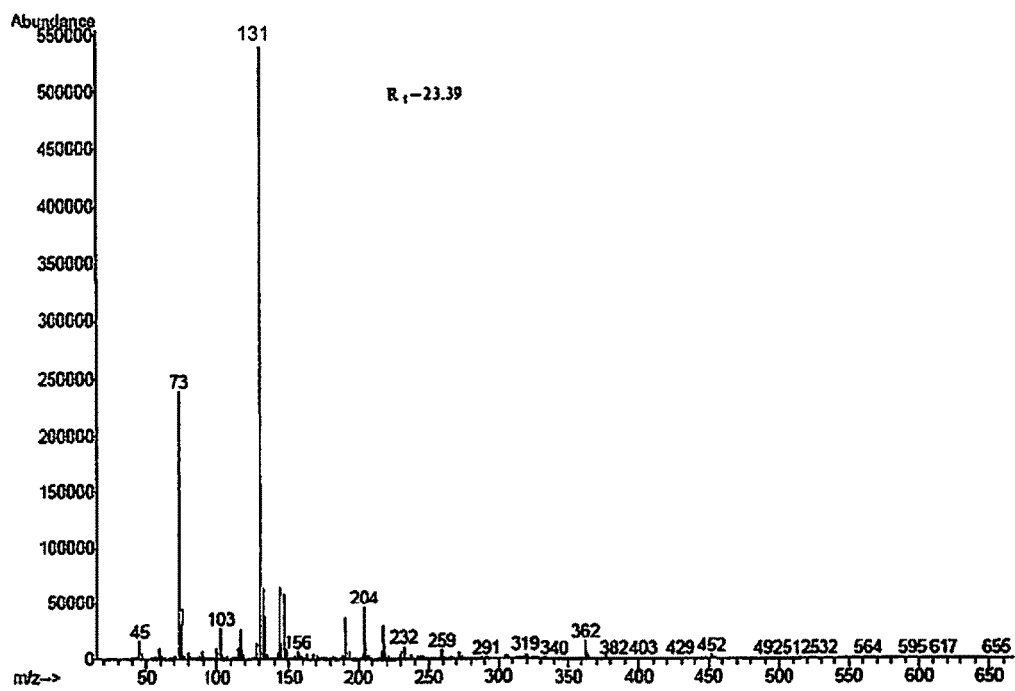

FIG. 25 depicts GC-MS analysis of 1,5-di-O-acetyl-2,3,4,6-tetra-O-methyl-D-glucitol derivative of alditol acetates of Lithium-ethylenediamine degraded polymeric biosurfactant produced by *Microbacterium* sp. strain BS-2.

Figure 26:
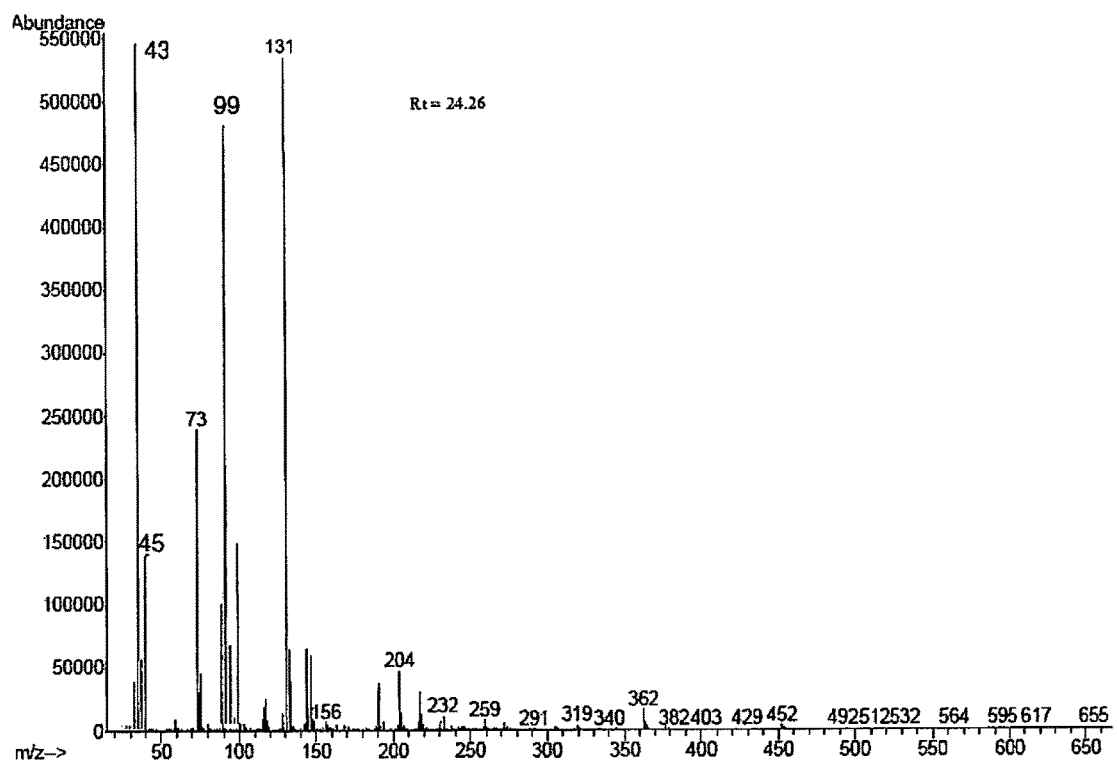

FIG. 26 depicts GC-MS analysis of 2,3,6-tri-O-methyl-1,4,5-tri-O-acetyl-D-galactacitol derivative of alditol acetates of Lithium-ethylenediamine degraded polymeric biosurfactant produced by *Brevibacillus* sp. strain BS-207.

Figure 27:
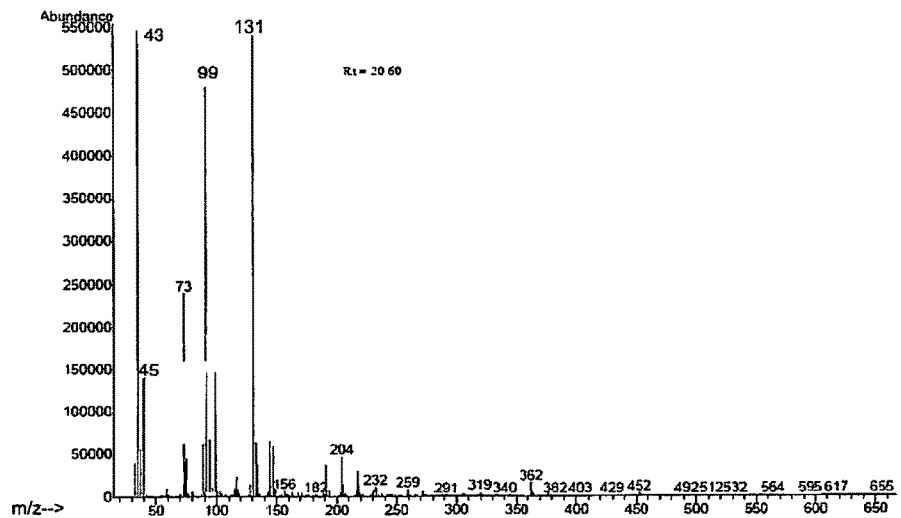

FIG. 27 depicts GC-MS analysis of 2,3,6-tri-O-methyl-1,4,5-tri-O-acetyl-D-mannitol derivative of alditol acetates of Lithium-ethylenediamine degraded polymeric biosurfactant produced by *Brevibacillus* sp. strain BS-207.

Figure 28:
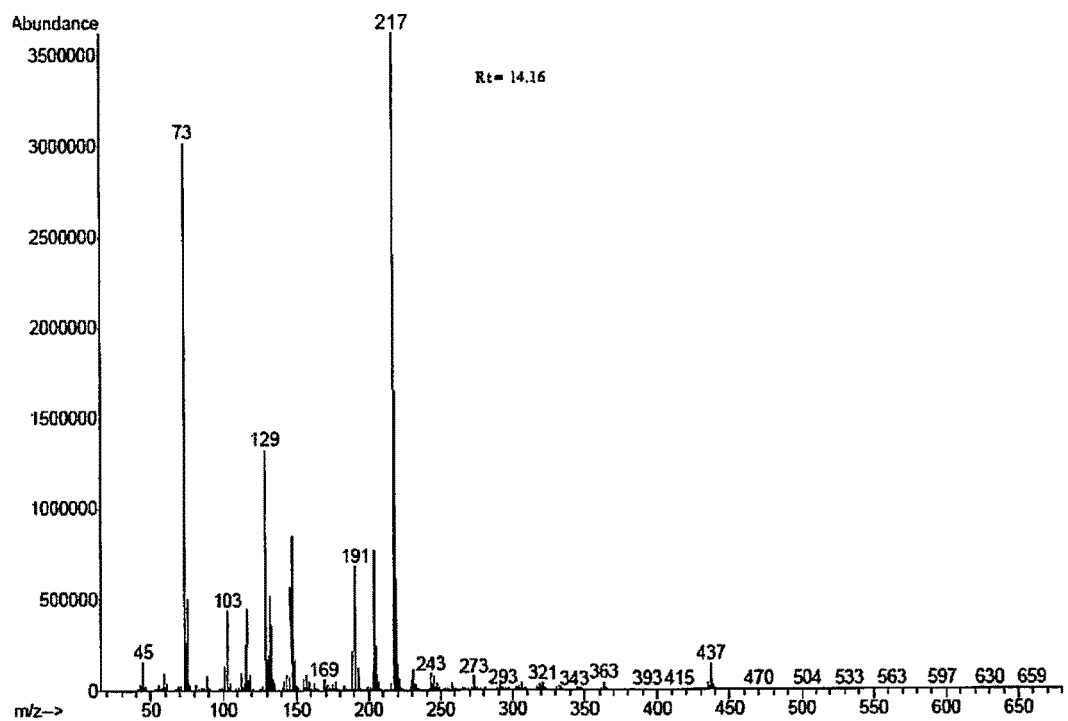

FIG. 28 depicts GC-MS analysis of 2,3,4,6-tetra-O-methyl-1,5-di-O-acetyl-D-galactocitol derivative of alditol acetates of Lithium-ethylenediamine degraded polymeric biosurfactant produced by *Brevibacillus* sp. strain BS-207.

Figure 29:
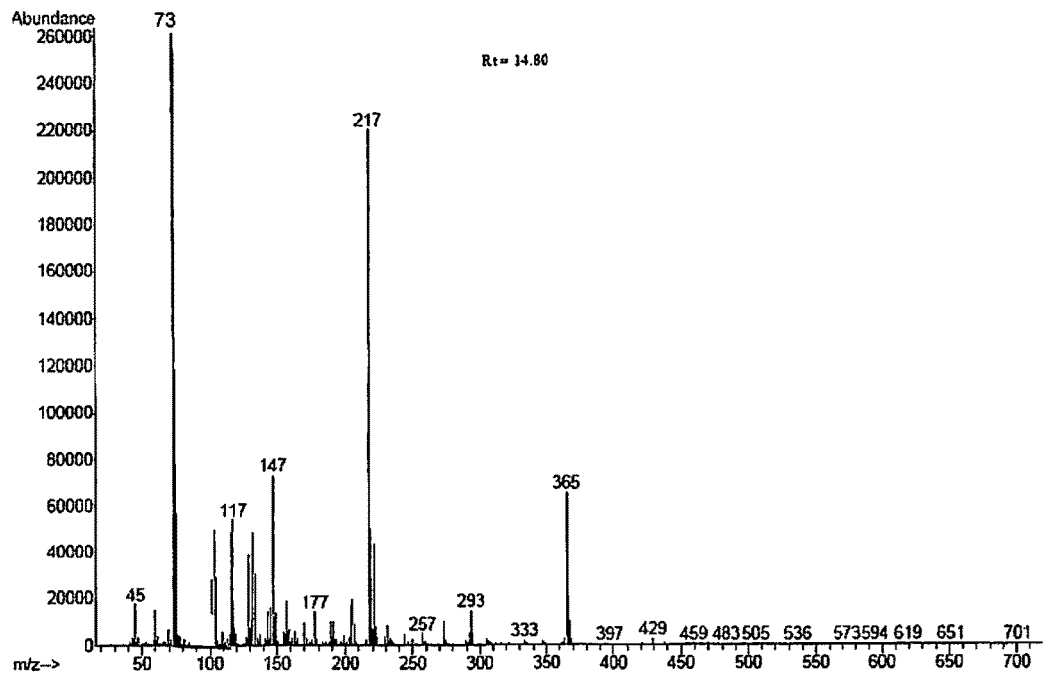

FIG. 29 depicts GC-MS analysis 2,3,4,6-tetra-O-methyl-1,5-di-O-acetyl-D-mannitol derivative of alditol acetates of Lithium-ethylenediamine degraded polymeric biosurfactant produced by *Brevibacillus* sp. strain BS-207.

Figure 30A:
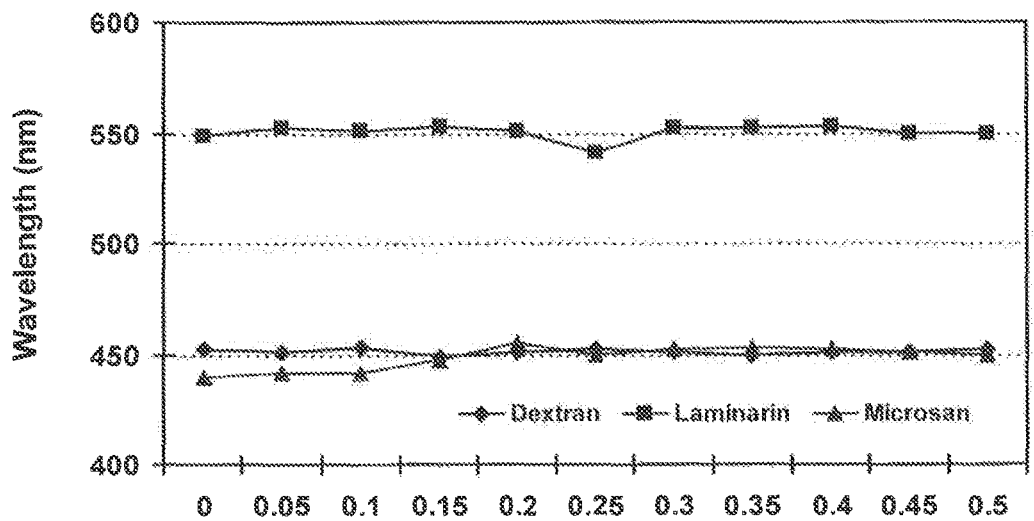
Figure 30B:
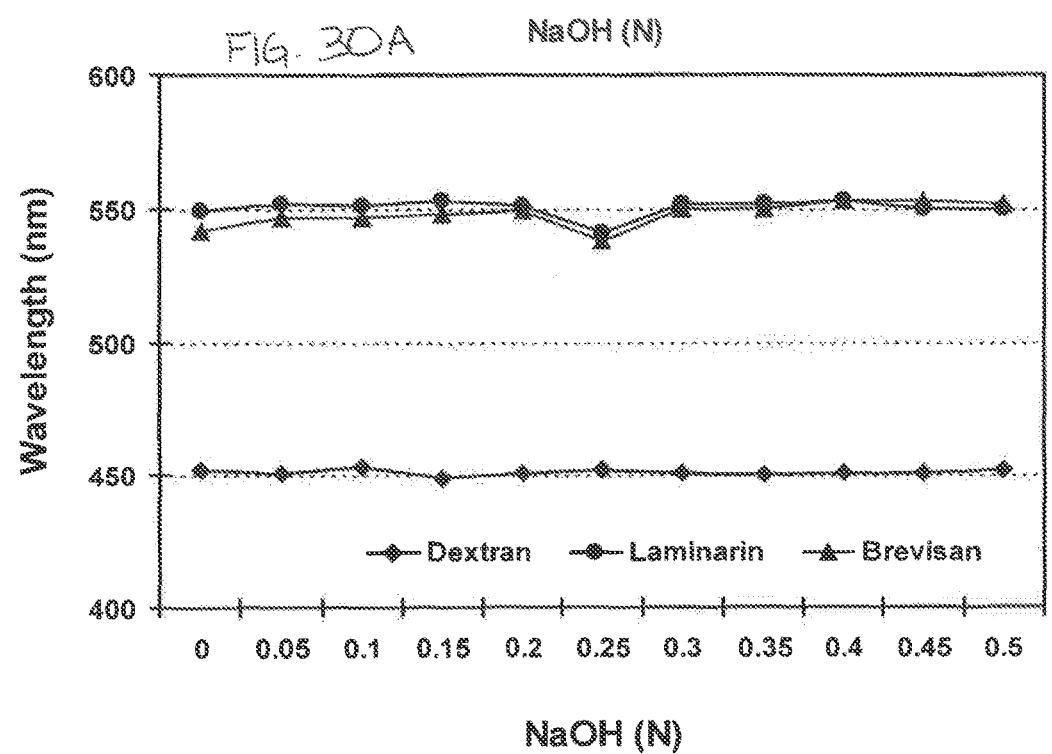

FIGS. 30A-30B depicts Congo red analysis of polymeric biosurfactants produced by 30A *Microbacterium* sp. strain BS-2 and 30B *Brevibacillus* sp. strain BS-207.

Figure 31A:
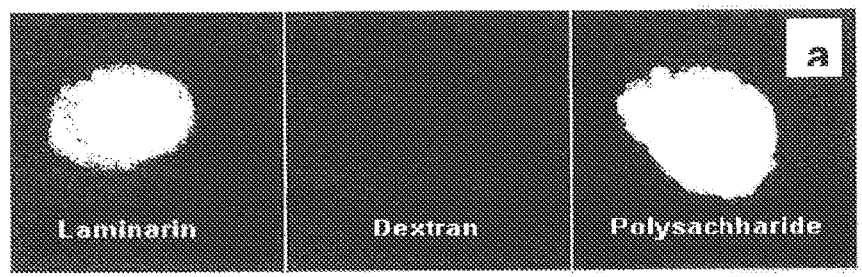
Figure 31B:
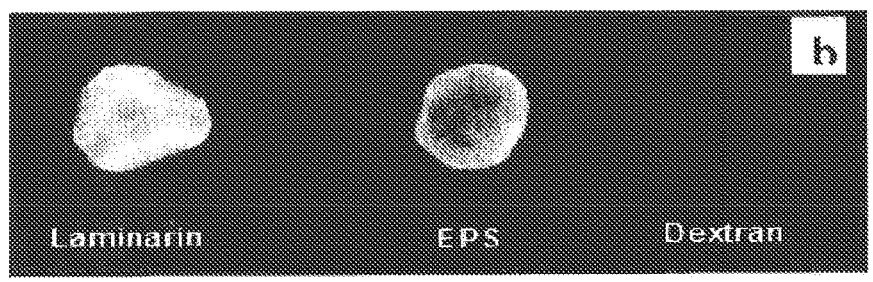

FIGS. 31A-31B depicts Fungi-Fluor staining of polymeric biosurfactants produced by 31A *Microbacterium* sp. strain BS-2 and 31B *Brevibacillus* sp. strain BS-207.

Figure 32A:
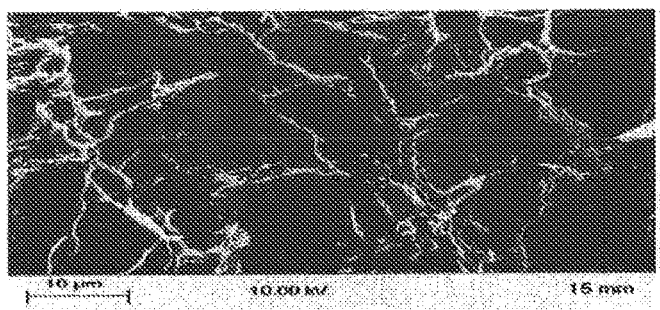
Figure 32B:
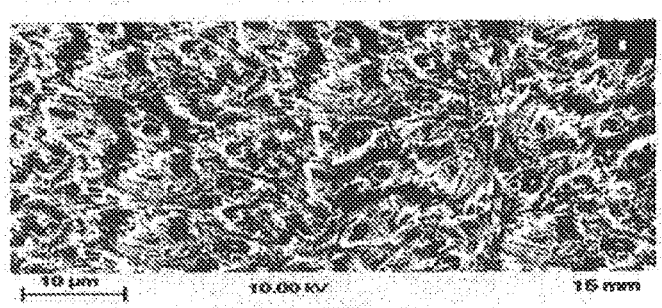

FIGS. 32A-32B depicts SEM analysis of polymeric biosurfactants produced by 32A *Microbacterium* sp. strain BS-2 and 32B *Brevibacillus* sp. strain BS-207.

Figure 33A:
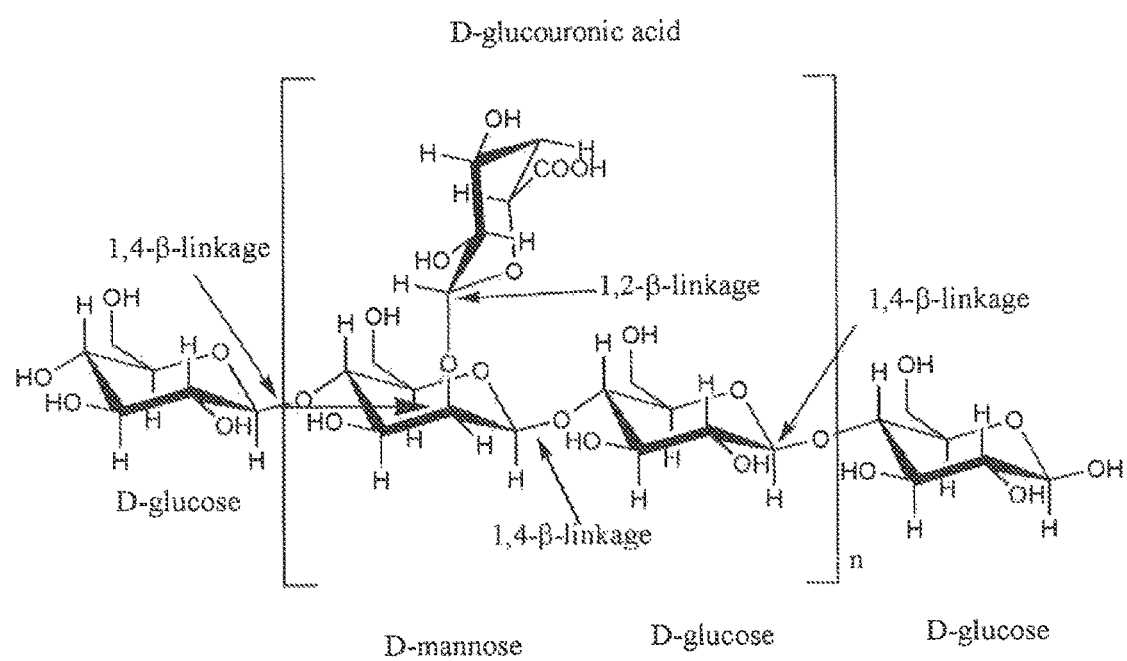
Figure 33B:
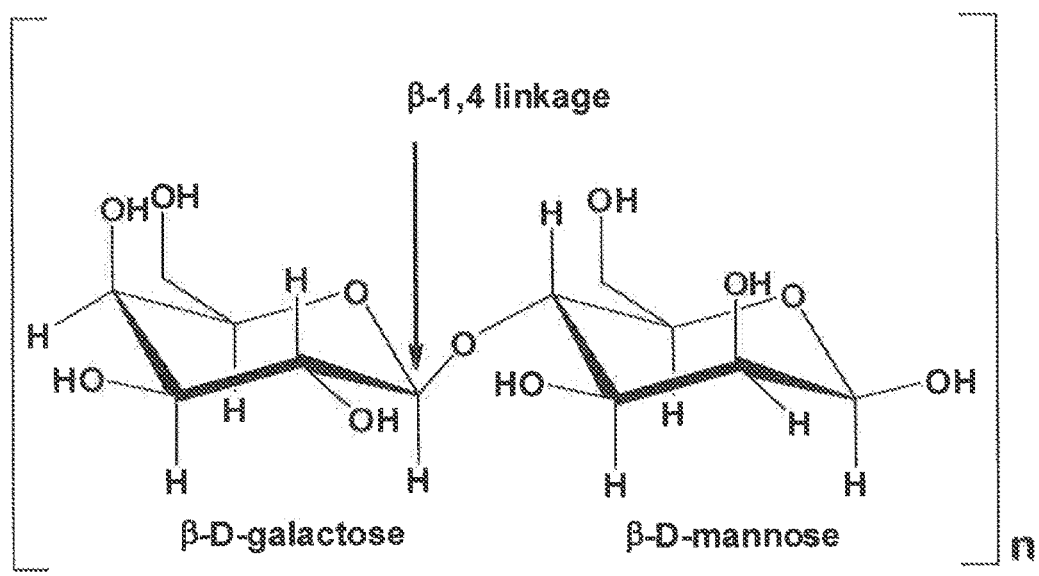

FIGS. 33A-33B depicts predicted structures of polymeric biosurfactants produced by 33A *Microbacterium* sp. strain BS-2 and 33B *Brevibacillus* sp. strain BS-207.

Figure 34A:
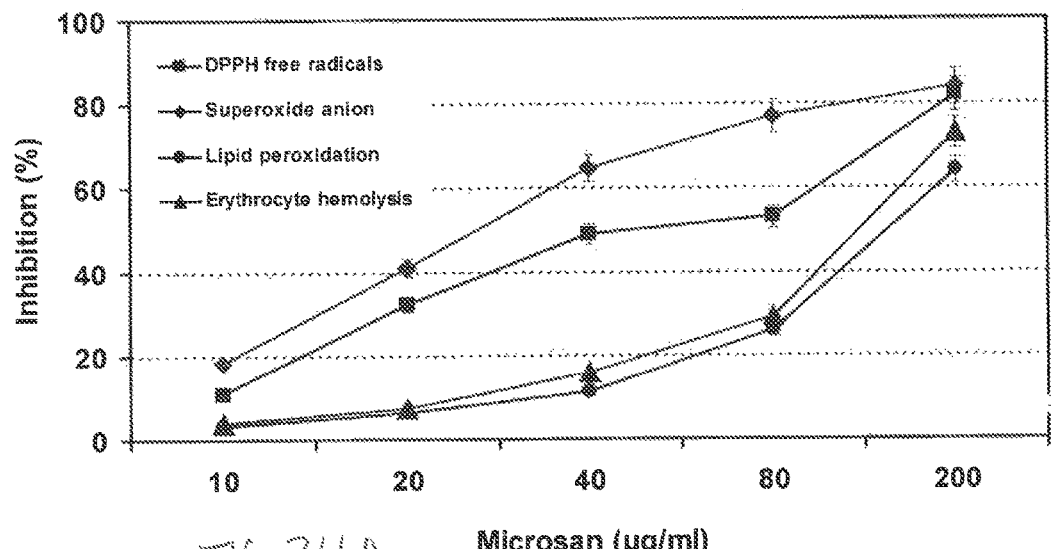
Figure 34B:
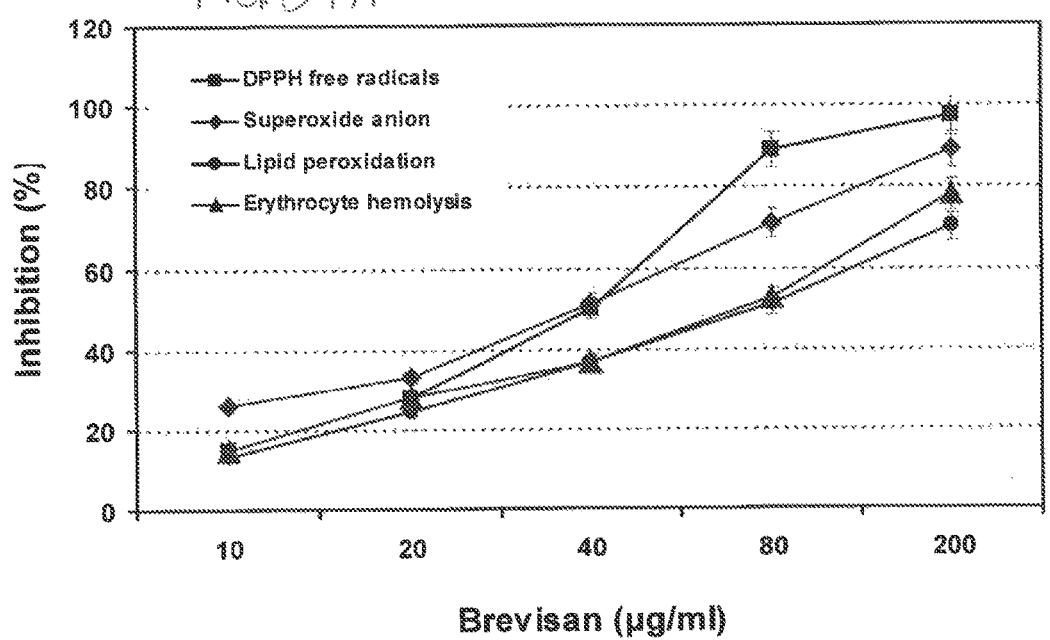

FIGS. 34A-34B depicts Antioxidant activities of polymeric biosurfactants produced by 34A *Microbacterium* sp. strain BS-2 and 34B *Brevibacillus* sp. strain BS-207.

Figure 35:
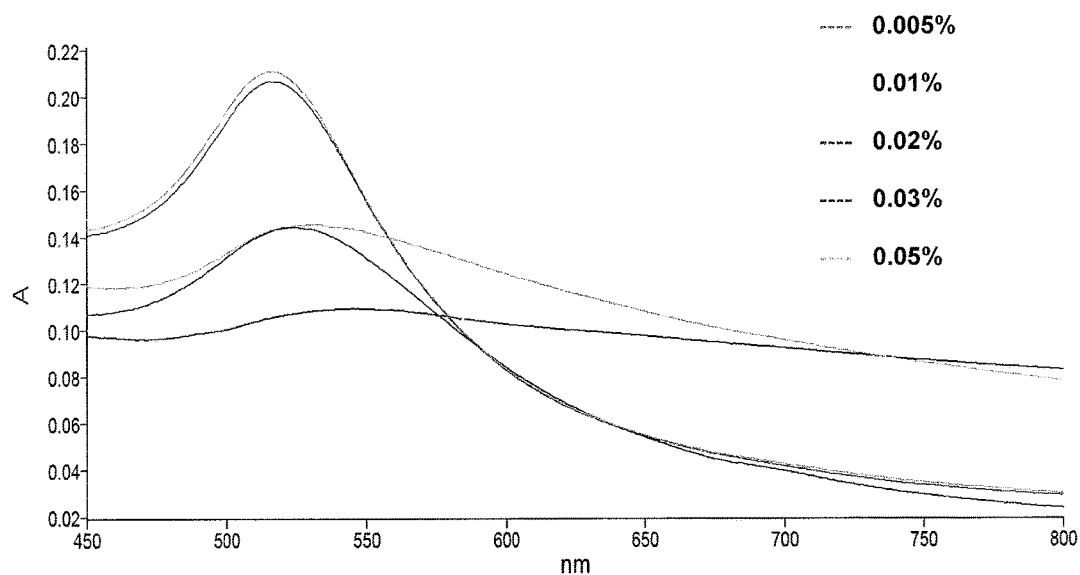

FIG. 35 depicts UV-visible spectral analysis of gold nanoparticles (M-EPS-Au-NP) formed with different concentrations of polymeric biosurfactant from *Microbacterium* sp. strain BS-2.

Figure 36:
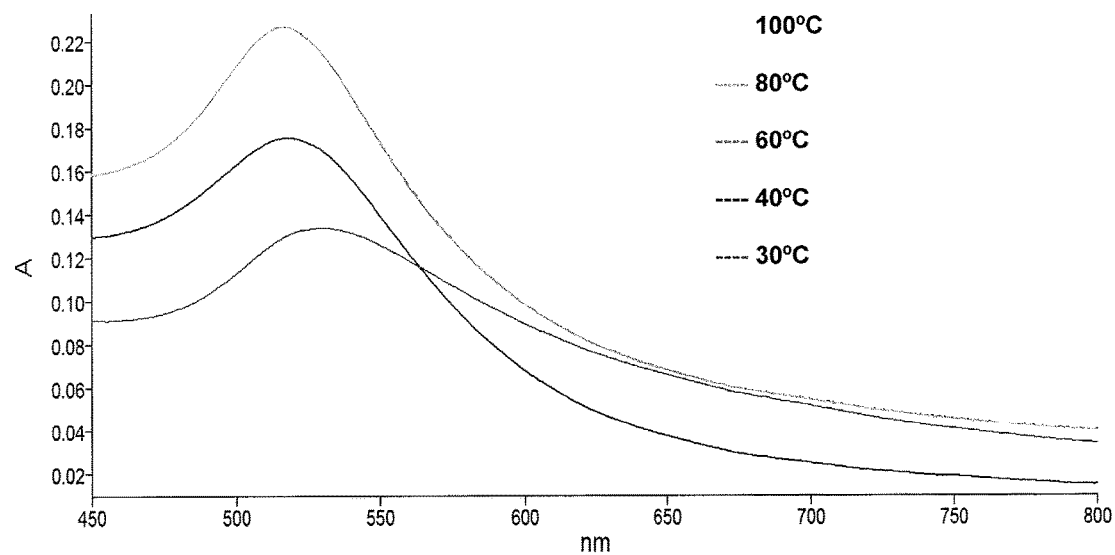

FIG. 36 depicts UV-visible spectral analysis of gold nanoparticles (M-EPS-Au-NP) formed at different temperatures.

Figure 37:
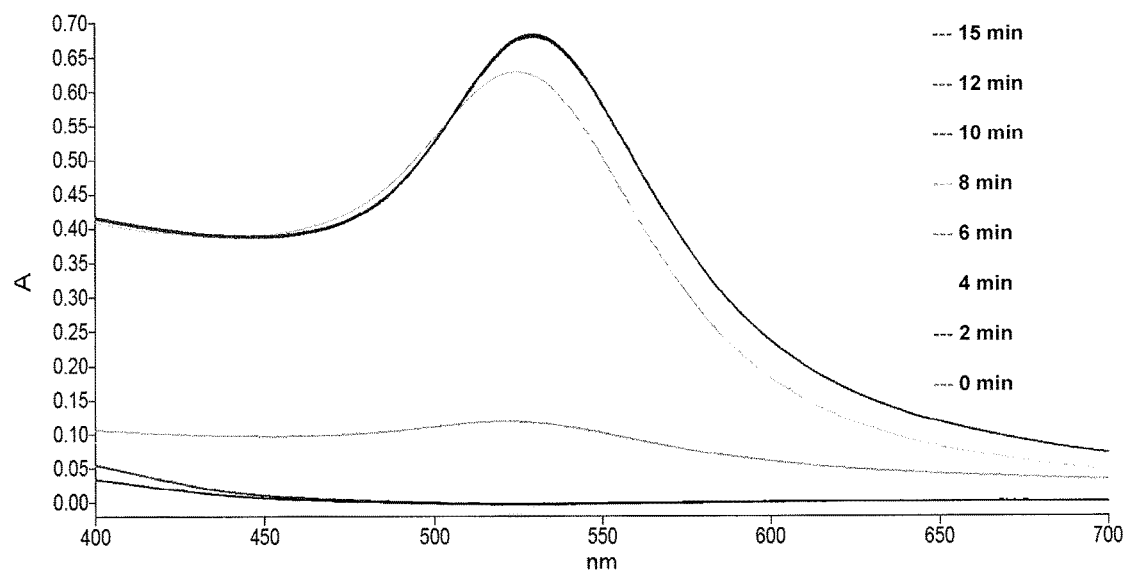

FIG. 37 depicts UV-visible spectral analysis of time-dependent synthesis of gold nanoparticles (M-EPS-Au-NP) using polymeric biosurfactant from *Microbacterium* sp. strain BS-2.

Figure 38:
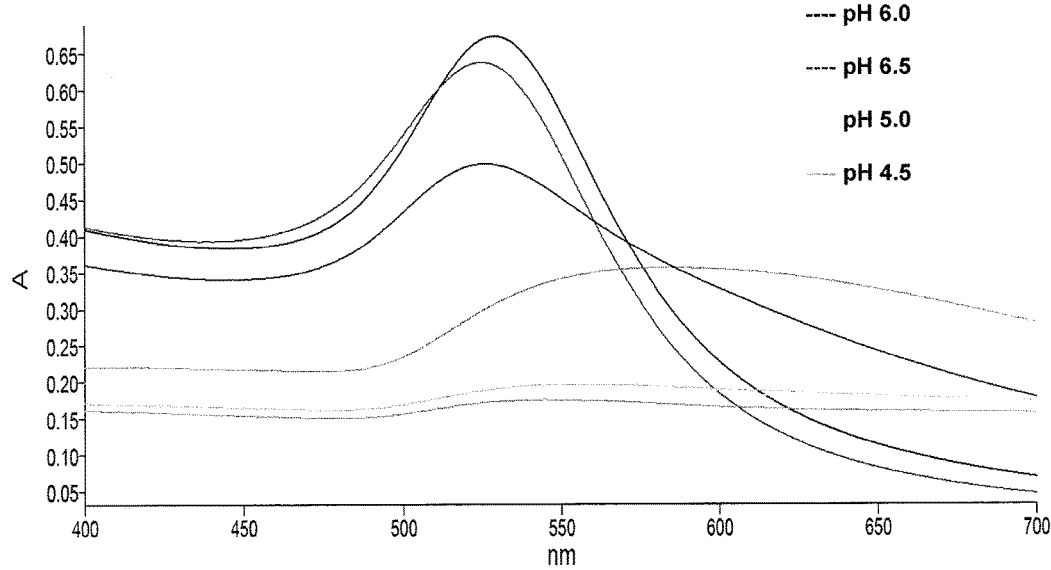

FIG. 38 depicts UV-visible spectral analysis of Microsan-capped gold nanoparticles (M-EPS-Au-NP) formed at different pH values.

Figure 39:
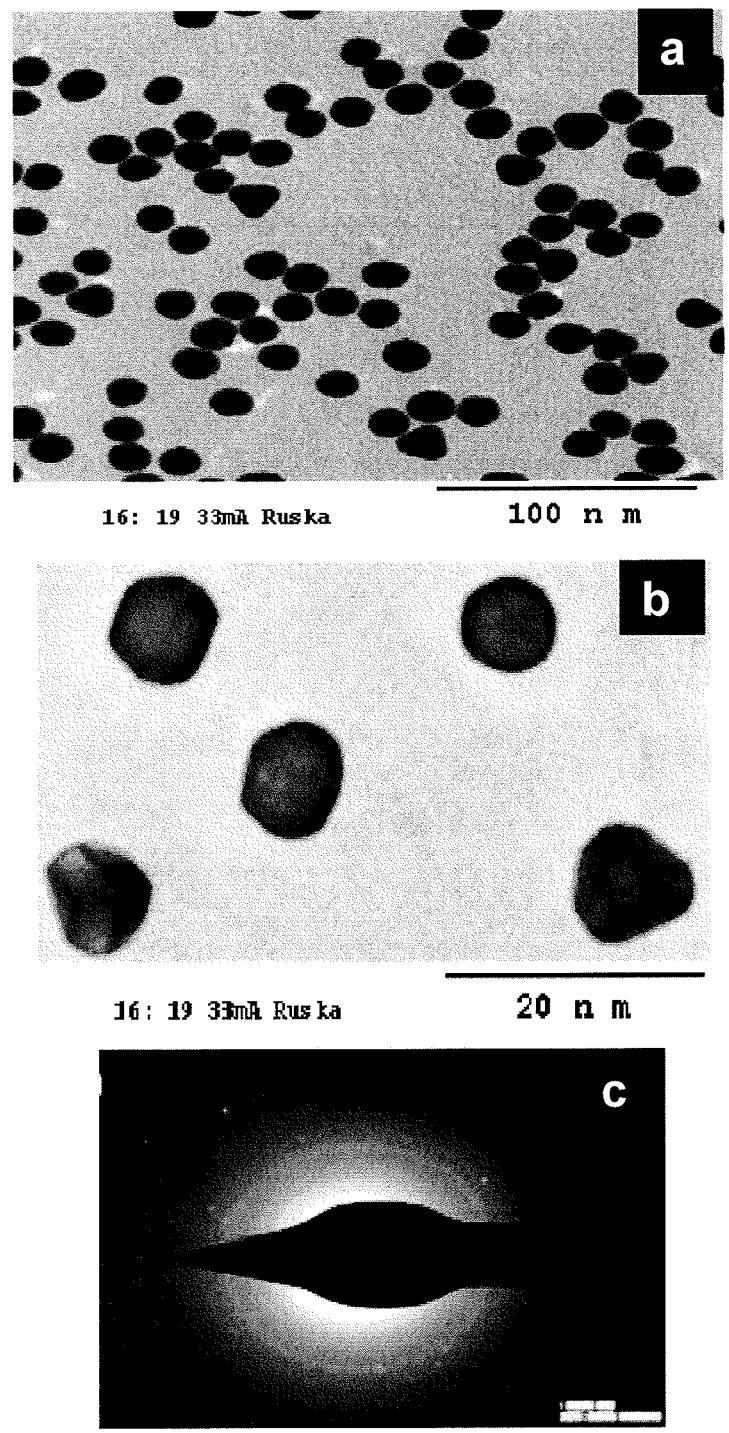

FIG. 39 depicts TEM analysis of gold nanoparticles (M-EPS-Au-NP) formed with polymeric biosurfactant (0.01%) from *Microbacterium* sp. strain BS-2.

Figure 40:
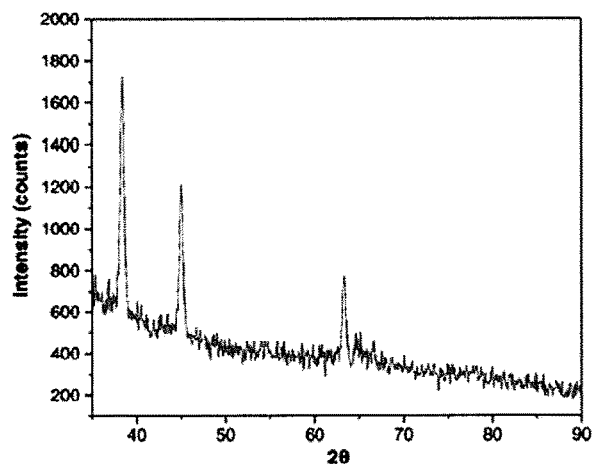

FIG. 40 depicts XRD analysis of gold nanoparticles (M-EPS-Au-NP) formed with polymeric biosurfactant (0.01%) from *Microbacterium* sp. strain BS-2.

Figure 41:
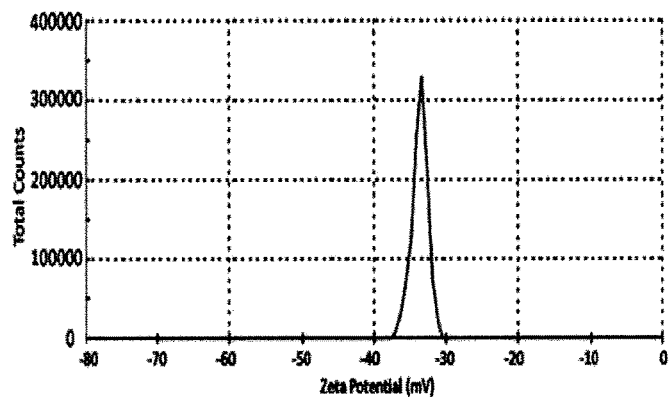

FIG. 41 depicts Zeta potential of gold nanoparticles (M-EPS-Au-NP) formed with polymeric biosurfactant (0.01%) from *Microbacterium* sp. strain BS-2.

Figure 42:
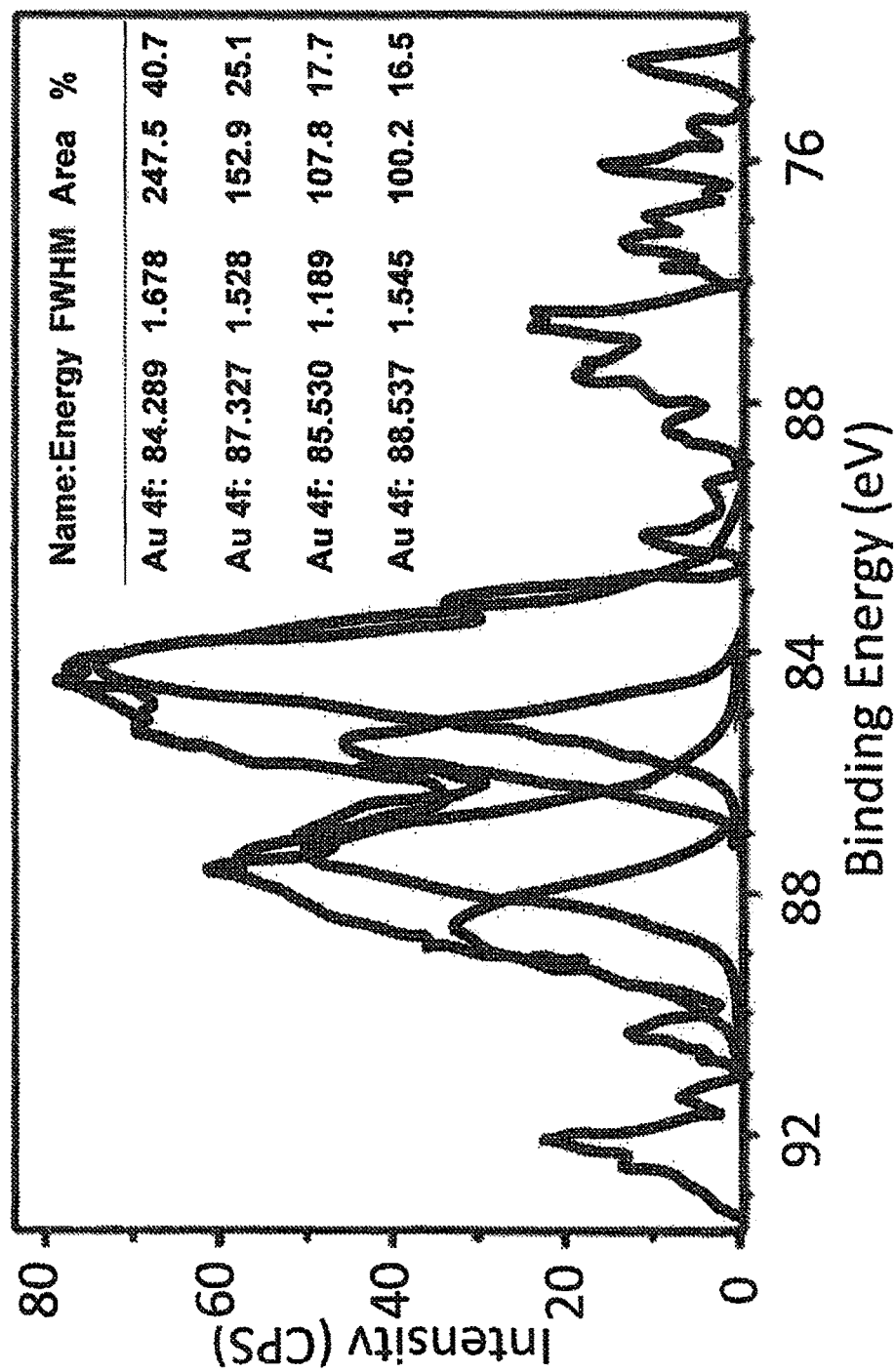

FIG. 42 depicts XPS analysis of gold nanoparticles (M-EPS-Au-NP) formed with polymeric biosurfactant (0.01%) from *Microbacterium* sp. strain BS-2.

Figure 43:
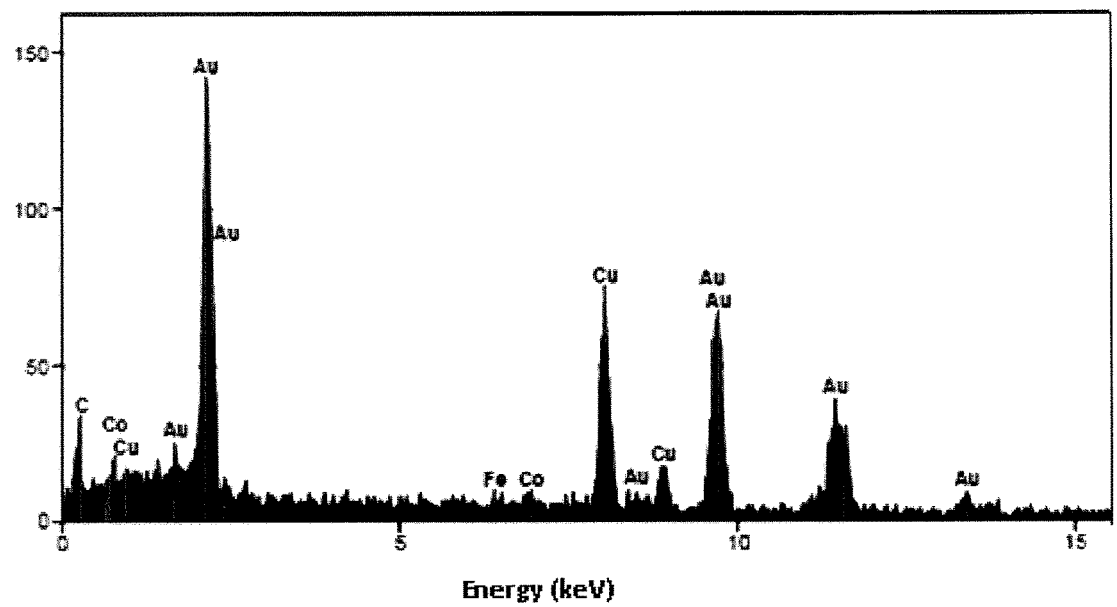

FIG. 43 depicts EDS analysis of gold nanoparticles (M-EPS-Au-NP) formed with polymeric biosurfactant (0.01%) from *Microbacterium* sp. strain BS-2.

Figure 44:
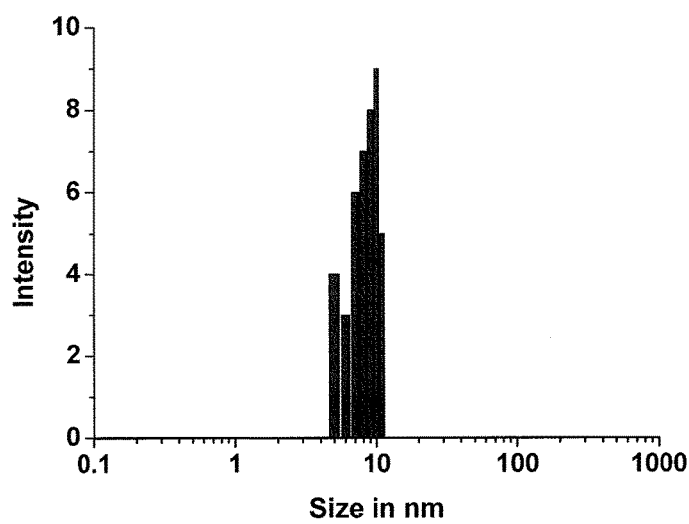

FIG. 44 depicts DLS analysis of gold nanoparticles (M-EPS-Au-NP) formed with polymeric biosurfactant (0.01%) from *Microbacterium* sp. strain BS-2.

Figure 45A:
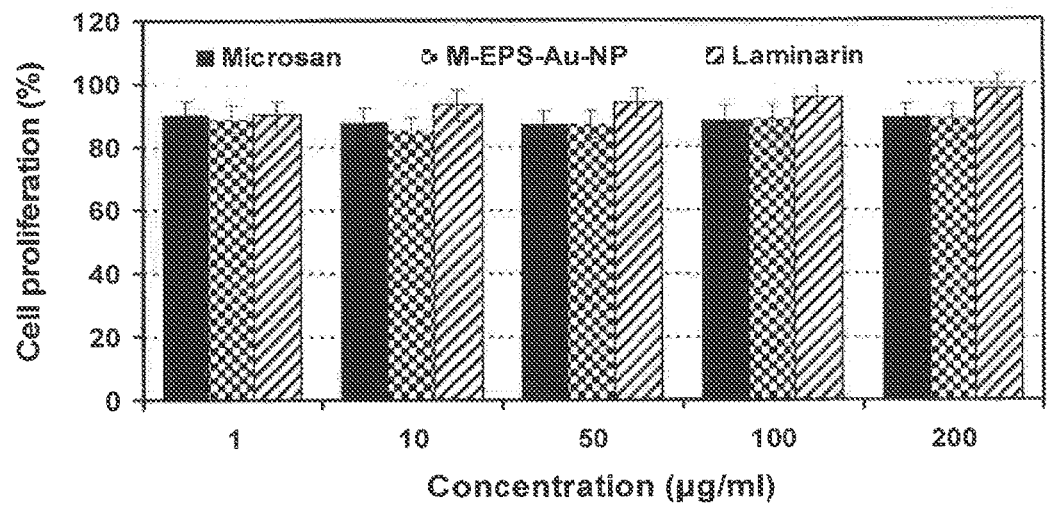
Figure 45B:
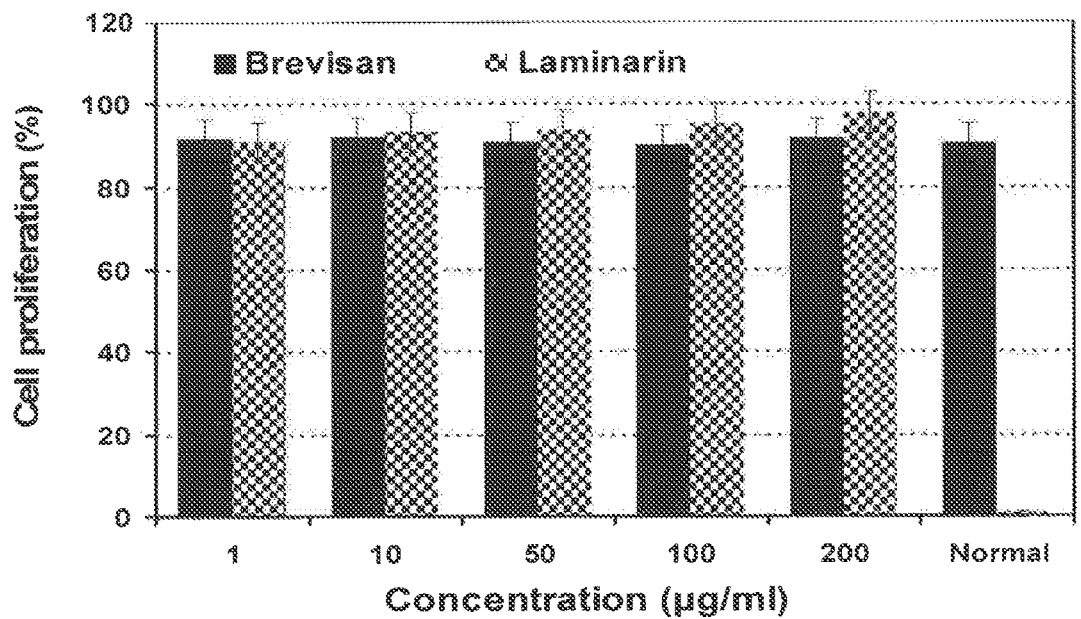

FIGS. 45A-45B depicts In vitro MTT assay of 45A Microsan and M-EPS-Au-NP, and 45B Brevisan on RAW 264.7 mouse macrophages.

Figure 46:
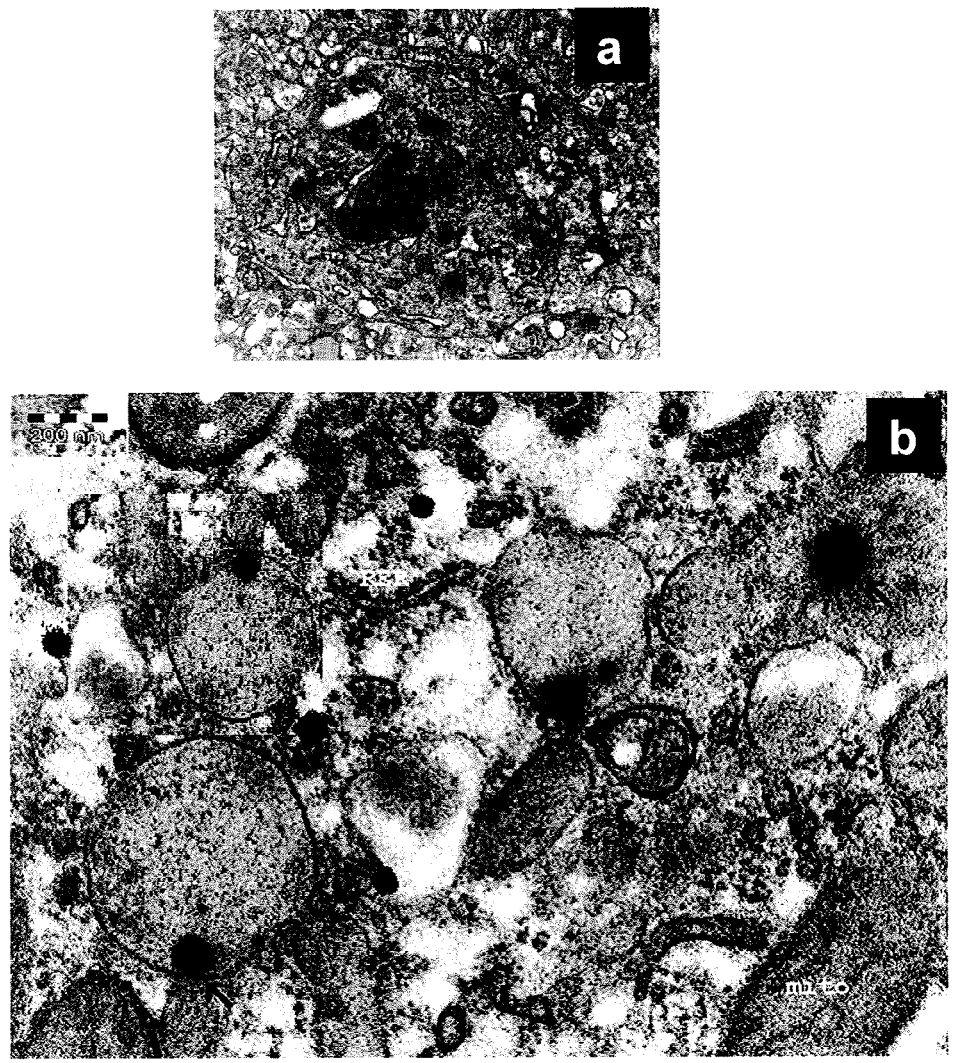

FIG. 46 depicts TEM analysis to show the localization of M-EPS-Au-NP in RAW 264.7 mouse macrophages.

Figure 47A:
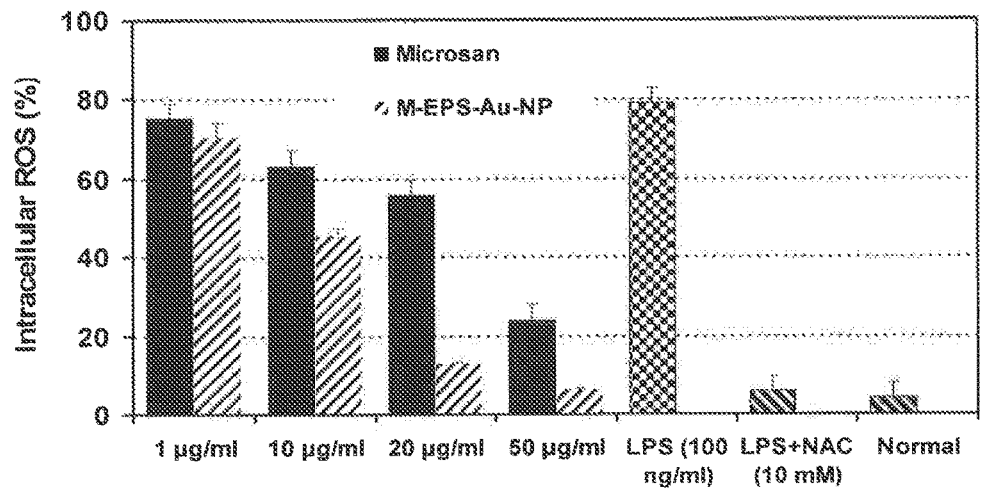
Figure 47B:
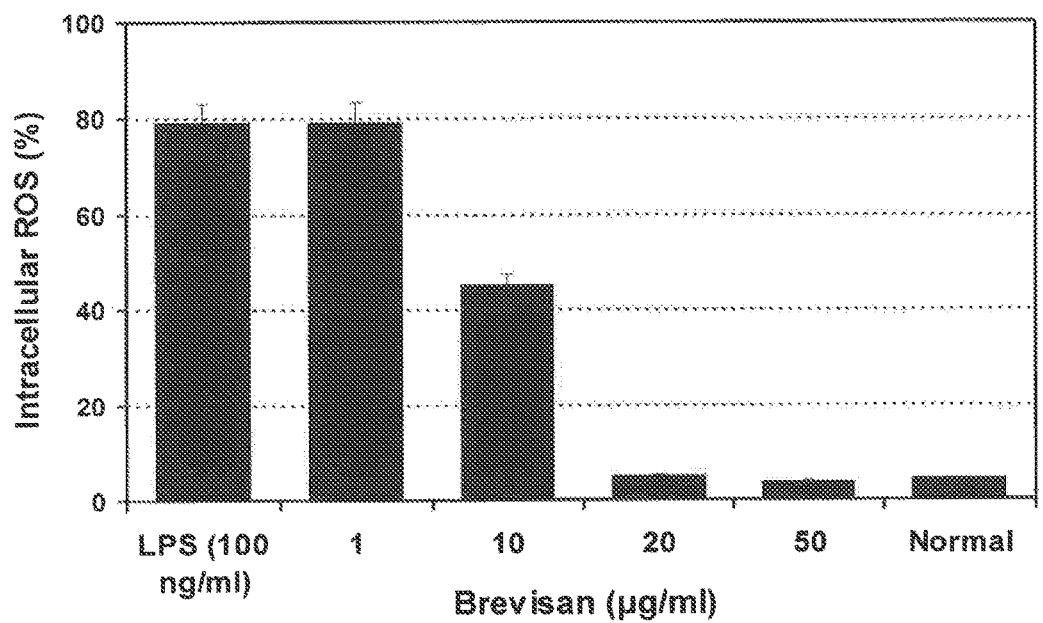

FIGS. 47A-47B depicts inhibition of LPS-induced intracellular ROS in RAW 264.7 mouse macrophages by 47A Microsan and M-EPS-Au-NP, and B Brevisan.

Figure 48A:
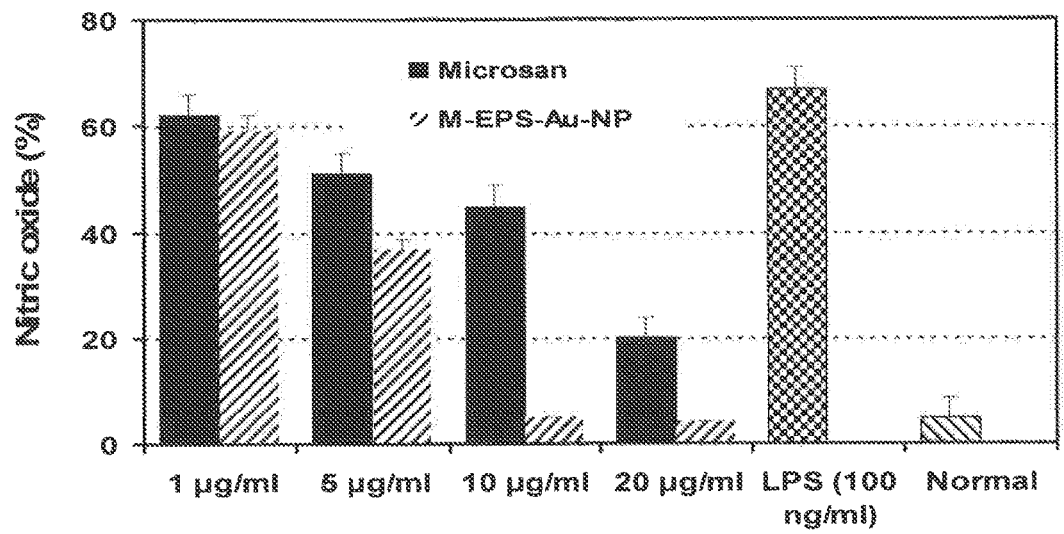
Figure 48B:
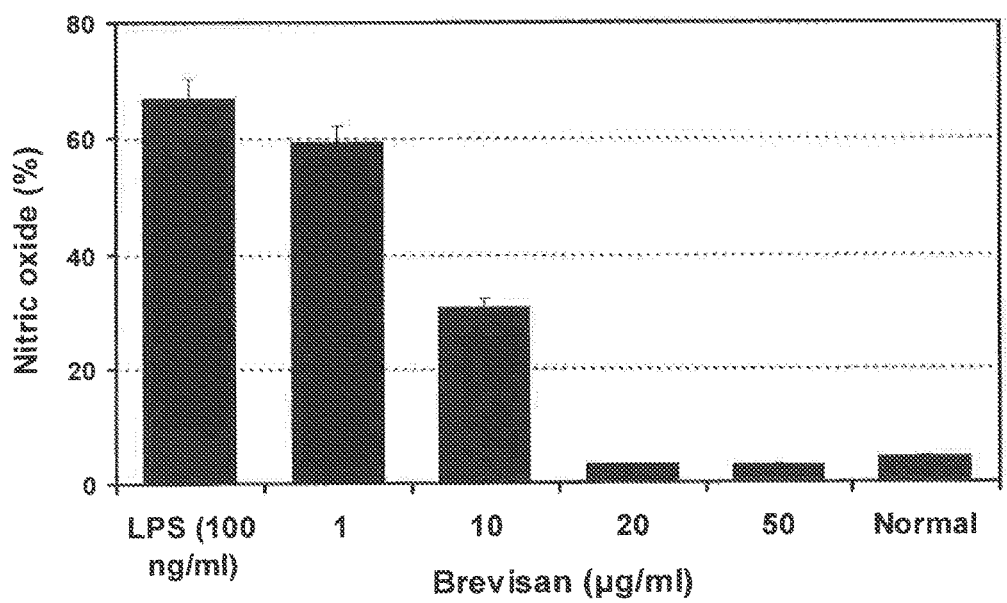

FIGS. 48A-48B depicts inhibition of LPS-induced NO in RAW 264.7 mouse macrophages by 48A Microsan and M-EPS-Au-NP, and 48B Brevisan.

FIGS. 49A-49B depicts inhibition of LPS-induced COX-2 in RAW 264.7 mouse macrophages by 49A Microsan and M-EPS-Au-NP, and 49B Brevisan.

Figure 50:
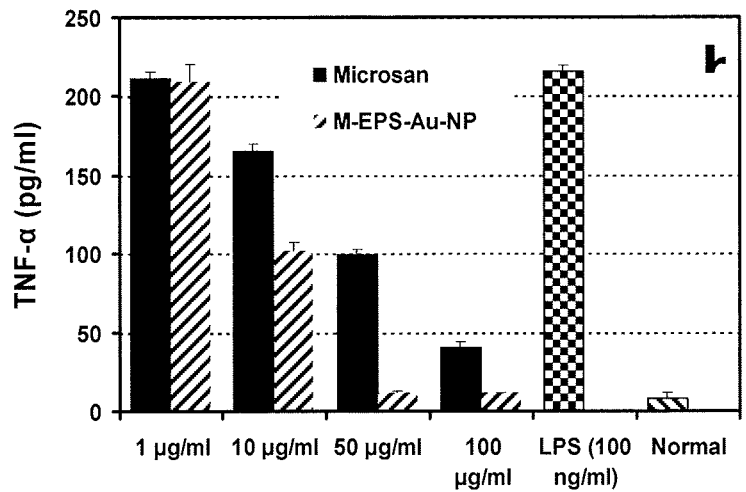

FIG. 50 depicts inhibition of LPS-induced proinflammatory cytokines, (a) TNF-α and (b) IL-6 levels in RAW 264.7 mouse macrophages by Microsan and M-EPS-Au-NP.

Figure 51:
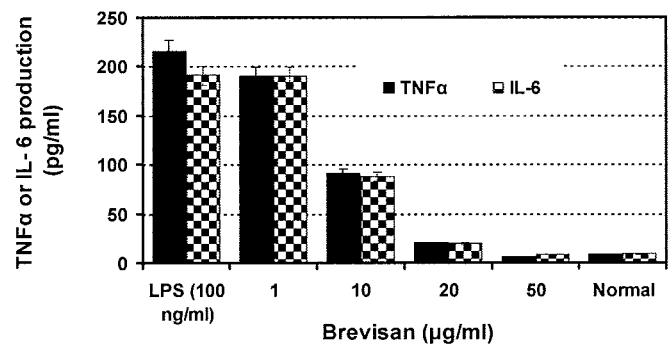

FIG. 51 depicts inhibition of proinflammatory cytokines, TNF-α and IL-6, production in RAW 264.7 mouse macrophages by Brevisan.

Figure 52:
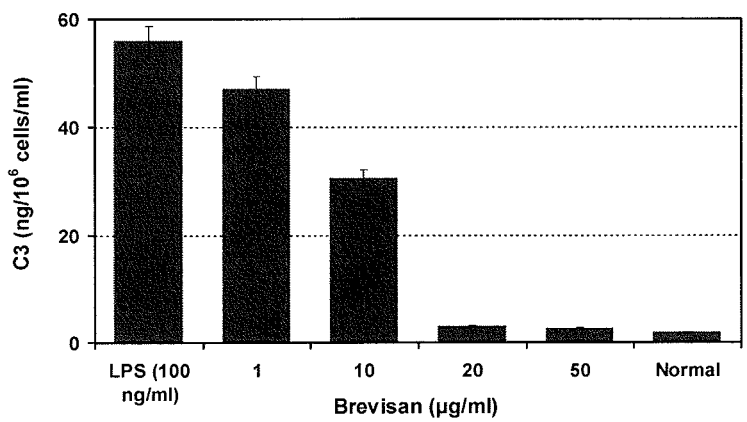

FIG. 52 depicts inhibition of C3 complement component production from RAW 264.7 mouse macrophages by Brevisan.

Figure 53:
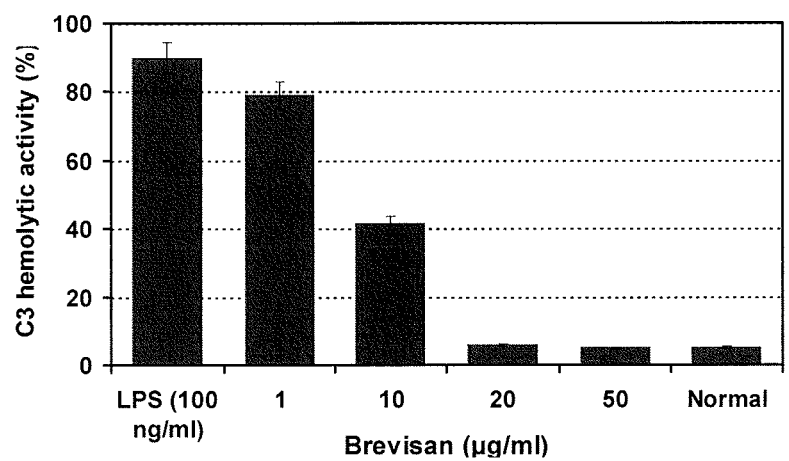

FIG. 53 depicts inhibition of C3 hemolytic activity in RAW 264.7 mouse macrophages by Brevisan.

SUMMARY OF THE INVENTION

Accordingly, present invention provides a polymeric biosurfactants isolated from bacterial strains and characterized in that they are exopolysaccharide in nature.

In an embodiment of the present invention, the polymeric (EPS) biosurfactants further characterized in having glucose, mannose and glucuronic acid residues in β-(1→4), (1→2) configuration, an average molecular weight (Mw) of 36663 KDa, intrinsic viscosity of 1.0 dL/g and showing random coil confirmation.

In another embodiment of the present invention, the polymeric biosurfactants further characterized in having galactose and mannose residues in β-(1→4) configuration, an average molecular weight (Mw) of 42260 KDa, intrinsic viscosity of 1.0 dL/g and showing triple helical confirmation.

In yet another embodiment of the present invention, said biosurfactants are useful as an antibacterial, antioxidant, anti-inflammatory, immunomodulatory, and immunosuppressive agent.

In yet another embodiment, present invention provides a method for producing polymeric biosurfactants under aerobic conditions in an aqueous nutrient medium comprising the steps of:
  a) isolating bacterial strains *Microbacterium* sp. strain BS-2 (MTCC 5822) and *Brevibacillus* sp. strain BS-207 (MTCC 5823) from petroleum contaminated soil collected from Mupkal, Nizamabad, Andhra Pradesh, India (latitude 18.90° N and longitude 78.36° E) using N-hexadecane (1%, v/v);
  b) subjecting the isolated strains as obtained in step (a) to grow in the fermentation media at temperature in the range of 35 to 40° C. for period in the range of 45 to 50 hr;
  c) centrifuging the culture as obtained in step (b) at temperature in the range of 3 to 5° C. to obtain polymeric biosurfactants.

In yet another embodiment of the present invention, fermentation media used at step (b) to grow the isolated strain contains minimal salts medium (pH 7.5 to 8) supplemented with NaCl (1 $g^{/-1}$), glucose (20-25 $g^{/-1}$, w/v), ammonium nitrate (0-2.5 $g^{/-1}$, w/v) and ammonium sulphate (0-2 $g\ l^{-1}$, w/v).

In yet another embodiment of the present invention, said biosurfactants inhibit the generation of DPPH free radicals, superoxide anions, lipid peroxidation and erythrocyte hemolysis with effective concentrations ($EC_{50}$) of 40.78, 24.48, 165.94 and 139.28 μg $ml^{-1}$, respectively and 39.97, 37.88, 81.98 and 79.98 μg $ml^{-1}$, respectively.

In yet another embodiment of the present invention, said biosurfactants reduce and stabilize gold nanoparticles at 0.01% concentration to obtain polymeric biosurfactant-capped gold nanoparticles.

In yet another embodiment of the present invention, said biosurfactant and polymeric biosurfactant-capped gold nanoparticles exhibits antibacterial activity with MIC values ranging from 9.37 to 2.34 μg ml-1.

In yet another embodiment of the present invention, the polymeric biosurfactants (concentration range 10-50 μg $ml^{-1}$) and polymeric biosurfactant-capped gold nanoparticles inhibits the lipopolysaccharide-induced reactive oxygen species (ROS) and nitric oxide (NO) generation levels by 4.98%, 55.71% and 12.74%, respectively and 3.18%, 20.05% and 4.09%, respectively, in RAW 264.7 macrophages.

In yet another embodiment of the present invention, the polymeric biosurfactants (concentration range 50-100 μg $ml^{-1}$) (concentration range 50-100 μg $ml^{-1}$) and polymeric biosurfactant-capped gold nanoparticles (concentration range 50-100 μg $ml^{-1}$) inhibits the lipopolysaccharide (LPS)-stimulated cyclooxygenase-2 (COX-2) and the subsequent generation of proinflammatory cytokines, TNF-α and IL-6, levels from 215.79 μg $ml^{-1}$ and 190.9 μg $ml^{-1}$, respectively, to 98.88 μg $ml^{-1}$ and 90.01 μg $ml^{-1}$, respectively; 20.17 μg $ml^{-1}$ and 19.98 μg $ml^{-1}$, respectively; and 12.37 μg $ml^{-1}$ and 15.7 μg $ml^{-1}$, respectively, in RAW 264.7 macrophages.

In yet another embodiment of the present invention, the polymeric biosurfactant (concentration range 10-50 μg $ml^{-1}$) inhibits the lipopolysaccharide (LPS)-induced production and hemolytic activity of C3 complement component from 55.89 ng/$10^6$ cells $ml^{-1}$ to 2.99 ng/$10^6$ cells $ml^{-1}$ in RAW 264.7 macrophages and from 89.97% to 5.71% in LPS-stimulated RAW 264.7 macrophages respectively.

DETAILED DESCRIPTION OF THE INVENTION

The present invention provide potential polysaccharide-based biosurfactants exhibiting surface-active reducing property with antibacterial, antioxidant and anti-inflammatory properties with potential immunomodulatory effects in RAW 264.7 macrophages and thus finds application as potential immunosuppressive agents.

The novel polymeric biosurfactants of the present invention were characterized as acidic and neutral polysaccharides and obtained from two bacterial strains, *Microbacte-*

*rium* sp. strain BS-2 [MTCC 5822] and *Brevibacillus* sp. strain BS-207 [MTCC 5823], which have been isolated from a petroleum contaminated soil sample collected from Mupkal, Nizamabad, Andhra Pradesh, India (latitude 18.90° N and longitude 78.36° E). The present invention relates to the microbial production of two polymeric biosurfactants with immunomodulatory effects.

The bacterial strains were isolated by transferring the soil sample in an enrichment medium containing 1.0 g of each soil sample in 100 ml of mineral salts medium supplemented with N-hexadecane (1%, v/v) as a sole carbon source for three weeks. Serial dilutions of the enriched samples were made and then plated on the mineral salts agar plates overlaid with N-hexadecane which acted as a sole carbon source. The colonies that appeared on the plates upon incubation at 37° C. for 72 h were purified for 2-3 times on nutrient agar plates. The isolated pure microbes were scrapped off from the agar plate and cultured in liquid mineral salts medium at 37° C. for 72 h. The cells were separated by centrifugation and the cell-free supernatant was tested for reduction of surface tension values using a tensiometer. The microorganisms with maximum surface tension lowering ability was selected as promising biosurfactant producers which were further identified as *Microbacterium* sp. and *Brevibacillus* sp., based on their morphological, physiological and biochemical characterization followed by 16S rDNA sequencing. The biologically pure cultures of these two microorganisms have been deposited at the Microbial Type Culture Collection, CSIR-Institute of Microbial Technology, Chandigarh, India with the accession numbers MTCC 5822 and MTCC 5823. The two polymeric biosurfactant-producing strains, *Microbacterium* sp. strain BS-2 belong to the family Microbacteriaceae of the order Actinomycetales, while the *Brevibacillus* sp. strain BS-207 belongs to the family Paenibacillaceae.

Microsan from *Microbacterium* sp. BS-2 has reducing and stabilizing properties and acted as capping ligands in the synthesis of gold nanoparticles (M-EPS-Au-NP), both acted as antimicrobial agents against the tested bacterial pathogens.

Microsan and M-EPS-coated gold nanoparticles showed immunomodulatory effects in RAW 264.7 cells by inhibiting reactive oxygen species and nitric oxide without affecting the cell proliferation. Brevisan also exhibited immunomodulatory effects in RAW 264.7 macrophages. Microsan and Brevisan showed anti-inflammatory activity by inhibiting the COX-2 and pro-inflammatory cytokines, TNF-α and IL-6 in RAW 264.7 cells. In addition, Brevisan only inhibited the production and hemolytic activity of C3 complement component in LPS-stimulated RAW 264.7 macrophages. Microsan and Brevisan exhibited multi-functional activities like antimicrobial, antioxidant, anti-inflammatory and immunomodulating properties and thus finds application as potential immunosuppressive agents.

The present invention describes the purification and structural characterization of polymeric biosurfactants produced by two bacterial strains of *Microbacterium* sp. strain BS-2 (MTCC 5822) and *Brevibacillus* sp. strain BS-207 (MTCC 5823), which were isolated from a petroleum-contaminated soil sample. The surface active properties and antioxidant properties were evaluated in a cell free system. The antiproliferation activity and immunomodulatory effects of Microsan, Microsan-coated gold nanoparticles (M-EPS-Au-NP) and Brevisan were evaluated against RAW 264.7 macrophages. The effects of Microsan, Microsan-capped gold nanoparticles and Brevisan on intracellular reactive oxygen species (ROS) and cyclooxygenase-2 (COX-2) was also studied. Further, the anti-inflammatory effect was evaluated on inflammatory mediators such as NO, TNF-α and IL-6. The effect of Microsan, Microsan-coated gold nanoparticles and Brevisan on the production and hemolytic activity of C3 complement component was also studied in RAW 264.7 macrophages. The antimicrobial activity of Microsan, Microsan-coated gold nanoparticles and Brevisan was also evaluated against different gram-positive and gram-negative bacterial pathogens.

EXAMPLES

The following examples are given by way of illustration and therefore should not be construed to limit the scope of the present invention.

Example 1

Isolation and Screening of Biosurfactant Producing Strains

Figure 1A:
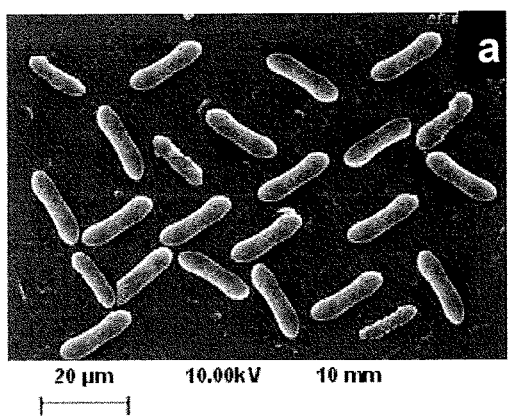
Figure 1B:
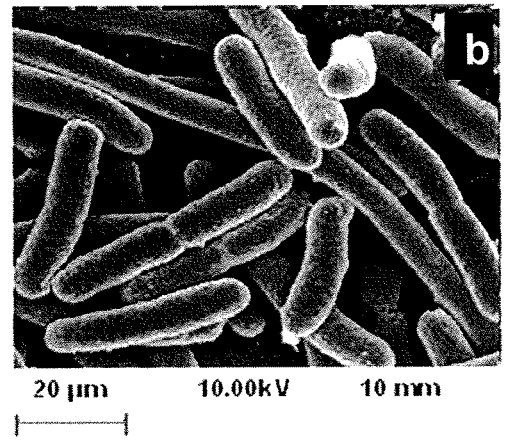

The bacterial strains producing biosurfactants were isolated from the petroleum-contaminated soil sample collected from Mupkal, Nizamabad, Andhra Pradesh, India (latitude 18.90° N and longitude 78.36° E). The soil sample was enriched by placing 1.0 g of soil sample in 100 ml of mineral salts medium supplemented with N-hexadecane (1%, v/v) as a sole carbon source for three weeks. The enriched sample was serially diluted and then plated on the mineral salts agar plates overlaid with N-hexadecane which acted as a sole carbon source. The colonies that appeared on the plates upon incubation at 37° C. for 72 h were purified for 2-3 times on nutrient agar plates. The isolated pure microorganisms were cultured in liquid mineral salts medium at 37° C. for 72 h. The cells were separated by centrifugation and the cell-free supernatant was measured for the reduction in surface tension values by Wilhelmy plate method using a Du-Nouy K100MK2 Processor Tensiometer (Krüss, Hamburg, Germany). The concentration series was generated automatically with a computer-controlled Dosimat (Metrohm AG, Switzerland). The corresponding measurements and their evaluation were performed with the LabDesk software interfaced with the tensiometer. The critical micelle concentration (CMC) was measured by plotting the concentration of surfactant as a function of surface tension, and the CMC was taken as the point where the slope of the curve abruptly changed. The microorganisms with maximum surface tension lowering ability were selected as promising biosurfactant producers which were further identified as *Microbacterium* sp. strain BS-2 (FIG. 1A) and *Brevibacillus* sp. strain BS-207 (FIG. 1B) based on their morphological, physiological and biochemical characterization (Tables 1 and 2) and 16S rDNA sequencing data.

Example 2

Parametric Optimization Studies for the Production of Polymeric Biosurfactants from *Microbacterium* Sp. Strain BS-2 and *Brevibacillus* Sp. Strain BS-207

Growth kinetics profiles of *Microbacterium* sp. strain BS-2 and *Brevibacillus* sp. strain BS-207 were assessed in minimal salts liquid medium (pH 7.5) containing (per liter): 10 g glucose, 0.5 g $NH_4SO_4$, 2.5 g $KH_2PO_4$, 2.0 g $K_2HPO_4$, 0.2 g $MgSO_4$, 0.5 g NaCl and 0.025 g $Na_2CO_3$ at 35° C. with agitation at 180 rev $min^{-1}$ for 96 h. Samples (50 ml) were collected periodically every 12 h and centrifuged at 8000 rpm for 20 min. The biomass was collected and cell dry weights were measured, while the cell-free supernatants were measured for surface tension as described earlier. The polymeric biosurfactants were extracted using ice cold isopropanol and quantified by measuring the amount of total sugars using phenol sulphuric acid method [Chaplin, M. F. and Kennedy, J. F. (1986) Carbohydrate analysis: A practical approach. Washington, D.C.: IRL Press, 129-136].

Parametric optimization studies on fermentation parameters like pH, temperature, agitation, NaCl, carbon and nitrogen sources for production of the two polymeric biosurfactants were evaluated in a minimal liquid medium (pH 7.5) as described above. The effects of pH and temperature were studied in the pH range of 5 to 11.5 and temperature range 20° C. to 70° C. Agitation studies were carried out from 100 to 250 rpm and also under static conditions. The effect of various salts like KCl, $MgCl_2$, $CaCl_2$, $BaCl_2$ (at 0.05% concentration) on biosurfactant production was also evaluated in the minimal medium by replacing NaCl. Further, the effect of NaCl at different concentrations ranging from 0.02-1% was carried out in the minimal medium. The effects of various carbon sources like glucose, fructose, sucrose, maltose, lactose, xylose, arabinose, sorbitol, mannitol, citric acid, fumaric acid, sodium pyruvate and starch at a concentration of 1% (w/v); inorganic nitrogen sources like ammonium nitrate, ammonium sulfate, sodium nitrate, potassium nitrate, and organic nitrogen sources like yeast extract, beef extract, malt extract, tryptone, peptone, soya peptone, soybean meal, casein and urea at a concentration of 0.1% (w/v) were evaluated. The effect of different concentrations of glucose and ammonium nitrate and ammonium sulphate were tested separately ranging from 0.5-6% and 0.05-0.6%, respectively, for *Microbacterium* sp. strain BS-2 and *Brevibacillus* sp. strain BS-207. The C:N ratio on biosurfactant production was examined by the addition of glucose and ammonium nitrate or ammonium sulphate as carbon and nitrogen sources, respectively, at the same time in the minimal salts medium, for *Microbacterium* sp. strain BS-2 and *Brevibacillus* sp. strain BS-207, respectively. In this regard, glucose (25 g $l^{-1}$) was used and the amount of ammonium nitrate or ammonium sulphate was varied to attain the desired C:N ratio. Experiments were carried out in 500 ml baffled flasks containing 100 ml of the medium. After inoculation with 1% inoculum ($OD_{600}$ nm of 2) of 3 days grown old culture, the flasks were incubated at 35° C. and agitated at 180 rev $min^{-1}$ for 72 h in an Ecotron (Infors AG, Switzerland) rotary shaker. After fermentation, the medium was centrifuged and the EPS was extracted from cell-free supernatant using equal volume of ice cold isopropanol and quantified using phenol-sulphuric acid method. All the experiments were carried out in triplicates and the data values have been represented as mean±standard error (S.E.) and the S.E. values are shown as Y-error bars in all figures.

Figure 2A:
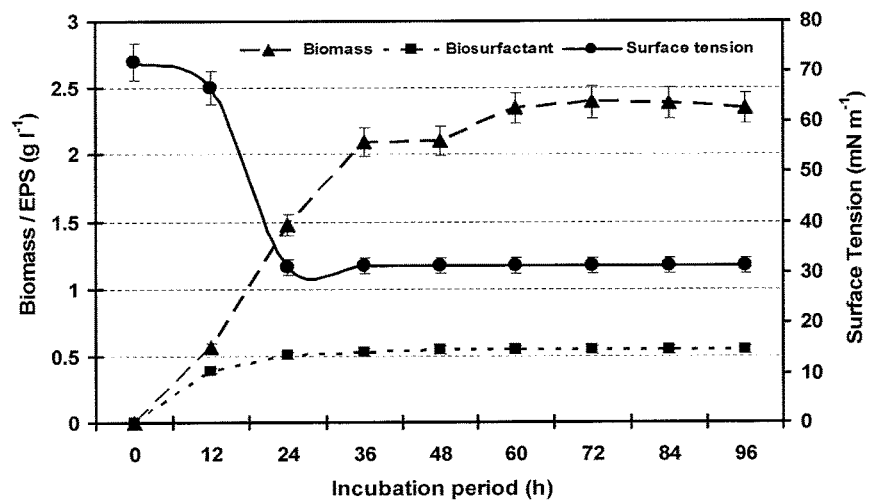
Figure 2B:
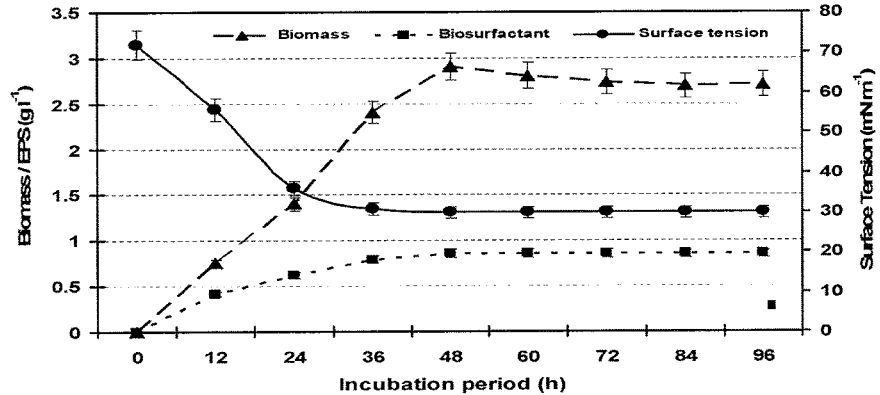

The *Microbacterium* sp. strain BS-2 when cultivated in minimal medium supplemented with glucose (1%, v/v) as a carbon source produced biosurfactant which was growth-associated (FIG. 2A). After 48 h of cultivation, the biosurfactant production reached to its maximum of 0.54 g $l^{-1}$, while a lowest surface tension value of 31.08 mN $m^{-1}$ was recorded at 24 h. The production and surface tension values of the biosurfactant remained constant until 96 h, when the culture attained the stationary growth phase. While, in case of *Brevibacillus* sp. strain BS-207, the produced biosurfactant was growth-associated (FIG. 2B). Further, after 48 h of cultivation, the biosurfactant production reached to its maximum of 0.86 g $l^{-1}$, while a lowest surface tension value of 29.9 mN $m^{-1}$ was recorded at 48 h. The biosurfactant production and surface tension values remained constant until 96 h, till the culture attained the stationary growth phase.

Figure 7A:
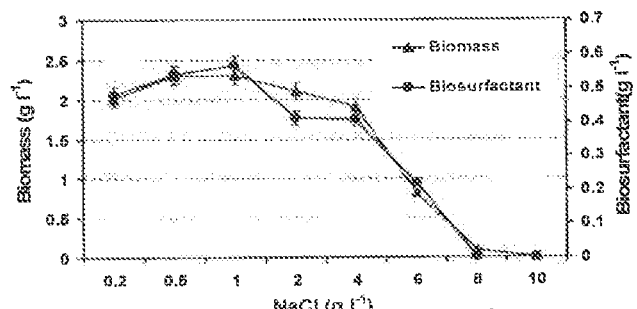
FIGS. 7A-7B depicts effect of sodium chloride concentration on production of polymeric biosurfactants by 7A *Microbacterium* sp. strain BS-2 and 7B *Brevibacillus* sp. strain BS-207.
Figure 7B:
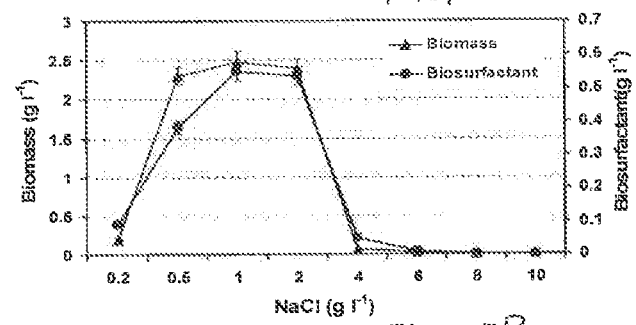
Figure 8A:
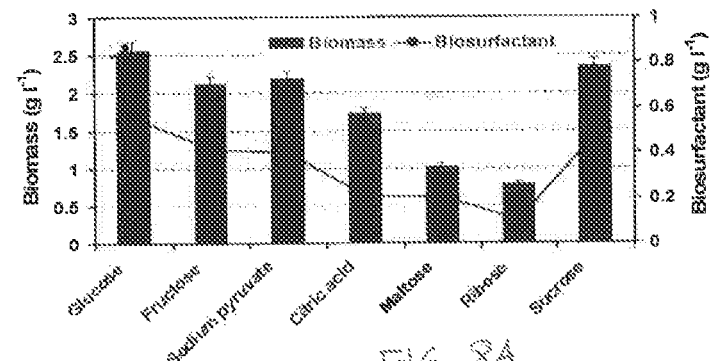
FIGS. 8A-8B depicts effect of different carbon sources on production of polymeric biosurfactants by 8A *Microbacterium* sp. strain BS-2 and 8B *Brevibacillus* sp. strain BS-207
Figure 8B:
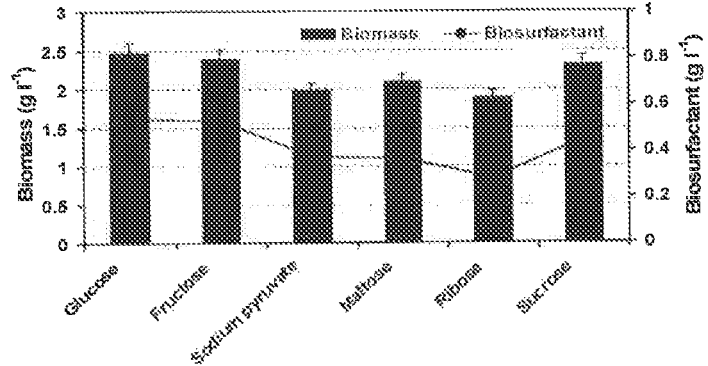

Parametric optimization studies indicated that biosurfactant production (0.54 g $l^{-1}$) by *Microbacterium* sp. strain BS-2 increased with an initial increase in pH and peaked at pH 8.0 after 72 h (FIG. 3A). The bacterium showed biosurfactant production of 0.54 g $l^{-1}$ at pH 7.5 and 0.55 g $l^{-1}$ at pH 8. However, in case of *Brevibacillus* sp. strain BS-207, the optimal biosurfactant production was 0.56 g $l^{-1}$ at pH 7.5 after 72 h (FIG. 3B). Maximum biosurfactant production was observed in the temperature ranging between 30° C. to 40° C. with an optimum biosurfactant production of 0.55 g $l^{-1}$ observed at temperature of 35° C. after 72 h in *Microbacterium* sp. strain BS-2 (FIG. 4A) and *Brevibacillus* sp. strain BS-207 (FIG. 4B), respectively. At temperatures above 40° C. and below 30° C. resulted in a decline in biosurfactant production. Since both the isolates, *Microbacterium* sp. strain BS-2 and *Brevibacillus* sp. strain BS-207 are strictly aerobic in nature and under shaking conditions the rate of biosurfactant production increased with an increase in agitation rate and maximum biosurfactant production of 0.56 g $l^{-1}$ (FIG. 5A) and 0.54 g $l^{-1}$ (FIG. 5B), respectively, was observed at 200 rev min. Among the different salts examined, sodium chloride proved effective at 0.05% (w/v) concentration for both *Microbacterium* sp. strain BS-2 (FIG. 6A) and *Brevibacillus* sp. strain BS-207 (FIG. 6B), but decreased at higher concentration and the maximum biosurfactant production was observed at 1 g $l^{-1}$ (w/v) in case of both *Microbacterium* sp. strain BS-2 (FIG. 7A) and *Brevibacillus* sp. strain BS-207 (FIG. 7B). Glucose was found to be the most effective carbon source followed by sucrose for both *Microbacterium* sp. strain BS-2 (FIG. 8A) and *Brevibacillus* sp. strain BS-207 (FIG. 8B), while lactose, xylose, arabinose, mannitol, sorbitol, fumaric acid, glycerol and starch did not support biosurfactant production for both the strains. Among the nitrogen sources tested, ammonium nitrate was observed as the most effective nitrogen source for biosurfactant production (0.25 g $l^{-1}$) followed by ammonium sulphate and sodium nitrate in case of *Microbacterium* sp. strain BS-2 (FIG. 9A), while soya peptone, soybean meal, peptone, casein and urea did not support biosurfactant production. However, in case of *Brevibacillus* sp. strain BS-207 (FIG. 9B), ammonium sulphate (0.25 g $l^{-1}$) followed by yeast extract were observed to be effective nitrogen sources for biosurfactant production. Further, when glucose and ammonium nitrate or ammonium sulphate were supplemented individually at various concentrations ranging from 5-60 g $l^{-1}$ and 0.5-6 g $l^{-1}$, respectively, in the minimal medium, maximum biosurfactant production was observed with supplementation of 25 g $l^{-1}$ (w/v) glucose (FIG. 10A) and 20 g $l^{-1}$ (w/v) glucose (FIG. 10B) and 2.5 g $l^{-1}$ (w/v) ammonium nitrate (FIG. 11A) and 2.0 g $l^{-1}$ (w/v) ammonium sulphate (FIG. 11B), respectively, for *Microbacterium* sp. strain BS-2 and *Brevibacillus* sp. strain BS-207. In addition, when the C:N ratio was 10, the maximum biosurfactant production observed was 1.39 g $l^{-1}$ after 72 h in case of *Microbacterium* sp. strain BS-2 (FIG. 12A) and 0.96 g $l^{-1}$ after 72 h in case of *Brevibacillus* sp. strain BS-207 (FIG. 12B). Further, when *Microbacterium* sp. strain BS-2 was cultured in 1 liter shake flasks under optimized submerged fermentation conditions at 35° C. with agitation at 200 rev $min^{-1}$ in a minimal salts medium (pH 8) supplemented with NaCl (1 g $l^{-1}$), glucose (25 g $l^{-1}$, w/v) and ammonium nitrate (2.5 g $l^{-1}$, w/v) as carbon and nitrogen sources, 1.405 g $l^{-1}$ of biosurfactant was produced after 72 h of incubation, and when *Brevibacillus* sp. strain BS-207 was cultured in I liter shake flasks under optimized submerged fermentation conditions at 35° C. with agitation at 200 rev min$^{-1}$ in a minimal salts medium (pH 7.5) supplemented with NaCl (1 g l$^{-1}$), glucose (20 g l$^{-1}$, w/v) and ammonium sulphate (2 g l$^{-1}$, w/v) as carbon and nitrogen sources, 1.17 g l$^{-1}$ of biosurfactant was produced after 72 h of incubation.

Example 3

Extraction and Purification of Polymeric Biosurfactants from *Microbacterium* Sp. Strain BS-2 and *Brevibacillus* Sp. Strain BS-207

*Microbacterium* sp. strain BS-2 and *Brevibacillus* sp. strain BS-207 were cultured under optimized submerged fermentation conditions as indicated in Example 2. After fermentation, the medium was centrifuged (Sorvall RC5C Plus, Kendro Lab Products, Ashville, N.C., USA) at 8,000 rev min$^{-1}$ at 4° C. to obtain the cell-free supernatant and the biosurfactant was extracted with 90% ice cold isopropanol. The extract was centrifuged at 10,000 rpm for 20 min and filtered through 0.45 μm Whatman filter paper and then precipitated with 95% ice cold ethanol. The extract was dialyzed (molecular weight cut-off 6000-8000 Da) against deionized water for 48 h at 4° C. and then purified on a DEAE-cellulose (Cl$^-$) column (2.5×50 cm) eluted with 0.1 N NaCl. The purified polymeric biosurfactants from *Microbacterium* sp. strain BS-2 and *Brevibacillus* sp. strain BS-207 were termed as Microsan and Brevisan.

Example 4

Characterization of Polymeric Biosurfactants from *Microbacterium* Sp. Strain BS-2 and *Brevibacillus* Sp. Strain BS-207

The Microsan and Brevisan polymeric biosurfactants recovered and purified in Example 3 were subjected to structural characterization. The average molecular weight (Mw) of EPS was determined by gel permeation chromatography [Agilent 1100 Series HPLC system, TOSOH Corporation, Japan, equipped with a RID and a TSK G5000PWXL gel column (7.8×300 mm) and a TSK PWXL (6.0 mm×40 mm) guard column] using dextran standards ranging from 10680 to 578500 Da (Sigma, CAS No. 9004-54-0). The Fourier transform infrared spectra (FT-IR) were recorded on the Thermo-Nicolet Nexus 670 FT-IR spectrophotometer (Thermo Fisher Scientific Inc., Madison, Wis., U.S.A.) using KBr pellets containing 1% finely ground EPS samples and the spectra was collected at a resolution of 4 cm$^{-1}$ in the wavenumber region of 400-4,000 cm. The cross-polarization/magic angle spinning (CP/MAS) $^{13}$C NMR experiments were performed on a Varian Unity Innova spectrometer operating at 400 MHz for $^1$H and 100 MHz for $^{13}$C at room temperature. The EPS samples used for solid-state NMR analysis were gently grinded to ensure sample homogeneity and were packed in a zirconium oxide rotor, sealed with a Kel-f cap. The CP time was 4 ms and the rotor spinning frequency was 10 kHz. The $^1$H and $^{13}$C pulse widths were 2.9 μs and 3.5 μs, respectively, with a repetition time of 4 sec. The spectral width was 33183.3 Hz with an accumulation of 512 scans. The data was processed with 8192 data points (Fourier number) with an exponential line broadening of 30 Hz. Thermal degradation analyses of the EPS samples were measured using a DSC 821$^e$ (Mettler Toledo GmbH, Switzerland) interfaced with Mettler Toledo Star SW (version 8.10) software. The raw and treated samples (ca. between 6-8 mg) were heated from room temperature to 600° C. at a heating rate of 10° C. mini. The DSC head was purged with oxygen-free nitrogen at a flow rate of 20 ml min. The DSC instrument was calibrated for temperature and heat flow using indium metal before measurements. The XPS measurements of the EPS samples were carried out on KRATOS AXIS 165 Ultra Photoelectron Spectrophotometer operated at 15 KV and 20 mA using Al Kα (1486.6 eV) radiation. The takeoff angle, defined as the angle between the substrate normal and the detector, was fixed at 90°. The EPS samples were mounted on standard sample studs by using a double sided adhesive tape. Binding energies were calibrated using the C (1 s) peak (286 eV). The analysis consisted of a broad survey scan (20.0 eV pass energy) for major element composition and a high-resolution scan (80.0 eV pass energy) for component speciation. All of the XPS analyses were carried out in duplicates (two independent samples of each type of EPS analyzed at different time intervals). Purified Microsan from *Microbacterium* sp. strain BS-2 was a white fibrous solid (1.405 g l$^{-1}$), with an average molecular weight (Mw) of 36663 KDa and intrinsic viscosity of 1.0 dL/g, as revealed by gel permeation chromatography analysis (FIG. 13A), while Brevisan from *Brevibacillus* sp. strain BS-207 was a white solid (1.391 g l$^{-1}$), with an average molecular weight (Mw) of 42260 KDa and intrinsic viscosity of 1.0 dL/g, as revealed by gel permeation chromatography analysis (FIG. 13B). The FT-IR spectrum of Microsan from *Microbacterium* sp. strain BS-2 (FIG. 14A) showed a broad stretching peak at 3421 cm$^{-1}$ which correspond to —(OH) group, v=2929.5 and 1070 cm$^1$ represented the carbon-hydrogen and carbon-oxygen stretching vibrations, respectively, while v=1650 and 1550 cm$^{-1}$ were attributed to the amide bond of proteins, a broad stretch at 1000-1200 cm$^{-1}$ correspond to the CO—C and CO bonds of carbohydrates and v=693.39 cm$^{-1}$ indicated the presence of anomeric region. While, the FT-IR spectrum of Brevisan from *Brevibacillus* sp. strain BS-207 (FIG. 14B) showed a broad stretching peak at 3429 cm$^{-1}$ which correspond to —OH group, while v=2924.5 and 1073 cm$^{-1}$ represented the C—H and C—O stretching vibrations, respectively. The characteristic absorption peak at v=693.39 cm$^{-1}$ suggested the presence of anomeric region in the EPS. The X-ray photoelectron spectrum of Microsan from *Microbacterium* sp. strain BS-2 (FIG. 15A) showed the presence of O (1s) (533 eV), N (1s) (401 eV) and C (1s) (286 eV) peaks, respectively. The sulphur peak at 168 eV (S 2p) indicated that the purified Microsan is a sulphated polysaccharide. Further, the X-ray photoelectron spectrum of Brevisan from *Brevibacillus* sp. strain BS-207 (FIG. 15B) showed the presence of O (1s) (533 eV) and C (1s) (286 eV) peaks. The absence of sulphur peak indicated that the purified Brevisan is a non-sulphated polysaccharide. The $^{13}$C CP/MAS NMR (400 MHz) spectrum of Microsan from *Microbacterium* sp. strain BS-2 (FIG. 16A) showed a chemical shift at δ=173.178 ppm (COO) which corresponded to the carboxyl carbon. The peaks at δ=145.469 ppm (HN—CO) and δ=99.394 ppm corresponded to amide carbon and anomeric carbon signals, respectively. The peaks at δ=71.202 ppm (—CHO) and δ=62.261 ppm (—C$_6$) corresponded to the carbonyl signals of the aldehyde group and C$_6$ carbon signals, respectively. The peak at δ=54.367 ppm represented the aliphatic carbon signals of N-acetyl uronic acid. The peaks at δ=33.826, 35.296 and 23.033 ppm (—CH$_2$—) were attributed to the methylene carbons, while δ=14.333 ppm (—CH$_3$) corresponded to the carbon signals of end methyl groups. In case of *Brevibacillus* sp. strain BS-207, the $^{13}$C CP/MAS NMR (400 MHz) spectrum of Brevisan (FIG. 16B) showed a chemical shift at δ=173.94 ppm (COO) which corresponded to the carboxyl carbon. The peaks at δ=99.94 ppm corresponded to anomeric carbon signals, respectively. The peaks at δ=71.267 ppm (—CHO) and δ=62.261 ppm (—$C_6$) indicated the carbonyl signals of the aldehyde group and $C_6$ carbon signals, respectively. The peaks at δ=32.996 and 23.033 ppm (—$CH_2$—) were attributed to the methylene carbons, while δ=14.33 ppm (—$CH_3$) represented the carbon signals of end methyl groups. From the TGA analysis, it was observed that the purified polymeric biosurfactants were thermally stable with a degradation temperature of 280° C. in case of Microsan from *Microbacterium* sp. strain BS-2 (FIG. 17A) and 330° C. in case of Brevisan from *Brevibacillus* sp. strain BS-207 (FIG. 17B).

Further, the polymeric biosurfactants were acid hydrolyzed (water, trifluoroacetic acid and acetic acid, 75:5:20, v/v), heated at 120° C. for 6 h and vacuum evaporated, followed by deacetylation with trifluoroacetic acid and water (10:90, v/v), heated at 80° C. for 30 min and then vacuum evaporated. The hydrolyzed products were subjected to calorimetric analysis of proteins, sugars and uronic acids using Bradford method [Bradford, M. M. (1976) *Anal. Biochem.* 72, 248-258], phenol sulphuric acid method and Elson-Morgan reaction methods [Chaplin, M. F. and Kennedy, J. F. (1986) Carbohydrate analysis: A practical approach. Washington, D.C.:IRL Press: 129-136], respectively, using appropriate standards. The calorimetric analysis of Microsan purified from *Microbacterium* sp. strain BS-2 showed the presence of sugars as a major component (92%) with proteins and uronic acids accounting for about 6% and 2%, respectively, while Brevisan purified from *Brevibacillus* sp. strain BS-207 showed the presence of sugars as the constituent. From the spectral and calorimetric analysis as described in the present example, it was evident that the purified biosurfactants were polysaccharide in nature.

Example 5

Analysis of Monosaccharide Composition and Glycosidic Linkage of Polymeric Biosurfactants from *Microbacterium* Sp. Strain BS-2 and *Brevibacillus* Sp. Strain BS-207

The monosaccharide composition of the purified Microsan from *Microbacterium* sp. strain BS-2 and Brevisan from *Brevibacillus* sp. strain BS-207 were determined from the analysis of methyl glycosides. The purified polymeric biosurfactants were subjected to methanolysis in 1.5 M methanol/HCl for 16 h at 80° C. and then trimethylsilylated using the previously described method [Sweeley, C. C., Bentley, R., Makita, M. and Wells, W. W. (1963) *J. Am. Chem. Soc.* 85, 2497-2507]. The methyl glucosides were analyzed by GC and compared with standard monosaccharides.

The purified polymeric biosurfactants were carboxyl-reduced according to the previously described method [Fontaine, T., Fournet, B. and Karamanos, Y. (1994) *J. Microbiol. Meth.* 20, 149-157]. The polymeric biosurfactants were dissolved in dimethyl sulfoxide and methyl esterified with diazomethane overnight at room temperature. Then it was reduced with 1 M imidazole/HCl buffer (pH 7) and NaBH$_4$. The reduction was stopped by the addition of glacial acetic acid. Further, the native and carboxyl reduced polymeric biosurfactants were methylated [Hakomori, S. (1964) *J. Biochem.* 55, 205-208] with dimethyl sulfoxide/methylsulfinyl potassium carbanion and methyl iodide. The permethylated products were hydrolyzed with 2 M trifluoroacetic acid for 2 h at 100° C. and then reduced overnight with NaBH$_4$ at room temperature. The reduced products were then acetylated with acetic acid/pyridine for 1 h, 100° C. to form partially methylated alditol acetates which were analyzed by GC (program A) and GC/MS [electronic impact (EI) mode, program C].

The polymeric biosurfactants were also further subjected to Lithium-ethylenediamine degradation [Mort, A. J. and Bauer, W. D. (1982) *J. Biol. Chem.* 257, 1870-1875]. The EPS (30 mg) was dissolved in 2 mL of ethylenediamine and lithium wire (3-4×3 mm) was added and incubated for 1 h at room temperature. Then the mixture was cooled in an ice bath and the reaction was stopped by the addition of water. The product was evaporated, dissolved in water and then fractionated on a Bio-Gel P-4 column. The resulting degraded products were converted to partially methylated alditol acetates as described above and was analyzed relative to 1,5-di-O-acetyl-2,3,4,6-tetra-O-methylglucitol. The partially methylated alditol acetates were analyzed on a GC-MS Micromass apparatus (Waters Corp., Milford, Mass., USA) equipped with an HP-5MS column (Agilent Technologies, Wilmington, Del., USA) using a temperature program of 120-180° C. ramped at 5° C./min and 180-250° C., ramped at 2° C./min and the mass conditions were: ionization mode with EI, ionization energy of 70 eV, a current intensity of 500 μA, and ion source temperature at 250° C.

The GC analysis of methyl glycosides showed the presence of glucose and mannose in case of Microsan from *Microbacterium* sp. strain BS-2 (FIG. 18A) and mannose and galactose in the ratio of 1:1 in case of Brevisan from *Brevibacillus* sp. strain BS-207 (FIG. 18B). The partially methylated alditol derivatives from the native and carboxyl reduced Microsan from *Microbacterium* sp. strain BS-2 showed the presence of a terminal glucopyranosyl residue, 4-linked glucopyranosyl, 1,2-disubstituted mannopyranosyl (Table 4 and FIG. 19A), while in case of Brevisan from *Brevibacillus* sp. strain BS-207 showed the presence of galactopyranosyl and mannopyranosyl as terminal residues, 4-linked galactopyranosyl and 4-linked mannopyranosyl residues (Table 5 and FIG. 19B). The presence of 1,5-di-O-acetyl-2,3,4,6-tetra-O-methyl-D-glucitol in carboxyl reduced EPS indicated the presence of glucuronic acid. The analysis indicated that Microsan from *Microbacterium* sp. strain BS-2 was composed of glucose, mannose and glucuronic acid residues with (1→4) and (1→2) linkages (Table 4 and FIG. 20A), however, Brevisan from *Brevibacillus* sp. strain BS-207 was mainly composed of galactose and mannose with (1→4) linkages (Table 5 and FIG. 20B). The analysis of partially methylated alditol acetates of Lithium-ethylenediamine degraded Microsan from *Microbacterium* sp. strain BS-2 (Table 6 and FIGS. 21A, 22 to 25) showed 1,5-di-O-acetyl-2,3,4,6-tetra-O-methyl-D-glucitol which represented the presence of glucopyranosyl residues at the terminal position. The 1,4,5-tri-O-acetyl-2,3,6-tri-O-methyl derivative corresponded to the presence of 4-linked glucopyranosyl residue. The 1,2,4,5-tetra-O-acetyl-3,6-di-O-methyl derivative indicated the 2,4-linked mannopyranosyl, while the 1,5-di-O)-acetyl-2,3,4,6-tetra-O-methyl-D-glucitol revealed that the glucuronic acid was linked to (1→2) mannopyranosyl residue. However, in case of Brevisan from *Brevibacillus* sp. strain BS-207 (Table 7 and FIGS. 21B, 26 to 29) showed the presence of 2,3,4,6-tetra-O-methyl-1,5-di-O-acetyl-D-galactocitol and 2,3,4,6-tetra-O-methyl-1,5-di-O-acetyl-D-mannitol derivatives which represented the galactopyranosyl and mannopyranosyl residues at the terminal positions. Further, the 2,3,6-tri-O-methyl-1,4,5-tri-O- acetyl-D-mannitol derivative indicated the presence of 4-linked mannopyranosyl residues, while 2,3,6-tri-O-methyl-1,4,5-tri-O-acetyl-D-galactacitol derivative represented the 4-linked galactopyranosyl residues, respectively.

Example 6

Analysis of Conformational Structures of Microsan from *Microbacterium* Sp. Strain BS-2 and Brevisan from *Brevibacillus* Sp. Strain BS-207

The helix coil transition of the polymeric biosurfactants was characterised by measuring the $\lambda_{max}$ of Congo red-EPS complexes in various concentrations ranging from 0.01 to 0.5 N NaOH solution [Ogawa, K. and M. Hatano. (1978) *Carbohydr. Res.* 67, 527-535.]. The aqueous solution of polysaccharide (1 mg/ml) pretreated with 100 µl of 0.5 mg/ml Congo red was treated with different concentrations of NaOH solution and the absorption spectra was recorded on a UV/Vis spectrophotometer using commercially available dextran (Sigma, CAS No. 9004-54-0) and laminarin (Sigma CAS No. 9008-22-4) as standards. From the Congo red analysis, it was observed that dextran with a random coil conformation and laminarin with triple helical conformation exhibited absorption maxima around 450 nm and 550 nm, respectively, while Microsan from *Microbacterium* sp. strain BS-2 exhibited absorption maximum around 450 nm similar to that of dextran (FIG. 30A), while Brevisan from *Brevibacillus* sp. strain BS-207 exhibited absorption maxima around 550 nm similar to that of laminarin (FIG. 30B). The analyses in the present example indicated that Microsan from *Microbacterium* sp. strain BS-2 has a random coil conformation, while Brevisan from *Brevibacillus* sp. strain BS-207 has a triple helical confirmation.

Example 7

Identification of Anomeric Configurations of Microsan from *Microbacterium* Sp. Strain BS-2 and Brevisan from *Brevibacillus* Sp. Strain BS-207

The anomeric configurations of polymeric biosurfactants were detected by staining analysis using Fungi-Fluor Kit (Polysciences, Warrington, Pa., USA). The aqueous solutions of Microsan from *Microbacterium* sp. strain BS-2 and Brevisan from *Brevibacillus* sp. strain BS-207 were placed on two different slides, dried and methanol was added. After 30 min, few drops of Fungi-Fluor Solution A containing Cellufluor, water and potassium hydroxide was added and incubated for 3 min. The slides were washed with distilled water and the fluorescence level was determined using a UV Illuminator (Vilber Lourmat Inc., France). Commercially available dextran and laminarin were stained in parallel. From the Fungi-Fluor staining, it was observed that dextran, the α-linked polysaccharide, did not exhibit fluorescence, while the EPS from both *Microbacterium* sp. strain BS-2 and *Brevibacillus* sp. strain BS-207 exhibited fluorescence similar to laminarin, a n-linked polysaccharide (FIG. 31A, B). Further, the surface morphology of dried EPS was analyzed by scanning electron microscopy (SEM Model S-520, Hitachi, Japan) which indicated the porous structure of the polysaccharides (FIG. 32A,B). The Fungi-Fluor staining analysis described in the present example indicated that Microsan from *Microbacterium* sp. strain BS-2 and Brevisan from *Brevibacillus* sp. strain BS-207 are mainly β-linked polysaccharides. The above examples indicated that the Microsan from *Microbacterium* sp. strain BS-2 is a β-(1→4),(1→2)-linked polysaccharide in random coil confirmation with glucose, mannose and glucuronic acid residues (FIG. 33A), while the Brevisan from *Brevibacillus* sp. strain BS-207 is a β-(1→4)-linked polysaccharide in triple helical confirmation with galactose and mannose residues (FIG. 33B).

Example 8

Determination of Surface-Active Properties for Microsan from *Microbacterium* Sp. Strain BS-2 and Brevisan from *Brevibacillus* Sp. Strain BS-207

The surface tension of the purified Microsan from *Microbacterium* sp. strain BS-2 and Brevisan from *Brevibacillus* sp. strain BS-207 was measured by Wilhelmy plate method using a Du-Nouy K100MK2 Processor Tensiometer (Krüss, Hamburg, Germany) which reduced the surface tension of water from 72 to 31.2 mN m$^{-1}$. The interfacial tension value was measured by Du-Nouy ring method and it was determined as 25.7 mN m. The critical micelle concentration (CMC) was measured by plotting the concentration of EPS as a function of surface tension. The CMC is the point where the slope of the curve abruptly changed was determined as 75 mg l$^{-1}$. The emulsification index (EI$_{24}$) was determined by the addition of 4 ml of culture supernatant to 6 ml of various hydrocarbons (N-Hexadecane, tridecane, hexane, toluene and xylene) and oils (mineral oil and soybean oil) and the mixtures were vortexed for 2 min and allowed to stand for 24 h. The emulsification index (EI$_{24}$) values expressed as the percentage of height of emulsified layer to the height of total liquid column. The emulsification index (EI$_{24}$) values observed for Microsan from *Microbacterium* sp. strain BS-2 and Brevisan from *Brevibacillus* sp. strain BS-207 were N-hexadecane (67%, 71%) tridecane (77%, 69%), hexane (83.7%, 71%), toluene (74.9%, 78%), xylene (66.89%, 68%), mineral oil (71.9%, 68.9%) and soybean oil (63%, 71.9%), respectively.

Example 9

Antioxidant Activities of Microsan from *Microbacterium* Sp. Strain BS-2 and Brevisan from *Brevibacillus* Sp. Strain BS-207

The antioxidant activity of Microsan from *Microbacterium* sp. strain BS-2 and Brevisan from *Brevibacillus* sp. strain BS-207 in cell free system was measured by its inhibitory activity on the generation of DPPH free radicals, superoxide anions (O$^{2-}$), lipid peroxidation and erythrocyte hemolysis. The DPPH free radical scavenging assay was performed using 2,2-diphenyl-1-picrylhydrazyl (DPPH) free radical scavenging method [Ara. N. and Hasan, N. (2009) *Res. J. Med. Medical Sci.* 4, 107-110]. Different concentrations of Microsan and Brevisan were mixed individually with 150 µl of 160 µM methanolic solution of DPPH and incubated at 35° C. for 30 min in dark. The effective concentration (EC$_{50}$) was calculated by measuring the absorbance of the samples at 517 nm. The superoxide anion scavenging was measured using phenazine methosulfate-nicotinamide adenine dinucleotide (PMS/NADH) method as previously described [Liu, F., Ooi, V. E. and Chang, S. T. (1997) *Life Sci.* 60, 763-771]. The lipid peroxidation assay was performed using the previously described method [Zhang, Q., Yu, P., Li, Z., Zhang, H., Xu, Z. and Li, P. (2003) *J. Appl. Phycol.* 15, 305-310] which is based on measuring the lipid peroxide decomposed product malondialdehyde (MDA). Further the erythrocyte hemolysis assay was performed using the previously described protocol [Ng, T. B., Liu, F. and Wang, Z. T. (2000) *Life Sci.* 66, 709-723]. Human blood sample was collected in 3% sodium citrate and centrifuged at 3,000×g for 10 min. The separated erythrocytes were washed and suspended in PBS buffer (pH 7.4). Different concentrations of Microsan and Brevisan were mixed with 1 ml of 1.25% erythrocyte suspension and 0.5 mL of 2.5 mM $H_2O_2$. Samples were incubated at 37° C. for 30 min and the absorbance was measured at 540 nm. The results are the average of three independent experiments and ascorbic acid was used as standard. Both EPS showed a dose dependent scavenging of DPPH free radicals, superoxide anions ($O^{2-}$) and lipid peroxidation and also exhibited dose dependent inhibition of erythrocyte hemolysis as shown in FIG. 34A,B. In case of Microsan from *Microbacterium* sp. strain BS-2, the $EC_{50}$ values for DPPH free radical scavenging, superoxide anions ($O^{2-}$) scavenging, lipid peroxidation inhibition and erythrocyte hemolysis inhibition were 40.78, 24.48, 165.94 and 139.28 µg $ml^{-1}$, respectively, and 39.97, 37.88, 81.98 and 79.98 µg $ml^{-1}$, respectively, were observed in case of Brevisan from *Brevibacillus* sp. strain BS-207, while ascorbic acid exhibited $EC_{50}$ values of 40.28, 21.1, 130.97 and 119.8 µg $ml^{-1}$, respectively. The present example indicated that Microsan from *Microbacterium* sp. strain BS-2 and Brevisan from *Brevibacillus* sp. strain BS-207 acted as antioxidants with effective scavenging of DPPH free radicals, superoxide anions and lipid peroxyl radicals along with hemolytic inhibitory activity.

Example 10

Synthesis and Characterization of Gold Nanoparticles Using Microsan from *Microbacterium* Sp. Strain BS-2

The gold nanoparticles were synthesised using by mixing 5 ml of different concentrations of Microsan (M-EPS) (0.005%, 0.01%, 0.02%, 0.03% and 0.05%) with 3 ml of $2.0\times10^{-4}$ (M) aqueous solution of $HAuCl_4.4H_2O$. The mixtures were heated at 80° C. in a water bath with continuous stirring for 10 min. The gold nanoparticles formed (M-EPS-Au-NP) were characterised by UV-visible absorption spectra. Further the effect of temperature and pH on the synthesis of M-EPS-Au-NP was studied. The UV-visible absorption spectra revealed a sharp absorption peak at 532 nm when 0.01% of EPS was used (FIG. 35). From the UV-visible spectral analysis of M-EPS-Au-NP nanoparticles synthesised at different temperatures, sharp absorption peaks were observed at 532 nm with temperature ranging between 60 to 100° C. (FIG. 36). The time-dependent analysis showed that gold nanoparticles (M-EPS-Au-NP) were formed after 10 min, heated at 80° C. (FIG. 37). At pH 6, the gold nanoparticles (M-EPS-Au-NP) showed a sharp absorption peak at 532 nm as revealed from UV-visible spectra (FIG. 38). The gold nanoparticles (M-EPS-Au-NP) synthesized with 0.01% of EPS at pH 6 and temperature of 80° C. were 8-10 nm in size as observed from TEM analysis (FIG. 39). The X-ray diffraction (XRD) pattern recorded on X'Pert PRO PAnalytical-PW 3040/60 X-ray diffractometer using CuKα radiation ($\lambda$=0.154056 nm) showed the characteristic peaks at 2θ=38.48, 44.54 and 64.88 due to (111), (200) and (220) planes of fcc gold crystal (FIG. 40), which confirmed with the SAED results (c). The nanoparticle charge quantified as zeta potential was measured using a Zetasizer Nano ZS which was −33 mV (FIG. 41). The X-ray photoelectron spectroscopic analysis showed the binding energy peaks of Au 4f7/2 and Au 4f5/2 at <84.2 and <87.3 eV indicating the formation of the metal Au (0) nanoparticles (FIG. 42). The energy dispersive X-ray spectroscopy (EDS) analysis revealed the elemental composition profile of the synthesized nanoparticles which suggested gold as the constituent element (FIG. 43). The Differential Light Scattering (DLS) analysis showed that the M-EPS-Au-NP nanoparticles size averaged between 5-10 nm (FIG. 44).

Example 11

Antimicrobial Activity of Microsan and M-EPS-Au-NP

The antimicrobial activity of Microsan and M-EPS-Au-NP was determined using the microtiter broth dilution method [Kumar, C. G. and Mamidyala, S. K. (2011) *Coll. Surf B: Biointerf.* 84, 462-466]. Different bacterial pathogens ($10^7$ cfu $ml^{-1}$ cells) were inoculated in 100 µl of Muller-Hinton broth. Different concentrations of Microsan, M-EPS-Au-NP and Brevisan were added to each strain and incubated for 24 h at 35° C. After incubation, 40 µl of p-iodonitrotetrazolium (INT, Sigma) dye (0.02%, 20 mg INT dissolved in 100 ml of 40% dimethyl formamide was added to each well and incubated for 2 h. The reduction of p-iodonitrotetrazolium was spectroscopically measured at 450 nm using TRIAD multimode reader (Dynex Technologies, Inc., Chantilly, Va.) to determine the minimum inhibitory concentration (MIC) values. Commercially available surfactin (CAS 24730-31-2; Sigma-Aldrich) and laminarin (CAS No 9008-22-4; Sigma-Aldrich) used as positive controls were run in parallel for comparison. The MIC values of Microsan and M-EPS-Au-NP observed against the tested bacterial strains are shown in Table 3. Microsan showed promising antibacterial activity (MIC of 4.68 µg $ml^{-1}$) against *Staphylococcus aureus* MLS16 MTCC 2940 and *Bacillus subtilis* MTCC 121, while M-EPS-Au-NP exhibited potent activity (MIC of 2.34 µg $ml^{-1}$) against *Staphylococcus aureus* MLS16 MTCC 2940 and *Klebsiella planticola* MTCC 530. The current example indicated that Microsan and M-EPS-Au-NP exhibited promising antimicrobial activity against the tested pathogenic bacterial strains. However, Brevisan did not exhibit antimicrobial activity against the tested bacterial strains.

Example 12

Effect of Microsan and M-EPS-Au-NP on the Proliferation of Raw 264.7 Macrophages The effect of Brevisan, Microsan and M-EPS-Au-NP on the proliferation of RAW 264.7 macrophages (ATCC No. CRL-2278) was measured by in vitro MTT assay using the previously described method [Mosmann, T. (1983) *J. Immunol. Methods* 65, 55-63], which is based on the cell-mediated reduction of tetrazolium salt to form water insoluble formazan crystals. The MTT assay was performed with different concentrations (1-200 µg ml-1) of Brevisan, Microsan and M-EPS-Au-NP were incubated for 48 h using laminarin as a control. The proliferation of RAW 264.7 cells was not significantly reduced at the tested concentrations of Brevisan, Microsan and M-EPS-Au-NP. At the used concentration of 200 µg ml-1 of Brevisan, Microsan and M-EPS-Au-NP, the observed cell proliferation was 91.88%, 89.07% and 88.98%, respectively (FIGS. 45a,b). The present example indicated that Brevisan, Microsan and M-EPS-Au-NP did not affect the proliferation of RAW 264.7 cells. Further, the localization of M-EPS-Au-N P was observed using the transmission electron microscope. From the TEM analysis, it was observed that Microsan-coated gold nanoparticles (M-EPS-Au-NP) were not aggregated and localized in vacuoles and cytoplasm (FIG. 46).

Example 13

Inhibition of LPS-Induced Reactive Oxygen Species (ROS) and Nitric Oxide (No) in Raw 264.7 Macrophages by Brevisan, Microsan and M-EPS-Au-NP The inhibition of intracellular reactive oxygen species (ROS) by Brevisan, Microsan and M-EPS-Au-NP in RAW 264.7 macrophages was measured using the oxygen free radical acceptor 2,7,-dichlorofluorescein diacetate (DCFH-DA) [Wang, H., and Joseph J. A. (1999) *Free. Radic. Biol. Med.* 27, 612-616] which is oxidized to the fluorescent compound, 2,7-dichlorofluorescein (DCF) by intracellular ROS. The RAW-264.7 macrophages ($2 \times 10^6$ cells/well in 24-well plate) were treated with Brevisan, Microsan and M-EPS-Au-NP at various concentrations and then stimulated with 100 ng/ml LPS for 24 h using N-acetylcysteine (NAC, 10 mM) as a ROS inhibitor. The DCF formed by intracellular ROS was measured at 485 nm excitation and 520 nm emission wavelengths using a Hitachi spectrofluorimeter. The experiments were run in triplicates and reported as the percentage of intracellular ROS formed.

Further, the effect of Brevisan, Microsan and M-EPS-Au-NP on LPS-stimulated nitric oxide (NO) in RAW 264.7 macrophages was determined by the Griess reaction assay [Yoon, S. B., Lee, Y. J., Park, S. K., Kim, H. C., Bae, H., Kim, H. M., Ko, S. G., Choi, H. Y., Oh, M. S., Park, W. (2009) *J. Ethnopharmacol.* 125, 286-290]. The RAW-264.7 macrophages were treated with Brevisan, Microsan and M-EPS-Au-NP at different concentrations and then stimulated with 100 ng ml$^{-1}$ of LPS. After 24 h, 100 μl of culture supernatant was collected and mixed with 100 μl of Griess reagent in a 96-well plate and incubated for 15 min at room temperature. The optical density was spectroscopically measured at 540 nm using TRIAD multimode reader (Dynex Technologies, Inc., Chantilly, Va.). The experiments were run in triplicates and reported as the percentage of NO produced. In RAW 264.7 macrophage cells the LPS-stimulated ROS levels were significantly inhibited by Brevisan, Microsan and M-EPS-Au-NP in a dose-dependent manner (FIGS. 47A,B). The LPS-induced ROS levels (78.97%) were reduced to 4.98%, 55.71% and 12.74% upon treatment with 20 μg ml$^{-1}$ of Brevisan, Microsan and M-EPS-Au-NP, respectively. Similarly, the LPS-stimulated NO production in RAW 264.7 cells was also significantly reduced in a dose-dependent manner as shown in FIGS. 48A,B. When the cells were exposed to 20 μg ml$^{-1}$ of Brevisan, Microsan and M-EPS-Au-NP the LPS-stimulated NO levels (66.87%) were significantly reduced to 3.18%, 20.05% and 4.09%, respectively. The present example illustrated that Brevisan and Microsan effectively inhibited the LPS-stimulated ROS and NO generation, while M-EPS-Au-NP significantly reduced the concentration of Microsan required for achieving the effective inhibition of ROS and NO in LPS-stimulated RAW 264.7 macrophage cells.

Example 14

Inhibition of LPS Induced Cyclooxygenase-2 in Raw 264.7 Cells by Brevisan, Microsan and M-EPS-Au-NP The inhibition of LPS induced cyclooxygenase-2 (COX-2) by Brevisan, Microsan and M-EPS-Au-NP was assessed by immunoblot analysis. In independent experiments, RAW-264.7 cells were treated with Brevisan, Microsan and M-EPS-Au-NP (10 and 50 μg ml$^{-1}$ each) and then stimulated with 100 ng ml$^{-1}$ of LPS. After 24 h, the cells were washed with PBS and suspended in a lysis buffer containing 20 mM Tris, I mM EDTA, 150 mM NaCl, 1% NP-40, 0.5% sodium deoxycholate, 1 mM β-glycerophosphate, 1 mM sodium orthovanadate, 1 mM PMSF, 10 mg ml$^{-1}$ leupeptin, 20 mg ml$^{-1}$ aprotinin. The mixture was centrifuged at 10,000 rpm at 4° C. for 10 min to obtain the cell lysate. The protein content was determined by Bradford method [Bradford, M. M. (1976) *Anal. Biochem.* 72, 248-258]. An equal amount of total cell lysate was resolved on 12% SDS-PAGE gels and then transferred onto nitrocellulose membranes. Membranes were blocked with 5% w/v non-fat dry milk and then incubated with the primary antibodies for mouse COX-2 and β-actin with gentle shaking at 4° C. for 12 h and then incubated with peroxidase-conjugated secondary antibodies. The blots were developed using peroxidase substrates, TMB (3,3,5,5-tetramethylbenzidine)/$H_2O_2$.

In RAW 264.7 macrophage cells, LPS (100 ng ml$^{-1}$) significantly induced COX-2 expression as compared to normal cells at 24 h. When the cells were exposed to 10 and 50 μg ml$^{-1}$ of Brevisan and Microsan for 24 h, the induction of COX-2 was significantly inhibited as depicted in FIGS. 49A,B. The LPS induced COX-2 was more significantly inhibited by M-EPS-Au-NP (50 μg ml$^{-1}$) at 24 h. The Western blot analysis described in the present example illustrated that the LPS-induced COX-2 in RAW 264.7 macrophages was effectively inhibited by Brevisan, Microsan and M-EPS-Au-NP.

Example 15

Inhibition of LPS Induced Pro Inflammatory Cytokines TNF-A and IL-6 by Brevisan, Microsan and M-EPS-Au-NP in Raw 264.7 Cells The effect of Brevisan, Microsan and M-EPS-Au-NP on the release of proinflammatory cytokines, TNF-α and IL-6, was measured using ELISA kits (Biosource International, Camarillo, Calif., USA). In independent experiments, the RAW-264.7 cells were treated with different concentrations (1, 10, 50 and 100 μg ml$^{-1}$) of Brevisan, Microsan and M-EPS-Au-NP and then stimulated with 100 ng ml$^{-1}$ of LPS. The supernatants were harvested after 24 h and the concentrations of TNF-α and IL-6 was measured using an ELISA kit according to the manufacturer's instructions. Brevisan, Microsan and M-EPS-Au-NP significantly reduced the LPS-induced cytokine production in RAW 264.7 macrophage cells in a dose-dependent manner. In RAW 264.7 cells, LPS induced the production of TNF-α and IL-6 at 215.79 μg ml$^{-1}$ and 190.9 μg ml$^{-1}$, respectively, which was inhibited to 98.88 μg ml$^{-1}$ and 90.01 μg ml$^{-1}$ respectively, by Microsan at 50 μg ml$^{-1}$ and 20.17 μg ml$^{-1}$ and 19.98 μg ml$^{-1}$, respectively, by Brevisan at 20 μg m$^{-1}$. Further, M-EPS-Au-NP at 50 μg ml$^{-1}$ inhibited TNF-α and IL-6 production to 12.37 μg ml$^{-1}$ and 15.7 μg ml$^{-1}$, respectively (FIGS. 50a, b and 51). The current example indicated that Brevisan, Microsan and M-EPS-Au-NP effectively inhibited the LPS-induced proinflammatory cytokines, TNF-α and IL-6, in RAW 264.7 cells.

Example 16

Inhibition of LPS Induced C3 Complement Component and C3 Hemolytic Activity by Brevisan in Raw 264.7 Macrophages The effect of Brevisan, Microsan and M-EPS-Au-NP on C3 complement component was measured using ELISA kits (Antibodies, Atlanta, USA). RAW 264.7 cells were treated with Brevisan, Microsan and M-EPS-Au-NP at 1, 10, 20 and 50 μg/ml, respectively, and then stimulated with 100 ng ml$^{-1}$ of LPS. After incubating for 24 h, 50 μl of supernatant was collected and added to each well in an antibody coated 96-well plate. After I h, the wells were washed with PBS and incubated with 100 μl of horse radish peroxidase (HRP)-conjugate for 1 h at 37° C. and then incubated with 50 μl of O-phenylenediamine (0.2% w/v in 0.017 M citrate phosphate buffer, pH 6) and 50 μl of 0.015% hydrogen peroxide for 15 min and the reaction was stopped by adding 50 μl of 12.5% sulphuric acid and the optical density was measured at 450 nm using Biotek EIA Reader (Biotek Instruments, Inc., VT, USA). The results shown are the average of three independent experiments. Further, the hemolytic activity of the secreted C3 was measured as described earlier [Gasque, P., Julen, N., Ischenko, A. M., Picot, C., Mauger, C., Chauzy, C., Ripoche, J. and Fontaine, M. (1992) *J. Immunol.* 149, 1381-1389]. In brief, the sheep erythrocytes (1×10) were sensitized with rabbit anti-(sheep erythrocyte) antibodies and mixed with 0.5 ml of R3 reagent [Fontaine, M., Joisel, F. and Dumouchel, L. (1980) *J. Immunol. Methods* 33, 145-158]. To this mixture, 500 μl of culture supernatant (collected after EPS treatment as described above) was added and incubated at 37° C. for 1 h. Then 1.5 ml of PBS was added, centrifuged at 10,000 rpm for 5 min and the hemoglobin released present in the supernatant was quantified by measuring the absorbance at 415 nm. All the experiments were run in triplicates and simultaneously normal cells treated with medium and reagent blank were run in parallel as controls.

Microsan and M-EPS-Au-NP did not inhibit the C3 complement component production, while Brevisan showed significant inhibition on the production of C3 complement component from RAW 264.7 macrophages and also inhibited the hemolytic activity of released C3 complement component. The C3 complement component released from the RAW 264.7 macrophages stimulated with 100 ng ml$^{-1}$ of LPS was 55.89 ng/10$^6$ cells ml$^{-1}$ and it was reduced to 2.99 ng/10$^6$ cells ml$^{-1}$ at 20 μg ml$^{-1}$ of Brevisan (FIG. 52), while C3 component produced in the normal cells was 1.81 ng/10$^6$ cells ml$^{-1}$. Further, the hemolytic activity of C3 complement component in LPS-stimulated RAW macrophages was 89.97% which was significantly reduced to 5.71% at 20 μg ml$^{-1}$ of Brevisan, whereas the hemolytic activity of C3 complement component in unstimulated macrophages was 5.04% (FIG. 53).

From the foregoing examples, it was inferred that the polymeric biosurfactants isolated from *Microbacterium* sp. strain BS-2 (Microsan) and *Brevibacillus* sp. strain BS-207 (Brevisan) exhibited good surface-active lowering and antioxidant activities. Microsan had reducing and stabilizing properties and acted as capping ligands in the synthesis of gold nanoparticles (M-EPS-Au-NP). The immunomodulatory effects of Brevisan, Microsan and M-EPS-Au-NP were revealed by their effective inhibition of LPS-stimulated ROS and NO in RAW 264.7 cells without affecting the cell proliferation. Further, Brevisan, Microsan and M-EPS-Au-NP inhibited LPS-stimulated cyclooxygenase-2 and the subsequent generation of proinflammatory cytokines, TNF-α and IL-6, in RAW 264.7 macrophages. Brevisan inhibited the production and hemolytic activity of C3 complement component from LPS-stimulated RAW 264.7 macrophages.

From the foregoing examples, it was inferred that Brevisan and Microsan exhibited broad spectrum of activities like antioxidant, anti-inflammatory and immunomodulating properties and finds application as potential immunosuppressive agents.

TABLE 1

Morphological, physiological and biochemical characteristics of *Microbacterium* sp. strain BS-2

1) Morphological characteristics

| | |
|---|---|
| a) Gram staining | Gram-positive |
| b) Shape | Rod shaped and non motile |
| c) Size | Moderate |
| d) Colony colour | Light yellow coloured |
| e) Colony shape | Circular |
| f) Colony size | 1 mm in diameter |
| g) Colony margin | Entire |
| h) Colony surface | Smooth |
| i) Colony elevation | Low convex |
| j) Colony consistency | Viscous |
| k) Optical features | Opaque |
| l) Pigments | No pigment formation |
| m) Endospore | No endospore formation |

Physiological characteristics

| | |
|---|---|
| a) Growth in broth | Abundant |
| b) Oxygen requirement | Aerobic |
| c) Temperature range | 20-45° C. with an optimum at 35° C. ± 2° C., but not above 45° C. |
| d) pH range | 6.0-10.0 with an optimum at pH 8, but is inhibited at pH <6.0 and >10 |
| e) Salt tolerance | NaCl concentration tolerance up to 6% |

Biochemical characteristics

| | |
|---|---|
| a) Indole test | Negative |
| b) Methyl red test | Negative |
| c) Vogues-Proskauer test | Negative |
| d) Simmon's citrate test | Negative |
| e) Nitrate reduction test | Negative |
| f) H$_2$S production | Negative |
| g) Urease test | Positive |
| h) Catalase test | Positive |
| i) Oxidase test | Negative |
| j) Lysine decarboxylase test | Negative |
| k) Ornitinine decarboxylase test | Negative |
| l) Arginine dehydrolase test | Negative |
| m) Protease test | Negative |
| n) Amylase test | Negative |
| o) Esculin hydrolysis test | Positive |
| p) Gelatin hydrolysis | Negative |
| q) Gas production from glucose | Negative |

Carbohydrate fermentation tests

Positive for maltose, glucose and sucrose
Negative for lactose, trehalose, arabinose, rhamnose, raffinose, xylose, mannose, melibiose, melizitose, sorbose, arabitol, sorbitol, dulcitol, inositol and mannitol.

Antibiotic sensitivity

Sensitive to Erythromycin (5 μg), Gentamicin (20 μg), Ciprofloxacin (1 μg), Tetracycline (5 μg), Chloramphenicol (10 μg), Moxifloxacin (5 μg), Penicillin G (10 units), Methicillin (1 μg), and Rifampicin (1 μg)
Resistant to Amphotericin B and Nystatin

TABLE 2

Morphological, physiological and biochemical characteristics of *Brevibacillus* sp. strain BS-207

1) Morphological characteristics

| | |
|---|---|
| a) Gram staining | Gram-positive |
| b) Shape | Rod shaped and motile |
| c) Size | Moderate |
| d) Colony colour | White |
| e) Colony shape | Circular |
| f) Colony size | 1 mm in diameter |

TABLE 2-continued

Morphological, physiological and biochemical characteristics of *Brevibacillus* sp. strain BS-207

| | |
|---|---|
| g) Colony margin | Entire |
| h) Colony surface | Smooth |
| i) Colony elevation | Convex |
| j) Colony consistency | Viscous |
| k) Optical features | Opaque |
| l) Pigments | No pigment formation |
| m) Endospore | Ellipsoidal endospores |

Physiological characteristics

| | |
|---|---|
| a) Growth in broth | Abundant |
| b) Oxygen requirement | Aerobic |
| c) Temperature range | 25-45° C. with an optimum at 35° C. ± 2° C., but not above 45° C. |
| d) pH range | 6.0-9.0 with an optimum at pH 7.5, but is inhibited at pH <6.0 and >9 |
| e) Salt tolerance | NaCl concentration tolerance up to 2% |

Biochemical characteristics

| | |
|---|---|
| a) Indole test | Negative |
| b) Methyl red test | Negative |
| c) Vogues-Proskauer test | Negative |
| d) Simmon's citrate test | Negative |
| e) Nitrate reduction test | Positive |
| f) $H_2S$ production | Negative |
| g) Urease test | Positive |
| h) Catalase test | Positive |
| i) Oxidase test | Negative |
| j) Lysine decarboxylase test | Negative |
| k) Ornitinine decarboxylase test | Negative |
| l) Arginine dehydrolase test | Negative |
| m) Protease test | Positive |
| n) Amylase test | Positive |
| o) Esculin hydrolysis test | Negative |
| p) Gelatin hydrolysis | Negative |
| q) Gas production from glucose | Negative |

Carbohydrate fermentation tests

Positive for maltose, glucose and sucrose
Negative for lactose, trehalose, glycerol, arabinose, rhamnose, raffinose, xylose, mannose, melibiose, melizitose, sorbose, arabitol, sorbitol, dulcitol, inositol and mannitol.

Antibiotic sensitivity

Sensitive to Erythromycin (5 μg), Gentamicin (20 μg), Ciprofloxacin (1 μg), , Kanamycin (10 μg), Chloramphenicol (10 μg), Moxifloxacin (5 μg), Penicillin G (10 units), Nystatin (10 μg), Methicillin (1 μg), and Rifampicin (1 μg)
Resistant to Tetracycline and Amphotericin B

TABLE 3

Antimicrobial activity of Microsan from *Microbacterium* sp. strain BS-2

| | Minimum inhibitory concentration (MIC, μg ml$^{-1}$) | | | |
|---|---|---|---|---|
| Bacterial strains* | Microsan | M-EPS-Au-NP | Laminarin | Surfactin# |
| *Staphylococcus aureus* MTCC 96 | 18.75 | 4.68 | 18.75 | 9.37 |
| *Staphylococcus aureus* MLS16 MTCC 2940 | 4.68 | 2.34 | 37.5 | 18.75 |
| *Bacillus subtilis* MTCC 121 | 4.68 | 4.68 | 9.37 | 4.68 |
| *Klebsiella planticola* MTCC 530 | 9.37 | 2.34 | 4.68 | 9.37 |
| *Micrococcus luteus* MTCC 2470 | >300 | >300 | 4.68 | 18.75 |
| *Escherichia coli* MTCC 739 | >300 | >300 | 18.75 | 9.37 |

TABLE 3-continued

Antimicrobial activity of Microsan from *Microbacterium* sp. strain BS-2

| | Minimum inhibitory concentration (MIC, μg ml$^{-1}$) | | | |
|---|---|---|---|---|
| Bacterial strains* | Microsan | M-EPS-Au-NP | Laminarin | Surfactin# |
| *Pseudomonas aeruginosa* MTCC 2453 | >300 | >300 | 4.68 | 18.75 |

*Bacterial strains were procured from Microbial Type Culture Collection, CSIR-Institute of Microbial Technology, Chandigarh, India
Positive controls procured from Sigma-Aldrich, MO, USA

TABLE 4

Alditol acetate derivatives of native and carboxyl reduced EPS produced from *Microbacterium* sp. strain BS-2

| | Molar ratio | | |
|---|---|---|---|
| Rt | Native EPS | Carboxyl reduced EPS | Alditol acetate derivatives |
| 15.44 | 2.4 | 2.2 | 1,5-di-O-acetyl-2,3,4,6-tetra-O-methyl-D-glucitol |
| 20.55 | 1.5 | 1.4 | 1,4,5-tri-O-acetyl-2,3,6-tri-O-methyl-D-glucitol |
| 24.0 | 0.7 | 0.9 | 1,2,4,5-tetra-O-acetyl-3,6-di-O-methyl-D-mannitol |
| 27.23 | — | 1.1 | 1,5-di-O-acetyl-2,3,4,6-tetra-O-methyl-D-glucitol |

Rt: Retention time

TABLE 5

Alditol acetate derivatives of native and carboxyl reduced EPS produced from *Brevibacillus* sp. strain BS 207

| | Molar ratio | | |
|---|---|---|---|
| Rt | Native EPS | Carboxyl reduced EPS | Alditol acetate derivative |
| 16.26 | 0.9 | 0.9 | 1,5-di-O-acetyl-2,3,4,6-tetra-O-methyl-D-galactocitol |
| 18.6 | 1.1 | 1.1 | 1,5-tri-O-acetyl-2,3,4,6-tri-O-methyl-D-mannitol |
| 20.6 | 2.4 | 2.41 | 1,4,5-tetra-O-acetyl-2,3,6-di-O-methyl-D-galactocitol |
| 26.88 | 2.45 | 2.39 | 1,4,5-di-O-acetyl-2,3,6-tetra-O-methyl-D-mannitol |

Rt: Retention time

TABLE 6

Alditol acetate derivatives of Lithium-ethylenediamine degraded EPS produced from *Microbacterium* sp. strain BS-2

| Rt | Alditol acetate derivatives | Type of linkage | Molar ratio |
|---|---|---|---|
| 16.08 | 1,5-di-O-acetyl-2,3,4,6-tetra-O-methyl-D-glucitol | Terminal Glucopyranosyl (1→4) | 0.9 |
| 17.58 | 1,4,5-tri-O-acetyl-2,3,6-tri-O-methyl-D-glucitol | Glucopyranosyl (1→4) | 1.3 |
| 20.01 | 1,2,4,5-tetra-O-acetyl-3,6-di-O-methyl-D-mannitol | Mannopyranosyl (1→4)(2→1) | 1.2 |
| 23.39 | 1,5-di-O-acetyl-2,3,4,6-tetra-O-methyl-D-glucitol | Glucuranopyranosyl (1→2) | 0.7 |

TABLE 7

Analysis of partially methylated alditol acetate derivatives of Lithium-ethylenediamine degraded EPS produced from *Brevibacillus* sp. strain BS-207

| Rt | Alditol acetate derivative | Type of linkage | Molar ratio |
|---|---|---|---|
| 14.16 | 2,3,4,6-tetra-O-methyl-1,5-di-O-acetyl-D-galactocitol | Terminal galactopyranosyl (1→4) | 0.3 |
| 14.80 | 2,3,4,6-tetra-O-methyl-1,5-di-O-acetyl-D-mannitol | Terminal mannopyranosyl (1→4) | 0.29 |
| 20.60 | 2,3,6-tri-O-methyl-1,4,5-tri-O-acetyl-D-mannitol | Mannopyranosyl (1→4) | 1.59 |
| 24.26 | 2,3,6-tri-O-methyl-1,4,5-tri-O-acetyl-D-galactacitol | Galactopyranosyl (1→4) | 1.6 |

ADVANTAGES OF THE INVENTION

1. Bacterial exopolysaccharides emerged as new, industrially important polymeric materials with significant economical value. They mediate diverse range of important biological processes. Several polysaccharides of microbial origin have been explored for their applications in food, cosmetics and pharmaceutical industries. Considering the biodiversity of microbial flora, a number of new microbial exopolysaccharides have been identified, however, only a few (dextran, xanthan and gellan gum) have been explored from an industrial and commercial viewpoint. Bacterial exopolysaccharides represent a greener approach for the production of industrially important polymers. These biopolymers exhibit a broad range of complex chemical structures and diverse properties providing ample opportunities for newer industrial applications. The bacterial exopolysaccharides described herein represent environmental-compatible and biodegradable class of polymers which have been explored from a pharmacological perspective.
2. The exopolysaccharides isolated from *Microbacterium* sp. strain BS-2 [MTCC 5822] and *Brevibacillus* sp. strain BS-207 [MTCC 5823] showed remarkable advantages offering potential immunomodulatory activities. The bacterial-derived polysaccharides under study exhibited diverse pharmacological effects via their ability to modulate macrophage immune function and antioxidant capacities.
3. Although relatively better antibiotics are available in the market, they have disadvantages in inducing antibiotic-resistant strains. The Microsan and Brevisan polysaccharides exhibited good surface-active and antimicrobial properties. The surface active property of these polysaccharides facilitates the preparation of formulations.
4. In the present invention, the Microsan and Brevisan polysaccharides inhibited the LPS-induced activation of RAW macrophages through inhibiting reactive oxygen species, reactive nitrogen species and inflammatory cytokines such as TNF-α and IL-6 and cyclooxygenase-2. Thus they are protective in nature against the deleterious effects of inflammatory cytokines and macrophage activation.
5. Among these polysaccharides, Brevisan in particular inhibited the production and hemolytic activity of C3 complement component in LPS-stimulated RAW 264.7 macrophages. Thus it can prevent the pathological conditions associated with complement upregulation.
6. The Microsan polysaccharide offered an efficient, non-toxic and greener approach for the synthesis of gold nanoparticles, since it acted as both reducing and capping agent. These Microsan-capped gold nanoparticles increased the anti-inflammatory properties in RAW macrophages.
7. Taking all together, Microsan and Brevisan exhibited multi-functional activities like antimicrobial, antioxidant, anti-inflammatory and immunomodulating properties and can find application as potential immunosuppressive agents.

We claim:

1. A biosurfactant capped gold nanoparticle comprising a polymeric biosurfactant, wherein said polymeric biosurfactant reduces and stabilizes the biosurfactant gold nanoparticle,
   wherein the polymeric biosurfactant is isolated from a bacterial strain,
   wherein the polymeric biosurfactant comprises glucuronic acid β-(1→2) mannose β-(1→4) glucose residues, and
   wherein the polymeric biosurfactant has a random coil confirmation.
2. The biosurfactant capped gold nanoparticle of claim 1, wherein 0.01% concentration of the biosurfactant is used to obtain the polymeric biosurfactant-capped gold nanoparticles.
3. The biosurfactant capped gold nanoparticle of claim 1, wherein the polymeric biosurfactant-capped gold nanoparticles exhibit antibacterial activity with MIC values ranging from 2.34 to 4.68 µg ml$^{-1}$.
4. The biosurfactant capped gold nanoparticle of claim 1, wherein 10-50 µg ml$^{-1}$ of the polymeric biosurfactant capped gold nanoparticle inhibits the lipopolysaccharide-induced reactive oxygen species (ROS) and nitric oxide (NO) generation levels by 12.74% and 4.09%, respectively, in RAW 264.7 macrophages.
5. The biosurfactant capped gold nanoparticle of claim 1, wherein 50-100 µg ml$^{-1}$ of the biosurfactant capped gold nanoparticle inhibits the lipopolysaccharide (LPS)-stimulated cyclooxygenase-2 (COX-2) and the subsequent generation of proinflammatory cytokines, TNF-α and IL-6, levels from 215.79 µg ml$^{-1}$ and 190.9 µg ml$^{-1}$, respectively, to 12.37 µg ml$^{-1}$ and 15.7 µg ml$^{-1}$, respectively, in RAW 264.7 macrophages.
6. The biosurfactant capped gold nanoparticle of claim 1, wherein the polymeric biosurfactant has an average molecular weight (Mw) of 36663 KDa and an intrinsic viscosity of 1.0 dL/g.

* * * * *